(12) United States Patent
Gao et al.

(10) Patent No.: US 10,787,639 B2
(45) Date of Patent: Sep. 29, 2020

(54) ECOSYSTEM FOR DETERMINING PLANT-MICROBE INTERACTIONS

(71) Applicant: The Regents of the University of California, Oakland, CA (US)

(72) Inventors: Jian Gao, Richmond, CA (US); Trent R. Northen, Walnut Creek, CA (US); Kyle M. Lewald, Lafayette, CA (US); Lloyd T. Cornmesser, San Ramon, CA (US); Peter F. Andeer, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/963,887

(22) Filed: Apr. 26, 2018

(65) Prior Publication Data

US 2018/0312800 A1   Nov. 1, 2018

Related U.S. Application Data

(60) Provisional application No. 62/490,548, filed on Apr. 26, 2017.

(51) Int. Cl.

| | |
|---|---|
| C12N 1/20 | (2006.01) |
| C12M 1/00 | (2006.01) |
| C12Q 1/02 | (2006.01) |
| A01N 63/00 | (2020.01) |
| A01N 63/30 | (2020.01) |
| C12R 1/07 | (2006.01) |

(52) U.S. Cl.
CPC ............... *C12N 1/20* (2013.01); *A01N 63/00* (2013.01); *A01N 63/30* (2020.01); *C12M 23/34* (2013.01); *C12Q 1/02* (2013.01); *C12R 1/07* (2013.01)

(58) Field of Classification Search
CPC ....................................................... A01N 63/00
See application file for complete search history.

(56) References Cited

PUBLICATIONS

Wenzel et al., Plant and Soil, 2001, 237:37-45.*
Aufrecht, J. A., Ryan, J. M., Hasim, S., Allison, D. P., Nebenführ, A., Doktycz, M. J., Retterer, S. T. "Imaging the Root Hair Morphology of *Arabidopsis* Seedlings in a Two-layer Microfluidic Platform." J. Vis. Exp. (126), (2017).
Busby, P. E., et al. "Research priorities for harnessing plant microbiomes in sustainable agriculture." PLOS Biology. 15, (3), e2001793 (2017).
Busch, W., et al. "A microfluidic device and computational platform for high-throughput live imaging of gene expression." Nat Methods. 9, (11), 1101-1106 (2012).
Dubey, R. K., Tripathi, V., Dubey, P. K., Singh, H. B., Abhilash, P. C. "Exploring rhizospheric interactions for agricultural sustainability: the need of integrative research on multi-trophic interactions." J Clean Prod. 115, 362-365 (2016).
Farrar, K., Bryant, D., Cope-Selby, N. "Understanding and engineering beneficial plant-microbe interactions: plant growth promotion in energy crops." Plant Biotechnol J. 12, (9), 1193-1206 (2014).
Finkel, O. M., Castrillo, G., Herrera Paredes, S., Salas González, I., Dangl, J. L. "Understanding and exploiting plant beneficial microbes." Curr Opin Plant Biol. 38, 155-163 (2017).
Friend, J., Yeo, L. "Fabrication of microfluidic devices using polydimethylsiloxane. Biomicrofluidics." 4, (2), 026502 (2010).
Gao, J., de Raad, M., Bowen, B. P., Zuckermann, R. N., Northen, T. R. "Application of Black Silicon for Nanostructure-Initiator Mass Spectrometry." Anal. Chem. 88, (3), 1625-1630 (2016).
Gao, J., et al. "Morphology-Driven Control of Metabolite Selectivity Using Nanostructure-Initiator Mass Spectrometry". Anal. Chem. 89, (12), 6521-6526 (2017).
Gao, J., et al., "Ecosystem Fabrication (EcoFAB) Protocols for the Construction of Laboratory Ecosystems Designed to Study Plant-microbe Interactions" J. Vis. Exp. (134), e57170, doi:10.3791/57170 (2018).
Garvin, D. F., et al. "Development of Genetic and Genomic Research Resources for Brachypodium distachyon, a New Model System for Grass Crop Research." Crop Sci. 48, (Supplement_1), S69-S84 (2008).
Grossmann, G., et al. "The RootChip: An Integrated Microfluidic Chip for Plant Science." Plant Cell. 23, (12), 4234-4240 (2011).
Hunter, P. "Plant microbiomes and sustainable agriculture." EMBO Rep. 17, (12), 1696-1699 (2016).
Jiang, H., Xu, Z., Aluru, M. R., Dong, L. "Plant chip for high-throughput phenotyping of *Arabidopsis*." Lab Chip. 14, (7), 1281-1293 (2014).
Kamilova, F., Validov, S., Azarova, T., Mulders, I., Lugtenberg, B. "Enrichment for enhanced competitive plant root tip colonizers selects for a new class of biocontrol bacteria." Environ. Microbiol. 7, (11), 1809-1817 (2005).
Klitgaard, A., Nielsen, J. B., Frandsen, R. J. N., Andersen, M. R., Nielsen, K. F. "Combining Stable Isotope Labeling and Molecular Networking for Biosynthetic Pathway Characterization." Anal. Chem. 87, (13), 6520-6526 (2015).
Lisensky, G. C., et al. "Replication and Compression of Surface Structures with Polydimethylsiloxane Elastomer." J. Chem. Educ. 76, (4), 537 (1999).
López-Bucio, J., Cruz-Ramírez, A., Herrera-Estrella, L. "The role of nutrient availability in regulating root architecture." Curr Opin Plant Biol. 6, (3), 280-287 (2003).
Lynch, J. P. "Steep, cheap and deep: an ideotype to optimize water and N acquisition by maize root systems." Ann. Bot. 112, (2), 347-357 (2013).
Massalha, H., Korenblum, E., Malitsky, S., Shapiro, O. H., Aharoni, A. "Live imaging of root-bacteria interactions in a microfluidics setup." P Natl. Acad. Sci. USA. 114, (17), 4549-4554 (2017).
Morrissey, J. P., Dow, J. M., Mark, G. L., O'Gara, F. "Are microbes at the root of a solution to world food production". EMBO Rep. 5, (10), 922-926 (2004).

(Continued)

*Primary Examiner* — Bin Shen
(74) *Attorney, Agent, or Firm* — Sheppard, Mullin, Richter & Hampton LLP

(57) ABSTRACT

Disclosed herein are systems, methods, and devices for determining plant-microbe interactions. In some embodiments, the device comprises: a root chamber configured to allow a root of a plant to grow, wherein the root chamber is connected with: an inlet channel for introducing a medium into the root chamber, an outlet channel for collecting plant exudates and metabolites, and a plant reservoir for the plant shoot of the plant to grow.

25 Claims, 44 Drawing Sheets

(56) References Cited

PUBLICATIONS

Northen, T. R., Zhang, Z., Gao, J., Swenson, T., Yoshikuni, Y. "Advancing Our Understanding of the Chemistry of Soil Microbiomes. National Academies of Sciences, Engineering, and Medicine." The Chemistry of Microbiomes: Proceedings of a Seminar Series. The National Academies Press. Washington, DC. (2017).

Oburger, E., et al. "Evaluation of a novel tool for sampling root exudates from soil-grown plants compared to conventional techniques." Environ Exp Bot. 87, 235-247 (2013).

Parashar, A., Pandey, S. "Plant-in-chip: Microfluidic system for studying root growth and pathogenic interactions in *Arabidopsis*." Appl. Phys. Lett. 98, (26), 263703 (2011).

Rellán-Álvarez, R., et al. "GLO-Roots: an imaging platform enabling multidimensional characterization of soil-grown root systems." eLife. 4, e07597 (2015).

Reynolds, H. L., Packer, A., Bever, J. D., Clay, K. "Grassroots Ecology: Plant-Microbe-Soil Interactions as Drivers of Plant Community Structure and Dynamics." Ecology. 84, (9), 2281-2291 (2003).

Rübel, O., et al. "OpenMSI: A High-Performance Web-Based Platform for Mass Spectrometry Imaging." Anal. Chem. 85, (21), 10354-10361 (2013).

Sanati Nezhad, A. "Microfluidic platforms for plant cells studies." Lab Chip. 14, (17), 3262-3274 (2014).

Sanati Nezhad, A., Naghavi, M., Packirisamy, M., Bhat, R., Geitmann, A. "Quantification of cellular penetrative forces using lab-on-a-chip technology and finite element modeling." P Natl. Acad. Sci. USA. 110, (20), 8093-8098 (2013).

Singh, J. S., Abhilash, P. C., Gupta, V. K. "Agriculturally Important Microbes in Sustainable Food Production." Trends Biotechnol. 34, (10), 773-775 (2016).

Sumner, L. W., et al. "Proposed minimum reporting standards for chemical analysis Chemical Analysis Working Group (CAWG) Metabolomics Standards Initiative (MSI)." Metabolomics. 3, (3), 211-221 (2007).

Van der Heijden, M. G. A., Hartmann, M. "Networking in the Plant Microbiome." PLoS Biol. 14, (2), e1002378 (2016).

Van Der Krift, T. A. J., Berendse, F. "Root life spans of four grass species from habitats differing in nutrient availability". Funct Ecol. 16, (2), 198-203 (2002).

Vessey, J. K. "Plant growth promoting rhizobacteria as biofertilizers." Plant Soil. 255, (2), 571-586 (2003).

Woo, H.K., Northen, T. R., Yanes, O., Siuzdak, G. "Nanostructure-initiator mass spectrometry: a protocol for preparing and applying NIMS surfaces for high-sensitivity mass analysis." Nat. Protoc. 3, (8), 1341-1349 (2008).

Yang, J., Kloepper, J. W., Ryu, C.M. "Rhizosphere bacteria help plants tolerate abiotic stress." Trends Plant Sci. 14, (1), 1-4 (2009).

Yao, Y., et al. "Analysis of Metabolomics Datasets with High-Performance Computing and Metabolite Atlases." Metabolites. 5, (3), 431-442 (2015).

\* cited by examiner

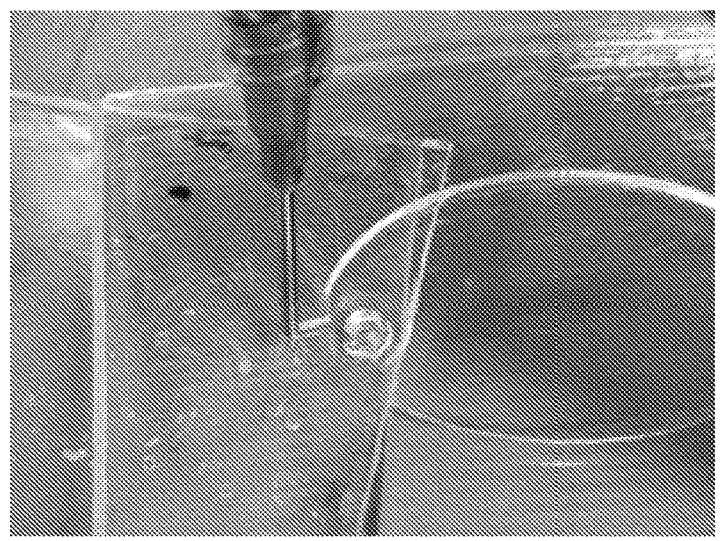
FIG. 3A1
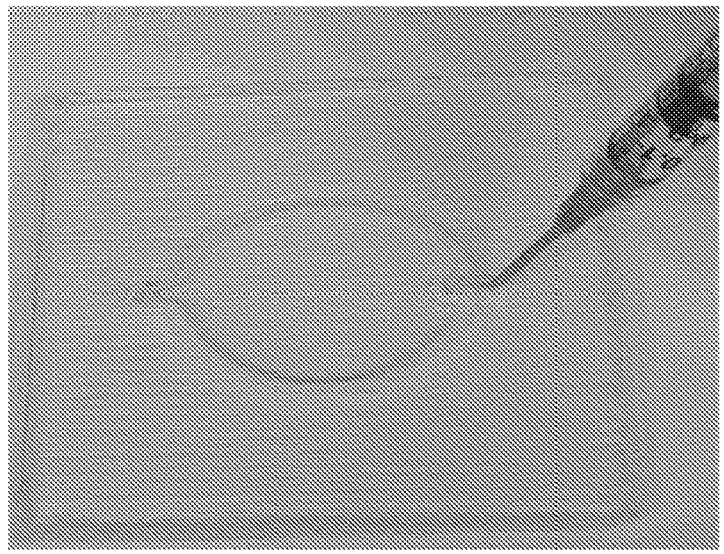
FIG. 3A2
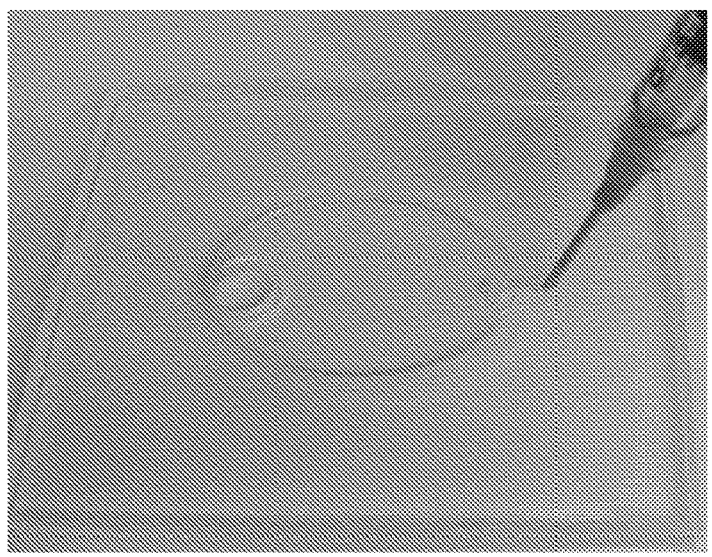
FIG. 3A3

FIG. 3B1
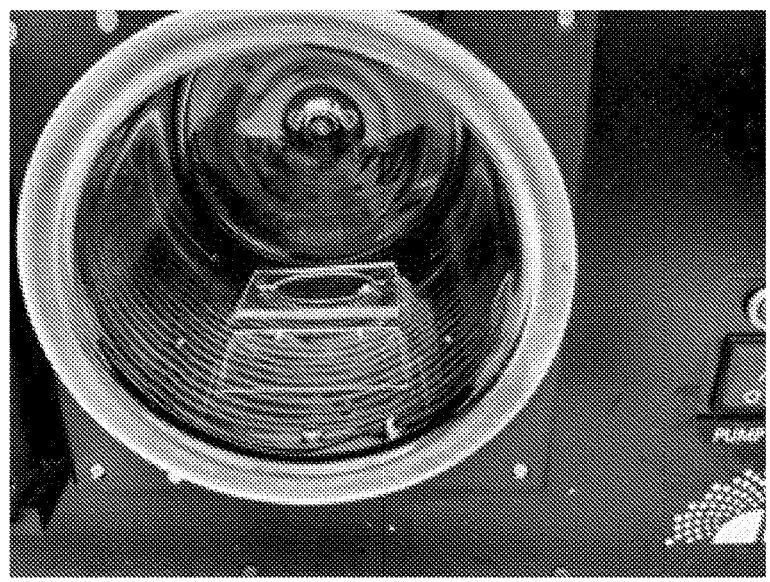
FIG. 3B2
FIG. 3C
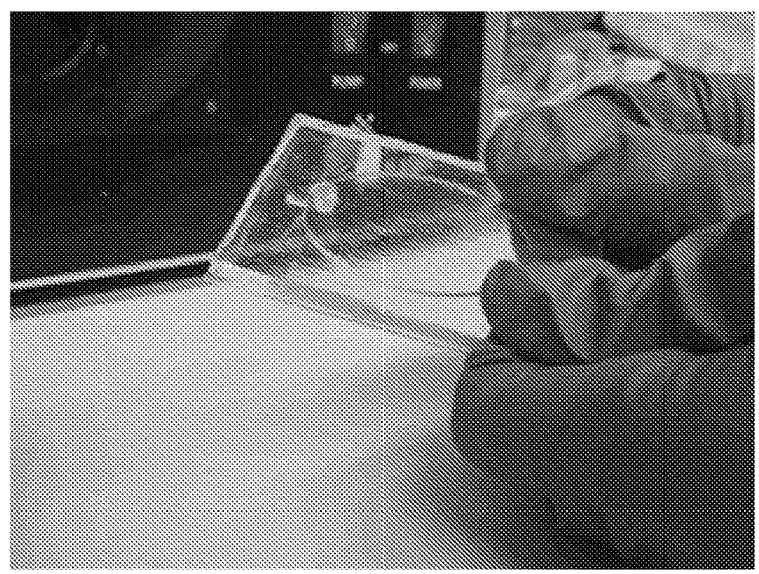

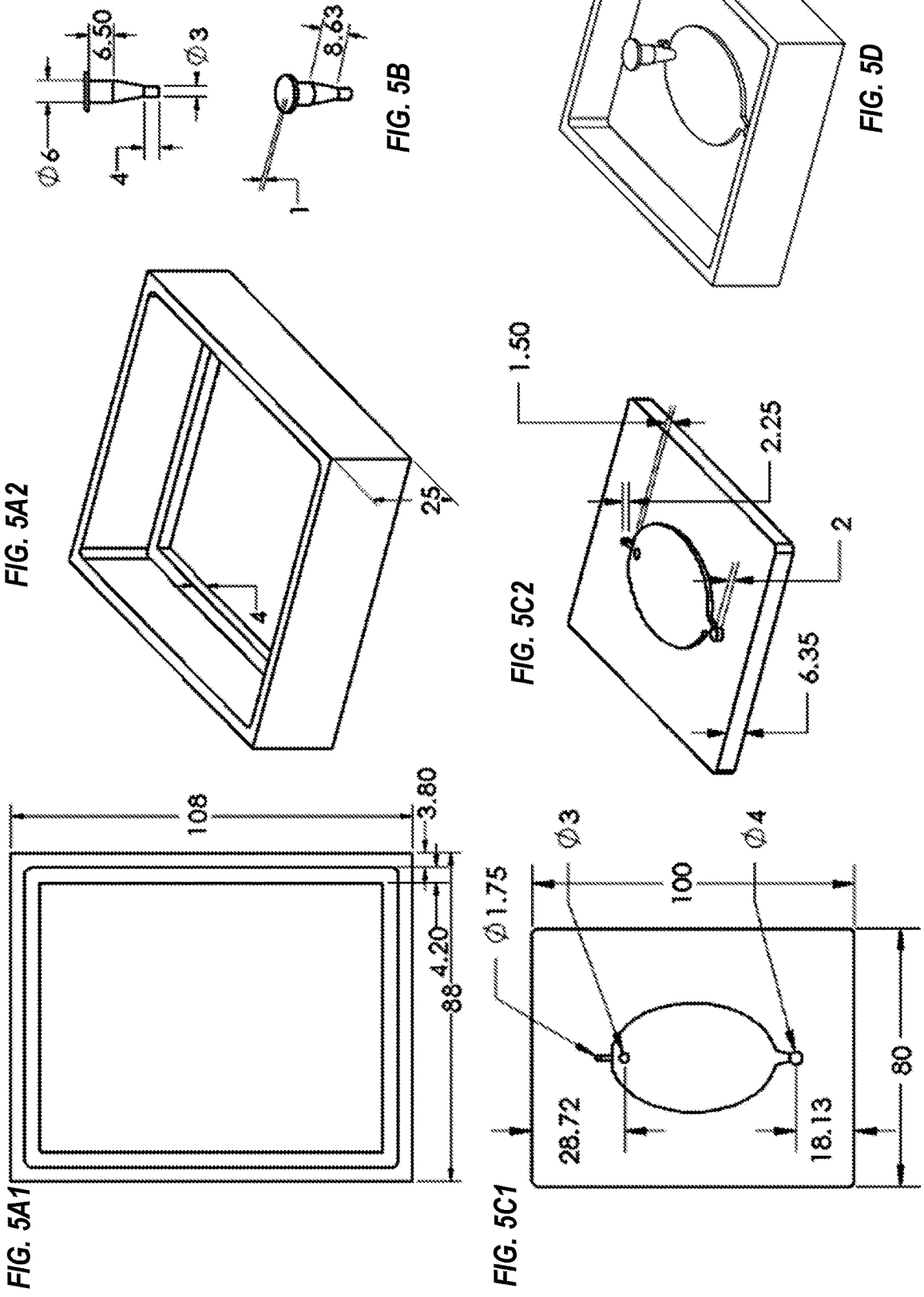

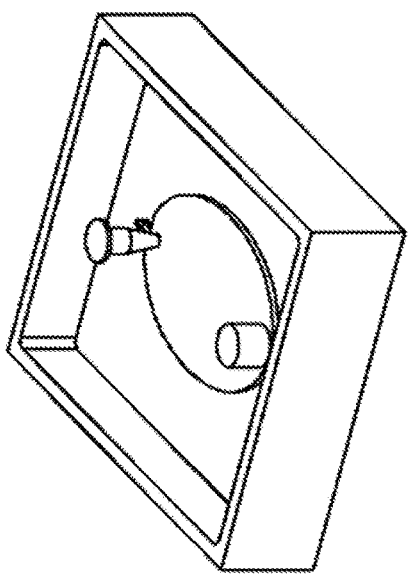
FIG. 5F
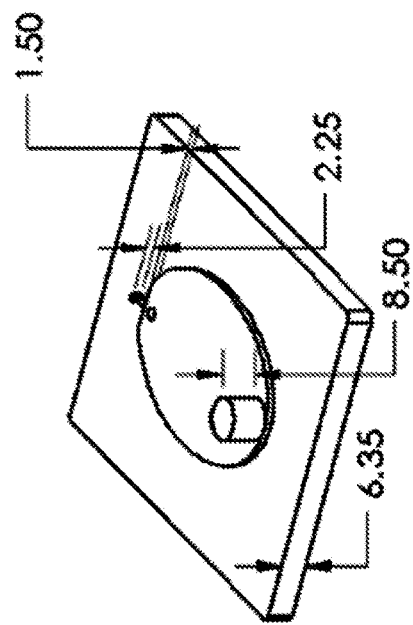
FIG. 5E2
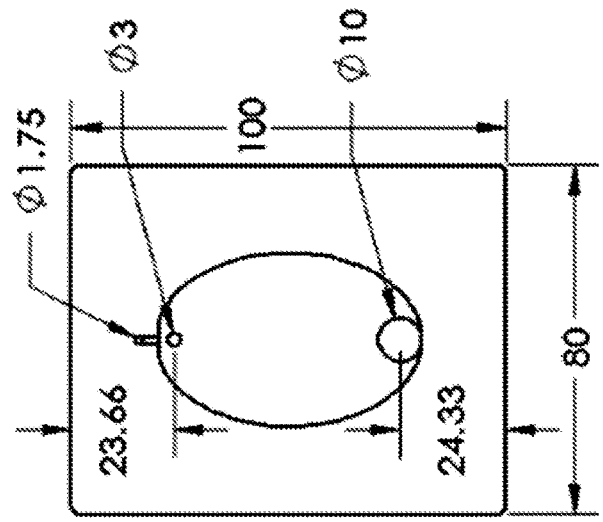
FIG. 5E1

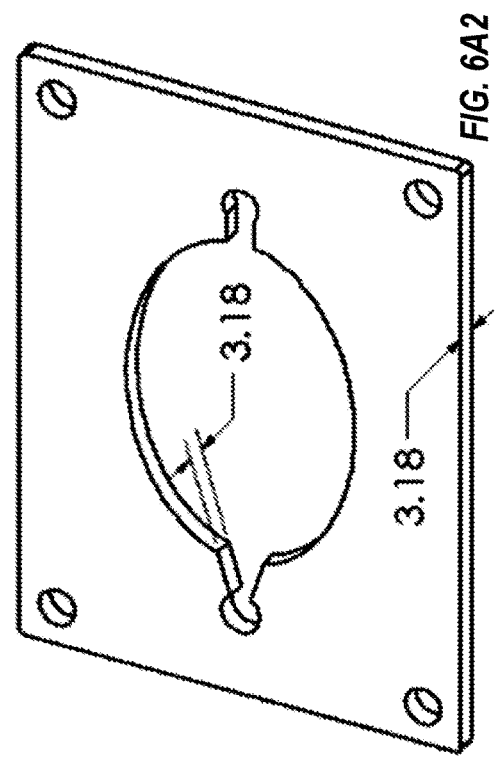
FIG. 6A2
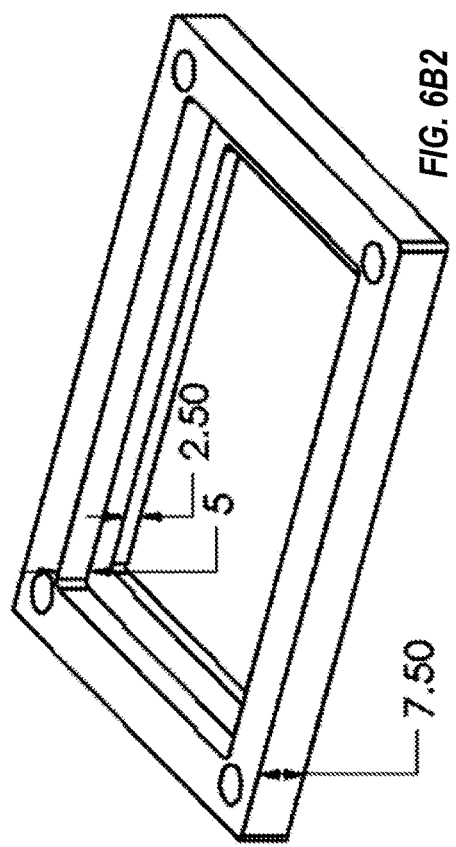
FIG. 6B2
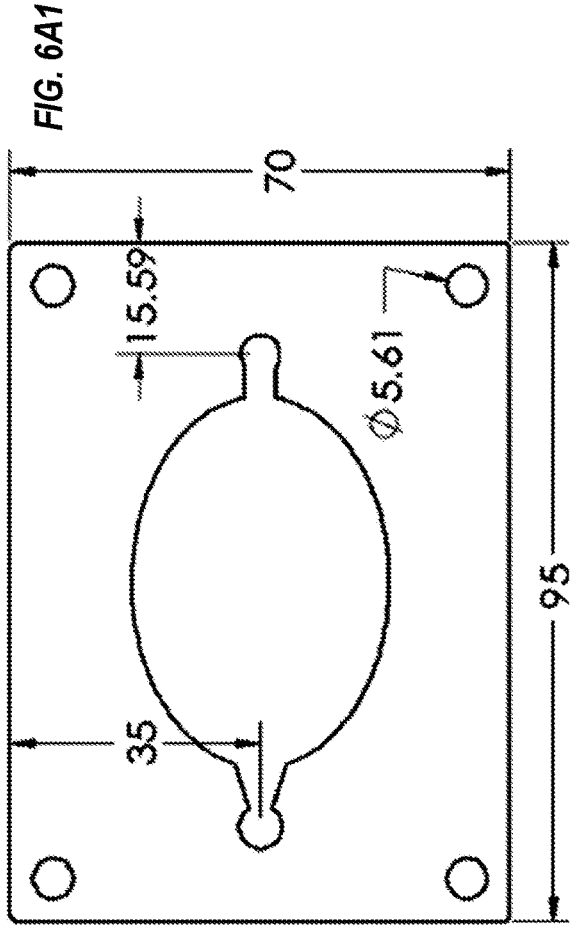
FIG. 6A1
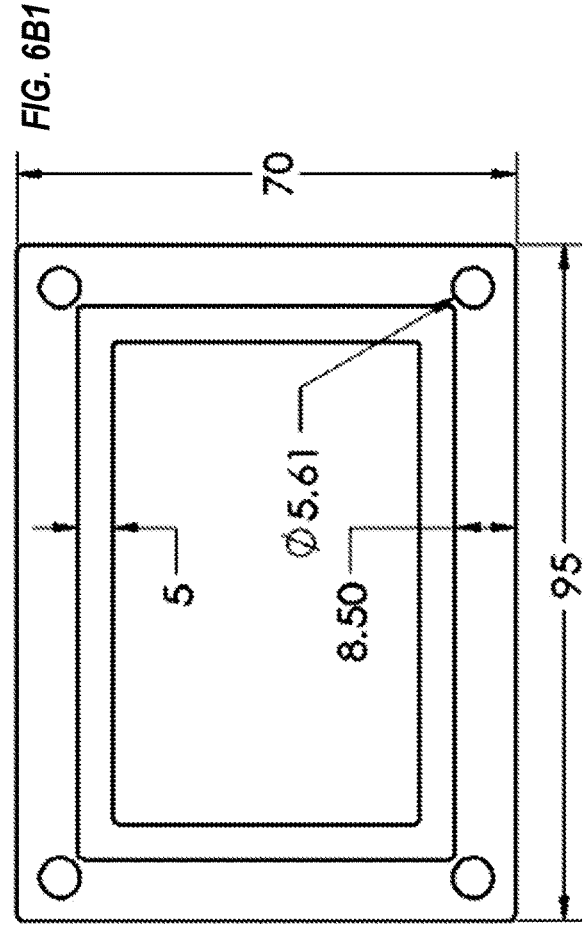
FIG. 6B1

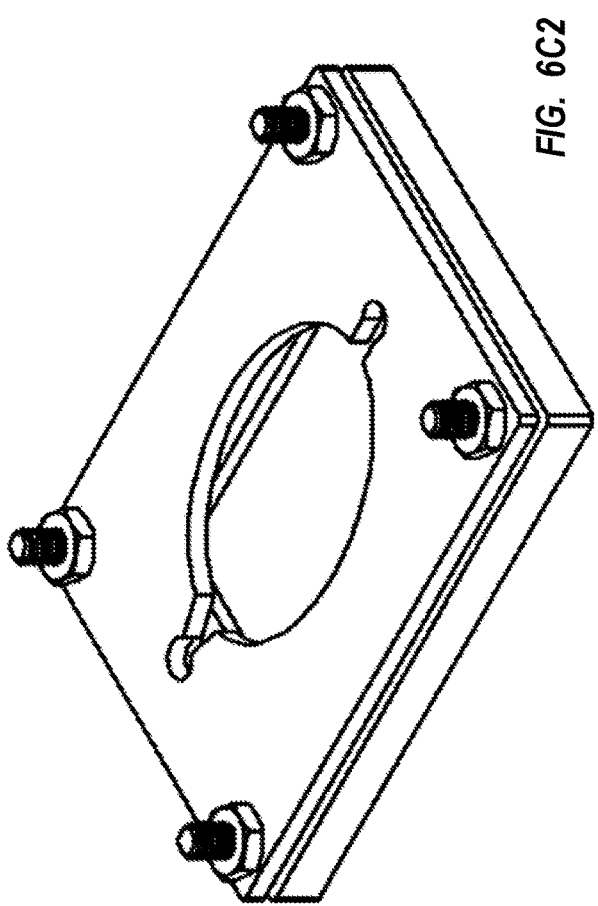
FIG. 6C2
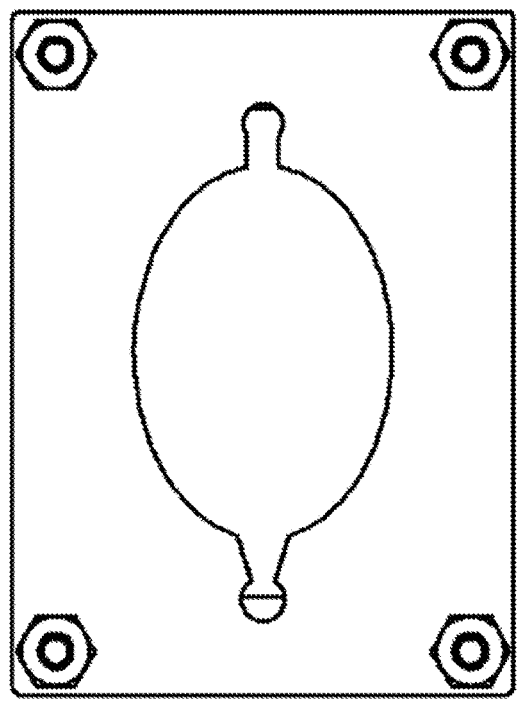
FIG. 6C1

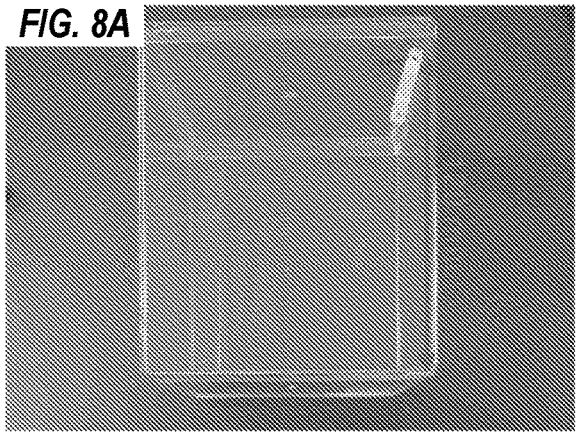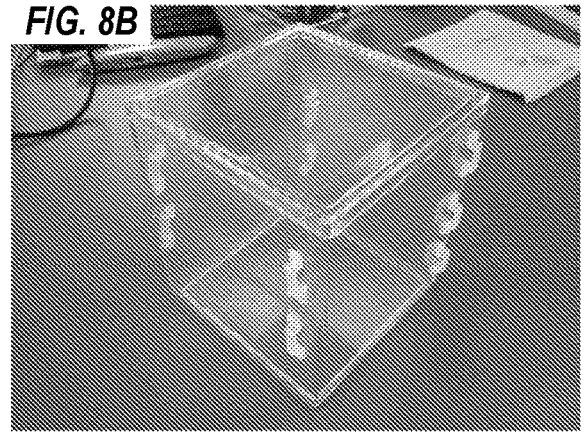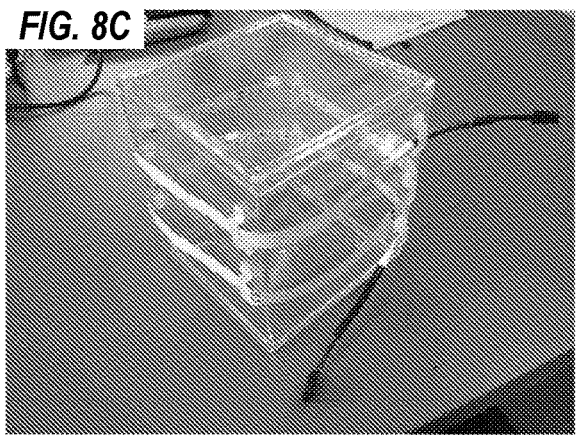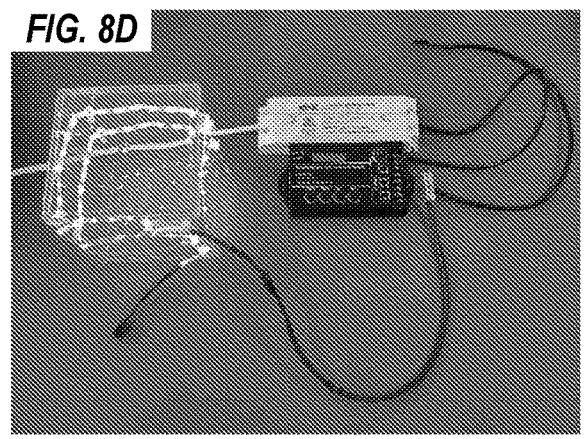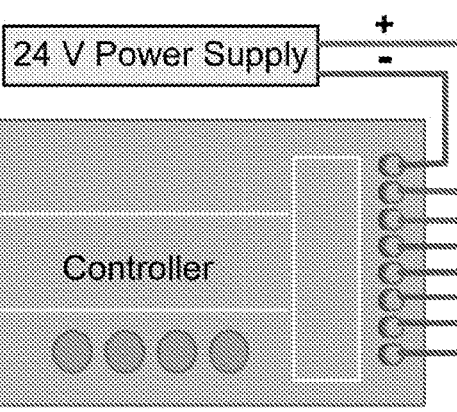

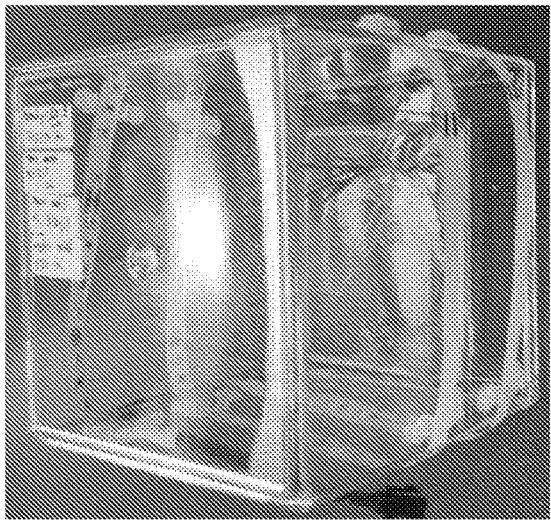
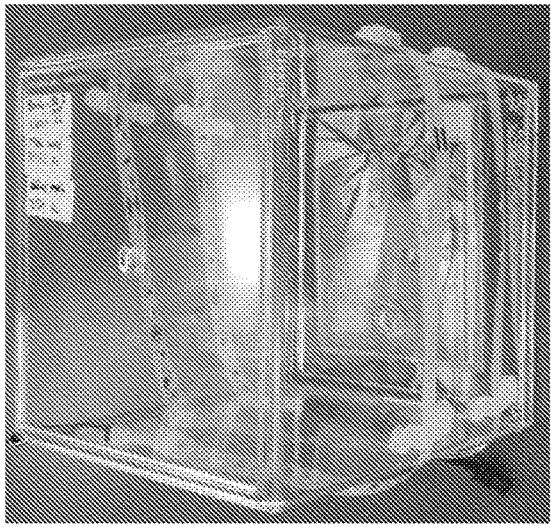
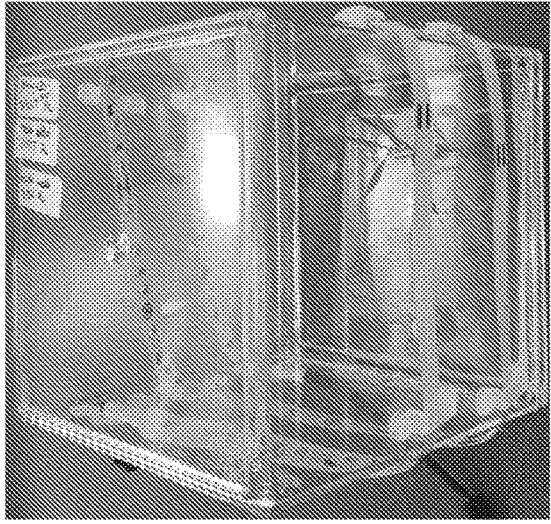
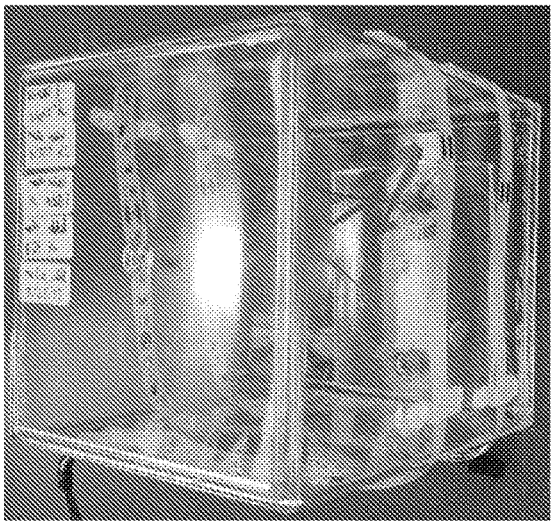
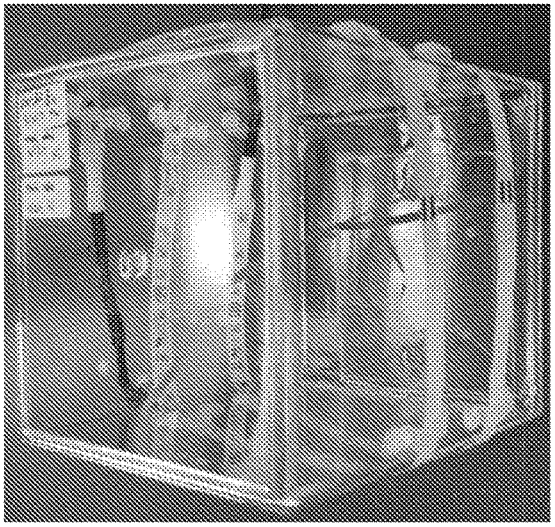
FIG. 9A  FIG. 9B  FIG. 9C  FIG. 9D  FIG. 9E  FIG. 9F

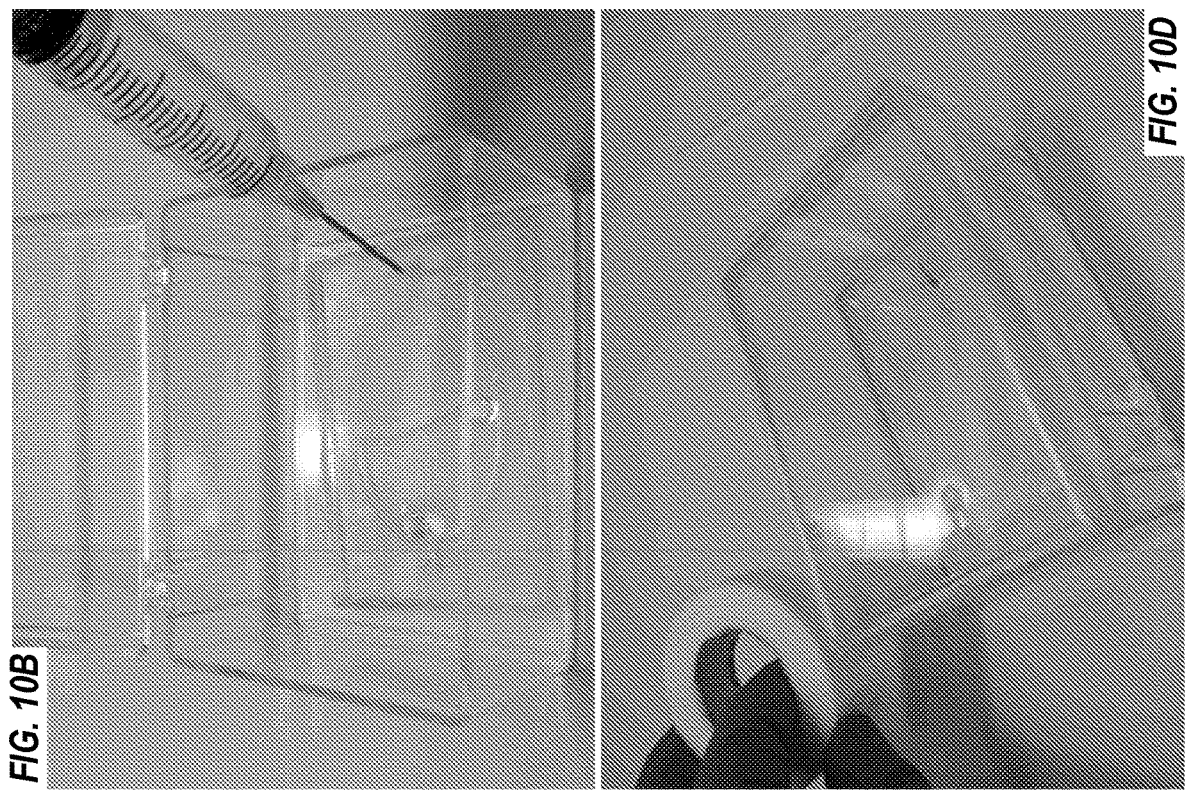
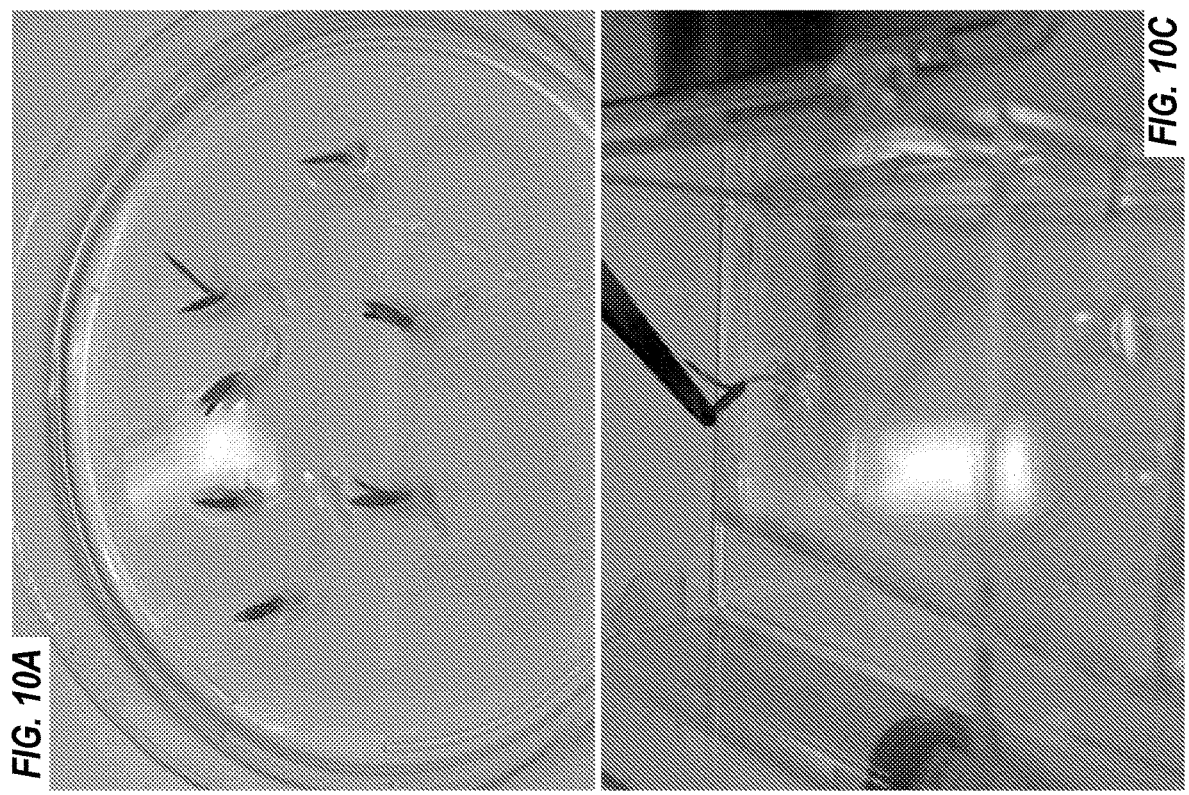

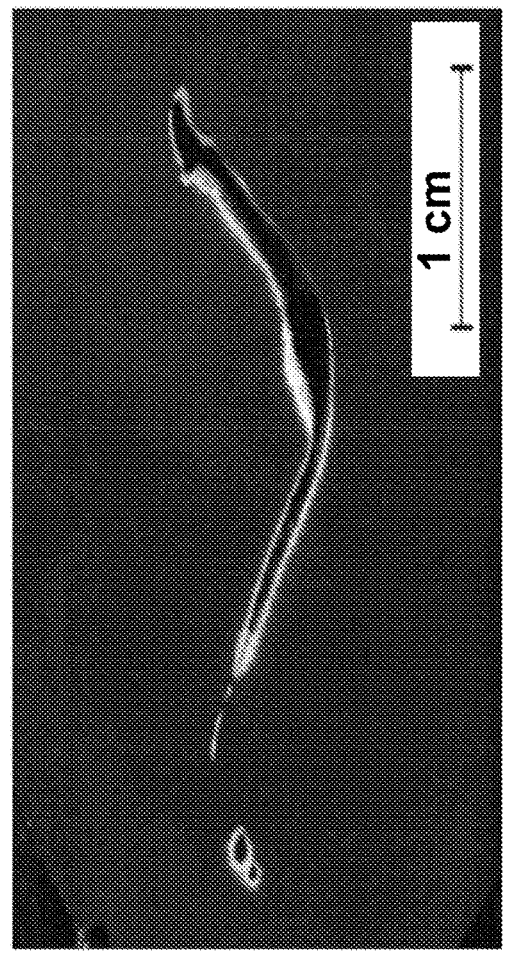
FIG. 12D
FIG. 12E
- m/z 184.00
- m/z 326.16
- m/z 496.13

● m/z 147.02
● m/z 184.00
● m/z 651.01

● m/z 326.30
● m/z 496.26
● m/z 611.25

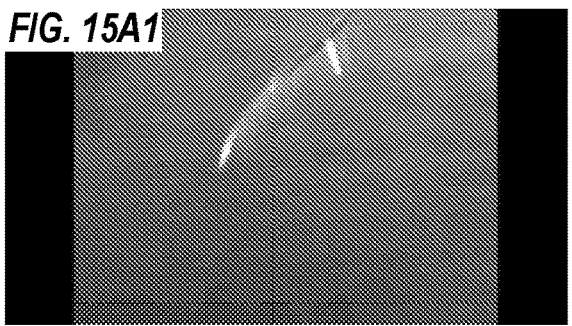
FIG. 15A1
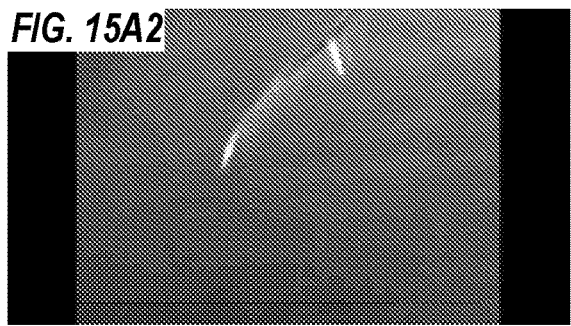
FIG. 15A2
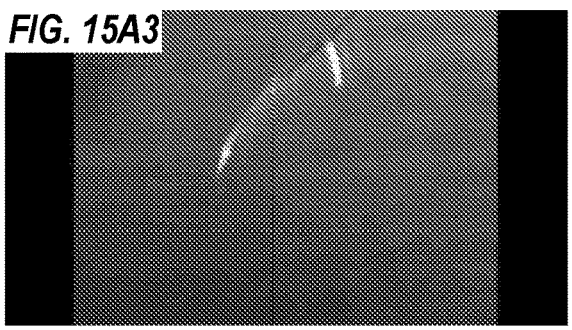
FIG. 15A3
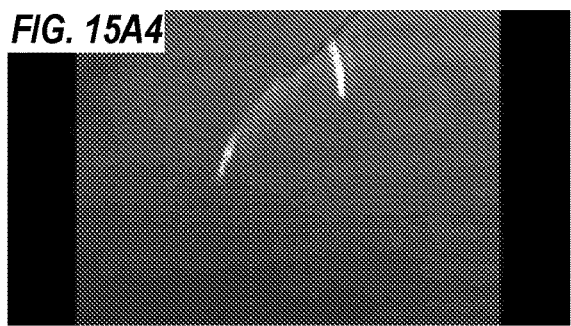
FIG. 15A4
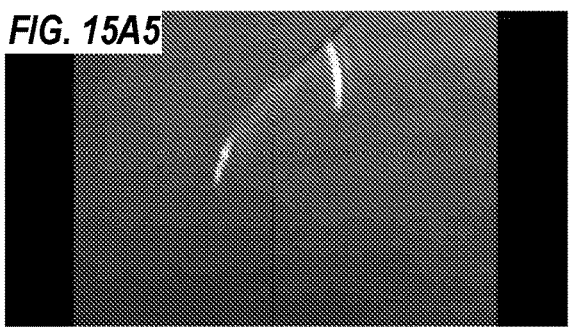
FIG. 15A5
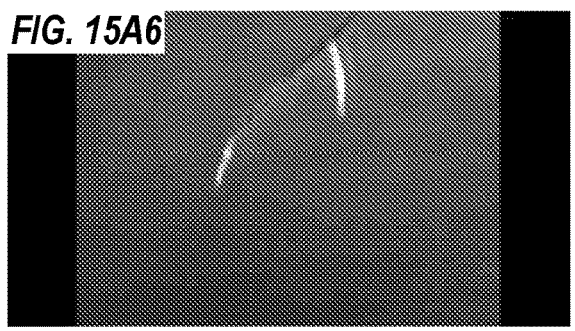
FIG. 15A6
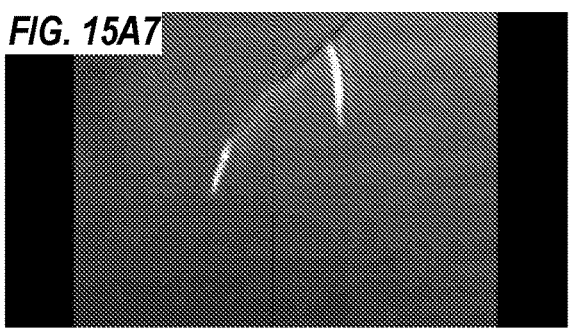
FIG. 15A7
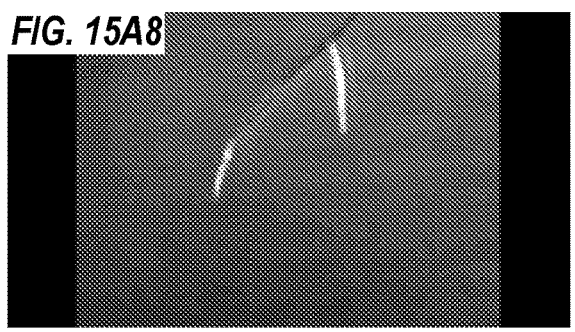
FIG. 15A8
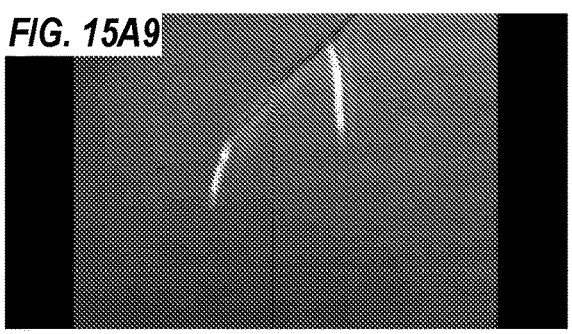
FIG. 15A9
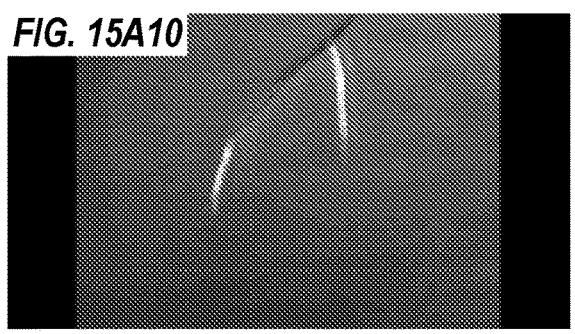
FIG. 15A10

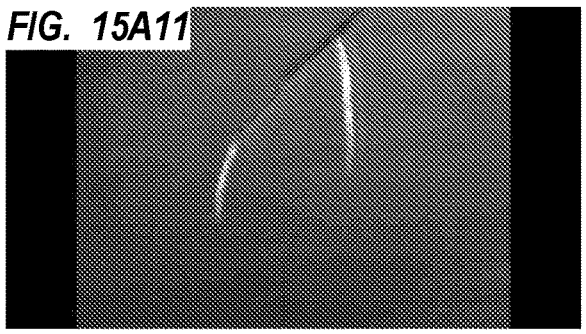
FIG. 15A11
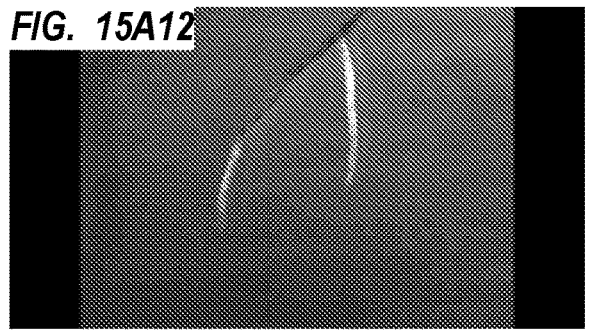
FIG. 15A12
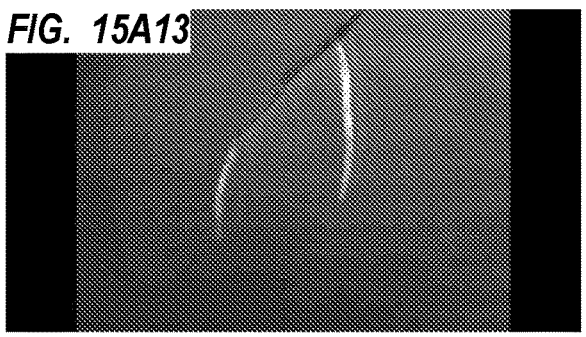
FIG. 15A13
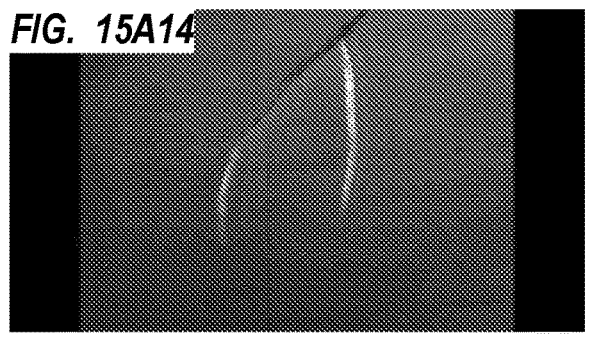
FIG. 15A14
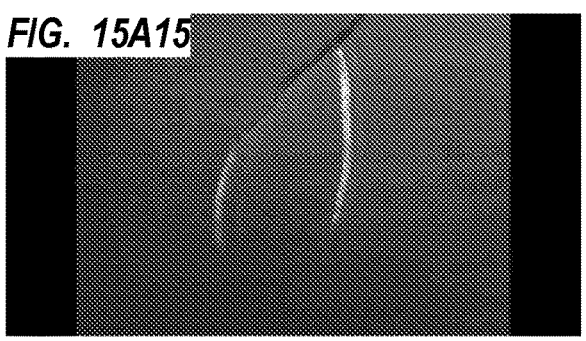
FIG. 15A15
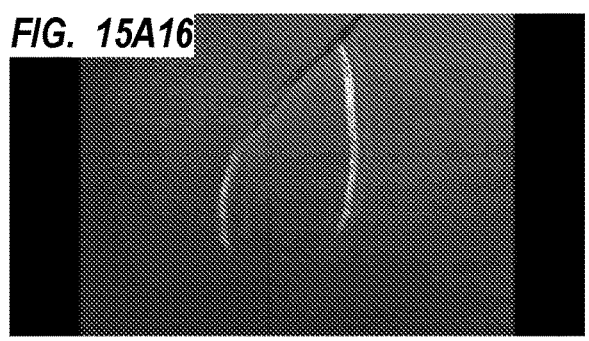
FIG. 15A16
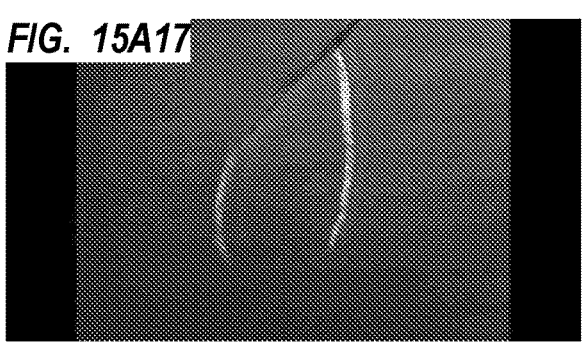
FIG. 15A17
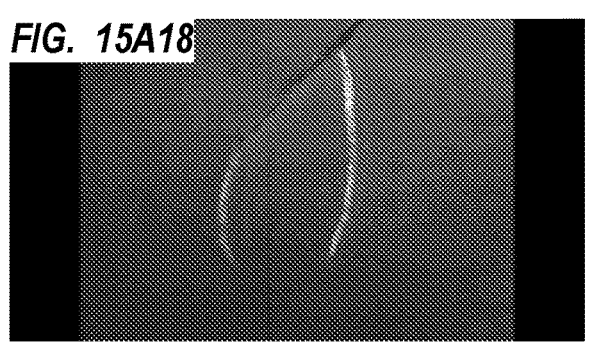
FIG. 15A18

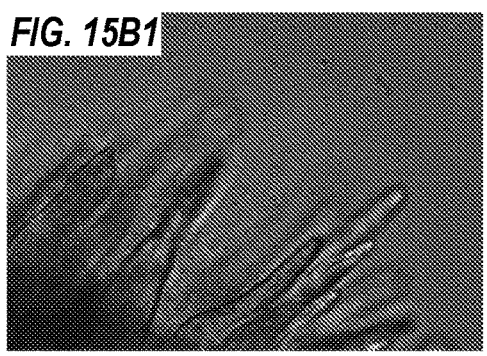
FIG. 15B1
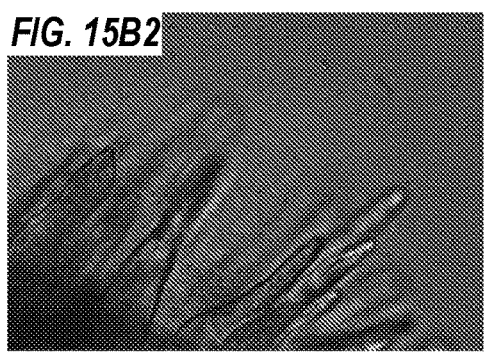
FIG. 15B2
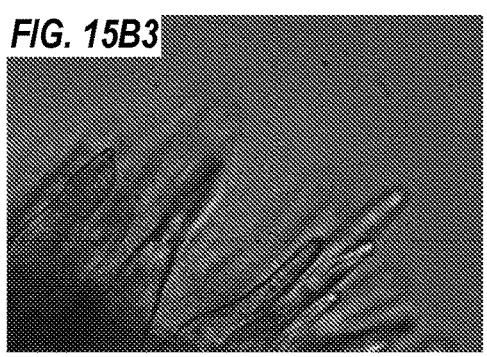
FIG. 15B3
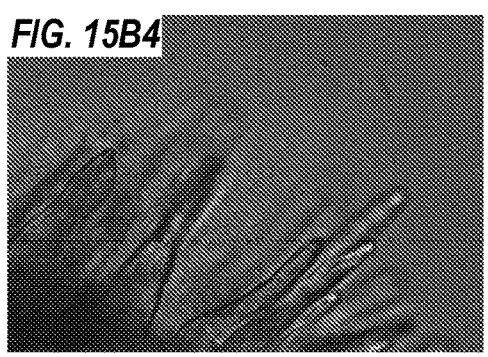
FIG. 15B4
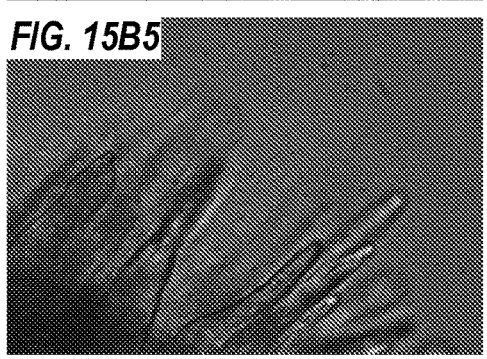
FIG. 15B5
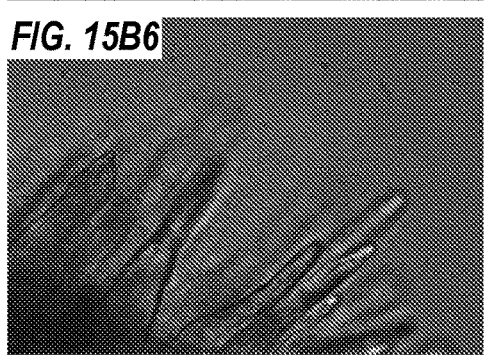
FIG. 15B6
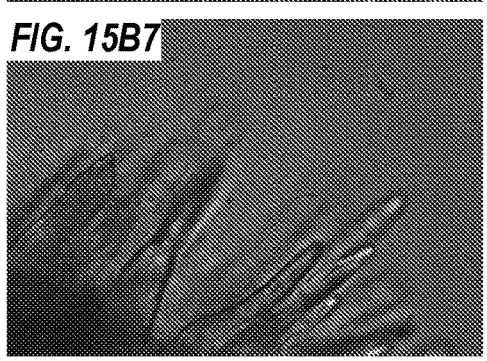
FIG. 15B7
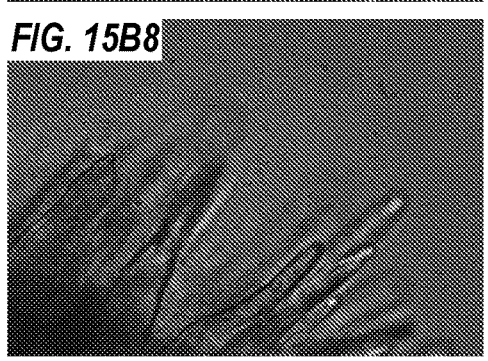
FIG. 15B8
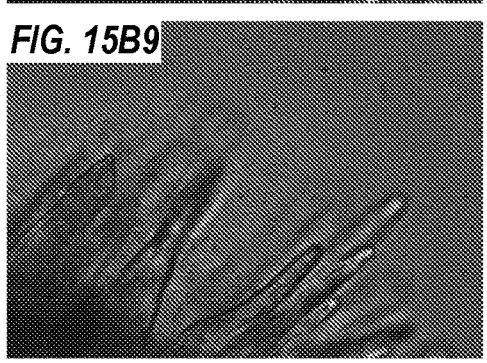
FIG. 15B9
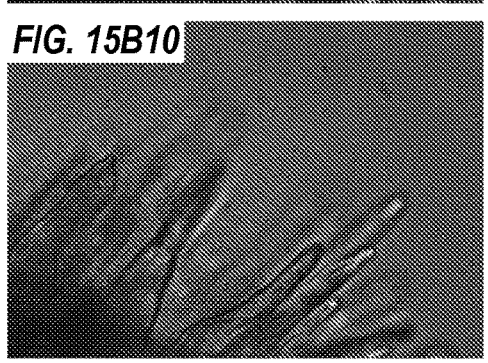
FIG. 15B10

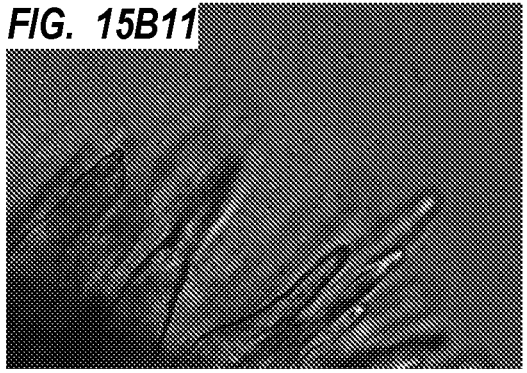
FIG. 15B11
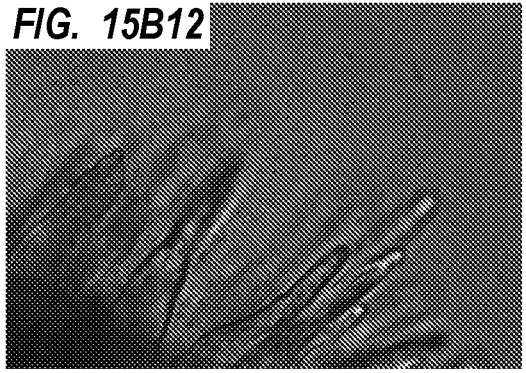
FIG. 15B12
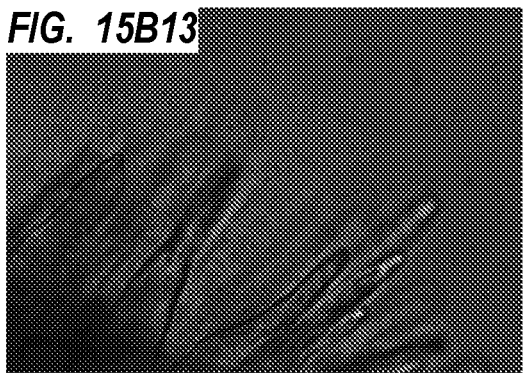
FIG. 15B13
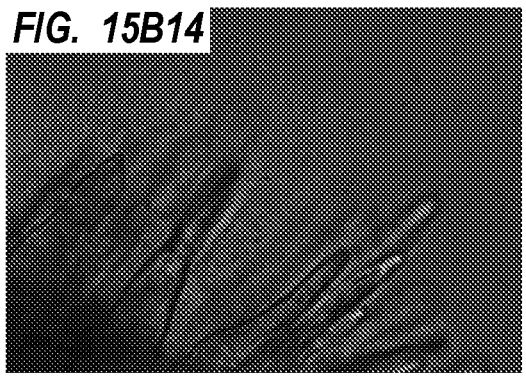
FIG. 15B14
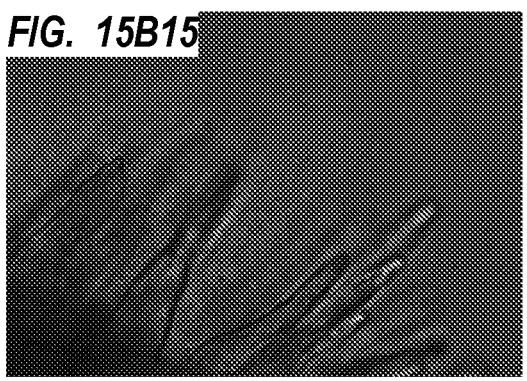
FIG. 15B15
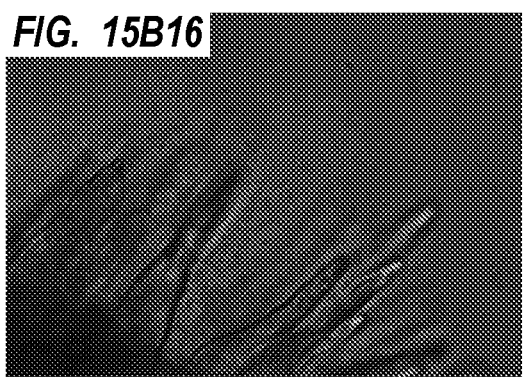
FIG. 15B16
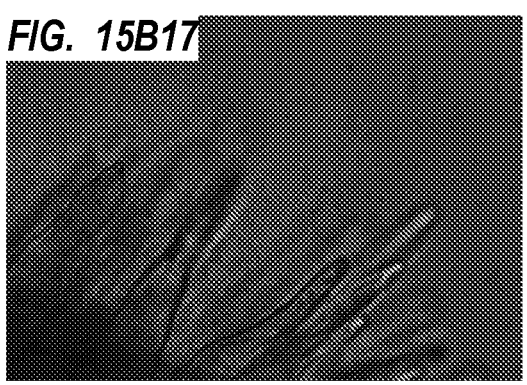
FIG. 15B17

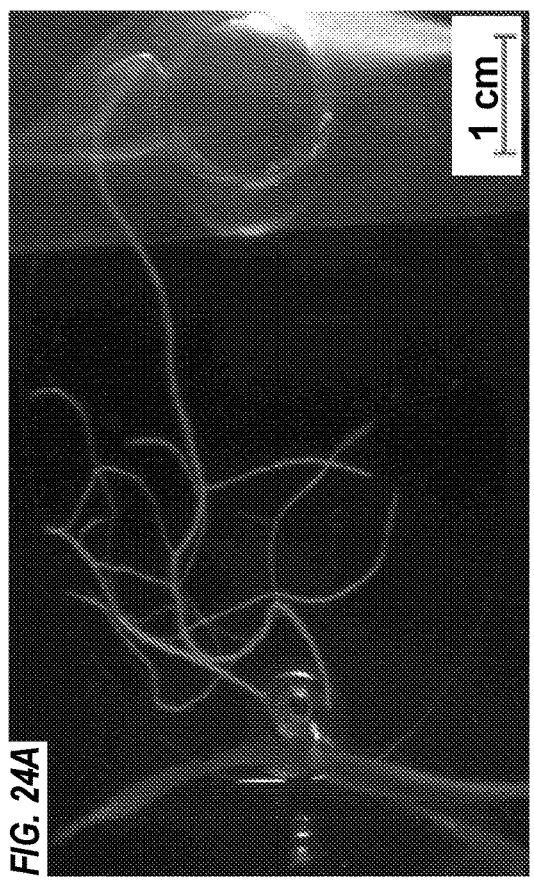
FIG. 24A
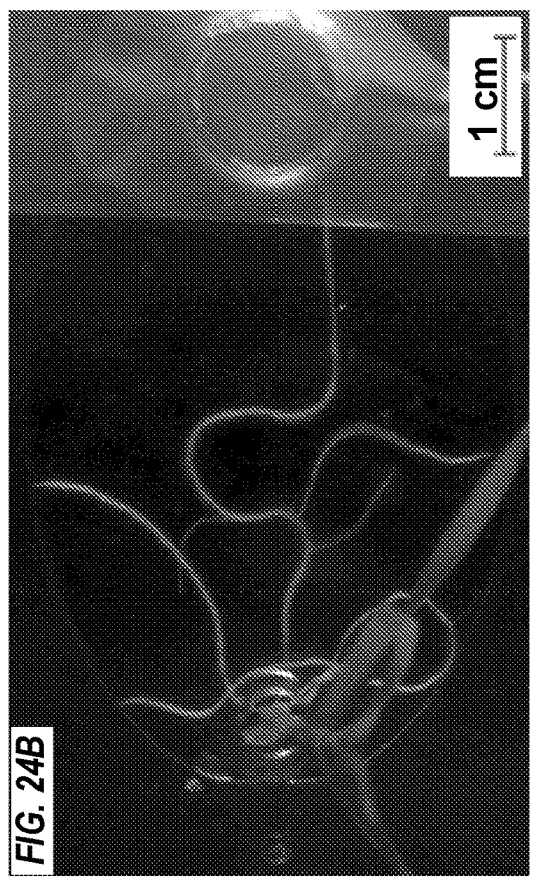
FIG. 24B
FIG. 24C
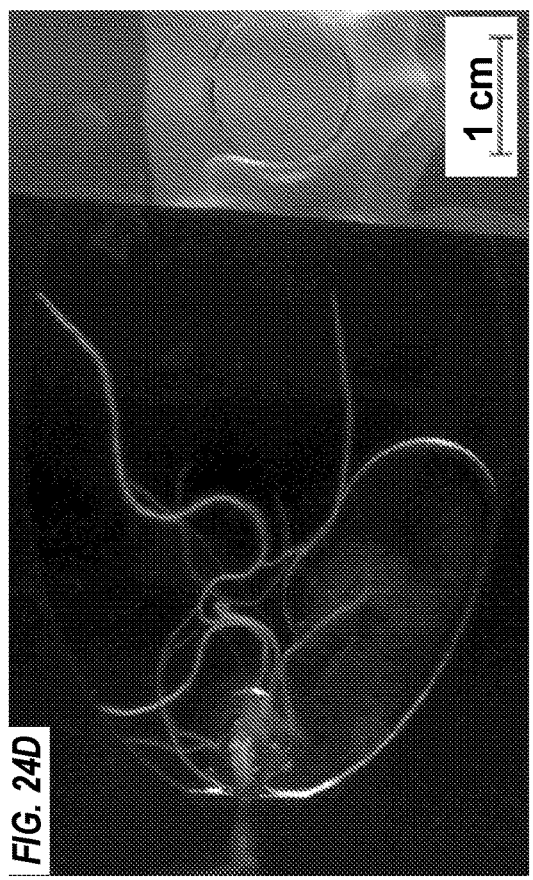
FIG. 24D
FIG. 24

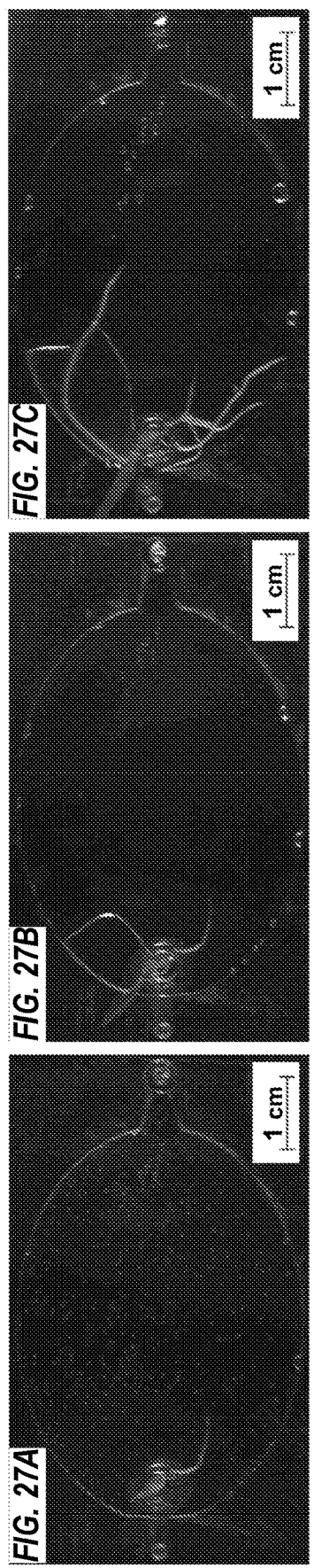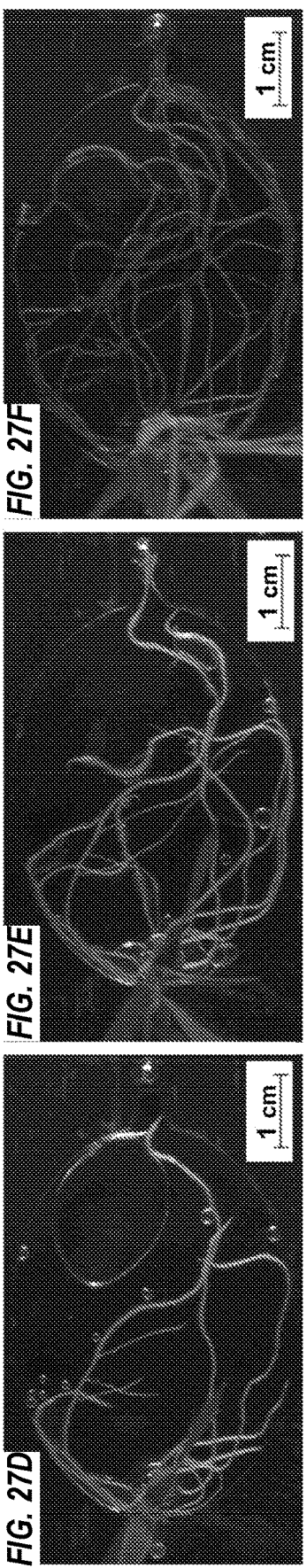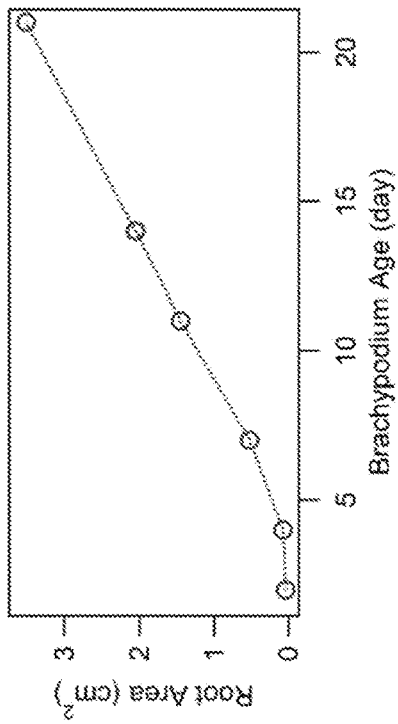
FIG. 27A  FIG. 27B  FIG. 27C
FIG. 27D  FIG. 27E  FIG. 27F
FIG. 27G

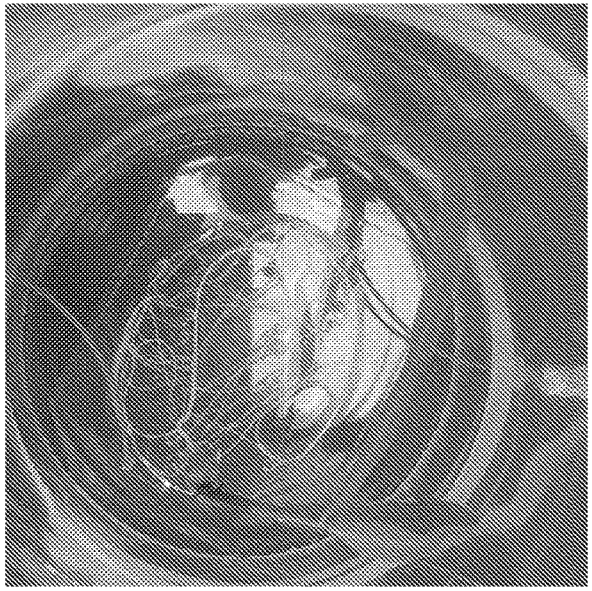
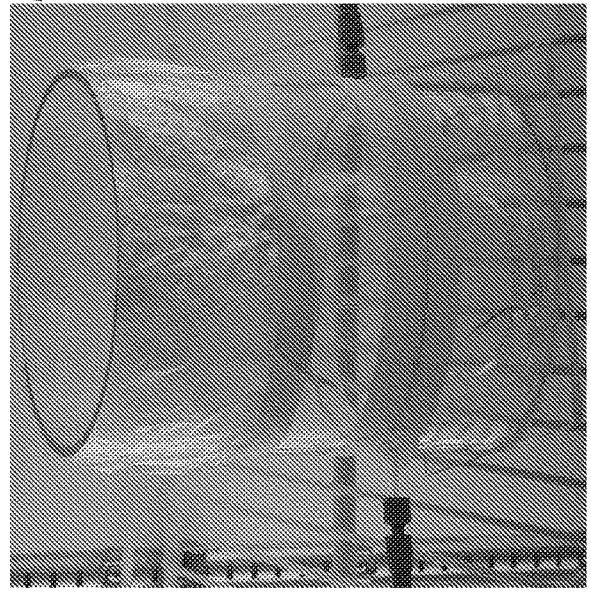
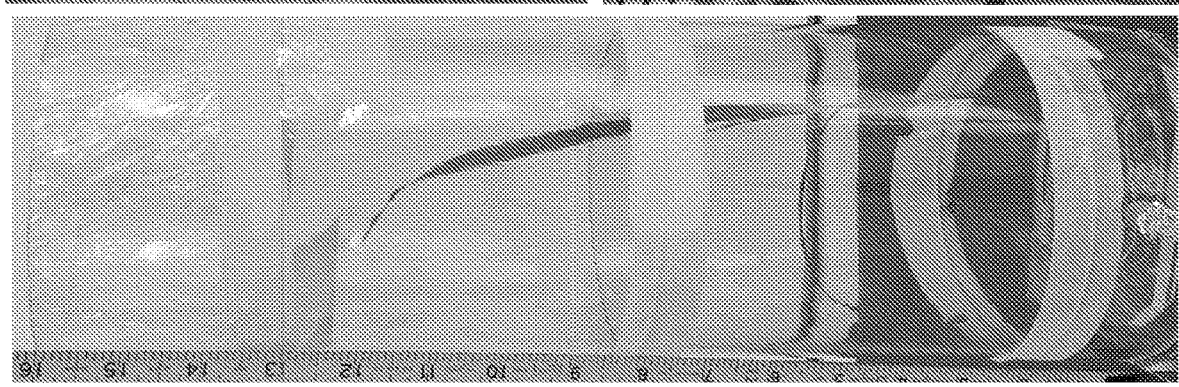
FIG. 29A
FIG. 29B
FIG. 29C

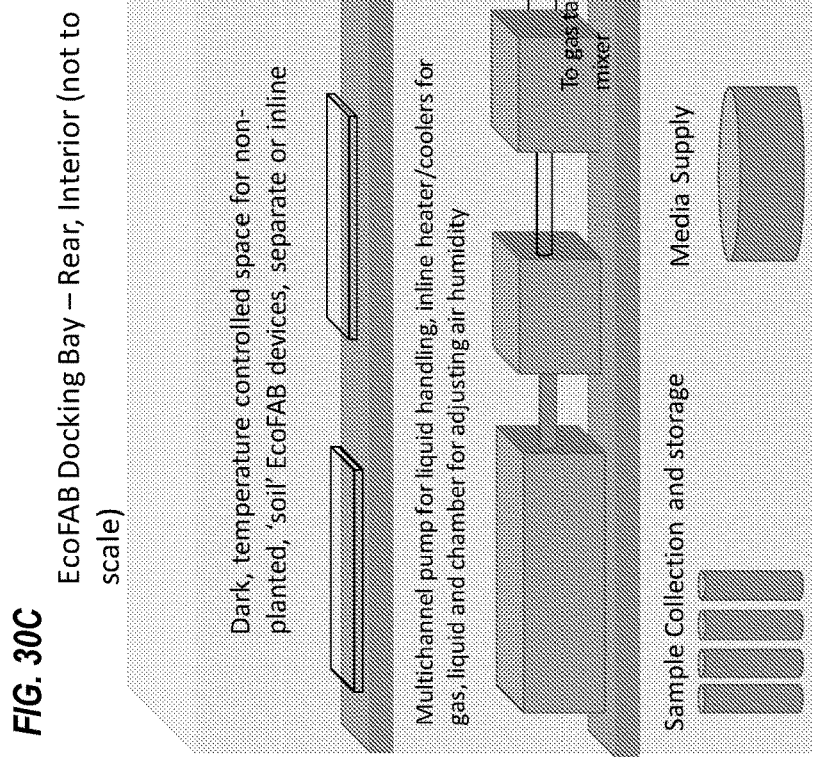
FIG. 30C
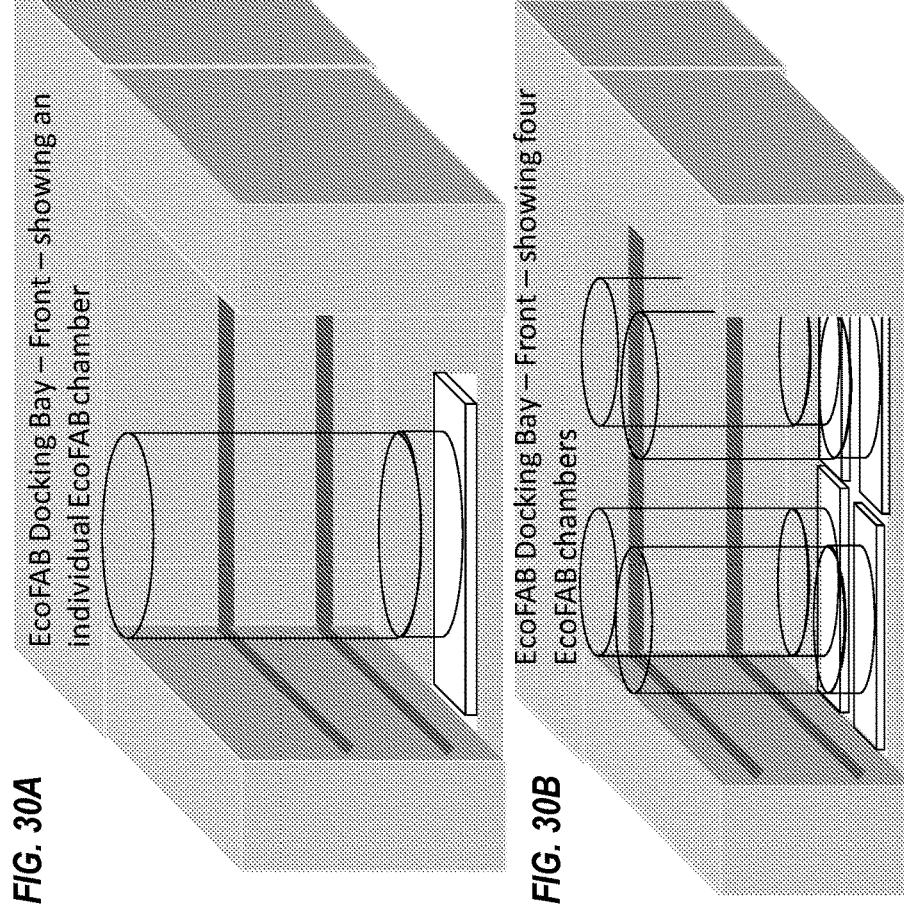
FIG. 30A
FIG. 30B

ECOSYSTEM FOR DETERMINING PLANT-MICROBE INTERACTIONS

RELATED APPLICATIONS

The present application claims priority under 35 U.S.C. § 119(e) to U.S. Provisional Application No. 62/490,548, filed on Apr. 26, 2017. The content of this related application is incorporated herein by reference in its entirety.

STATEMENT REGARDING FEDERALLY SPONSORED R&D

This invention was made with government support under grant no. DE-AC02-05CH11231 awarded by the U.S. Department of Energy. The government has certain rights in the invention.

BACKGROUND

Field

The present disclosure relates generally to the field of determining ecological processes, and more particularly to determining plant-microbe interactions.

Description of the Related Art

Microbiomes play essential roles in every aspects of life on Earth, and environmental microbial communities can largely govern the carbon cycles and food production. Methods and techniques focus on studying individual isolates or complex field communities. However, vital understanding of the plant-microbe-soil interactions in rhizosphere is lacking. Thus, there is a need for systems and methods for constructing consortia, characterizing the constituent isolates independently, and manipulating their function genetically to study their mechanisms.

SUMMARY

Disclosed herein are systems, methods, and devices for determining plant-microbe interactions. In some embodiments, the device comprises: a root chamber configured for a root of a plant to grow, wherein the root chamber is connected with: an inlet channel for introducing a medium into the root chamber, an outlet channel for collecting plant exudates and metabolites, and a plant reservoir for the shoot of the plant to grow.

In some embodiments, the root chamber has a volume of 1-5 ml. The height of the root chamber to the diameter of the root chamber can be at least 1:5. The height of the root chamber to the diameter of the root chamber can be about 1:1. The height of the root chamber to the diameter of the root chamber can be at most 5:1. The height of the root chamber to the width of the root chamber can be at least 1:5. The height of the root chamber to the width of the root chamber can be about 1:1. The height of the root chamber to the width of the root chamber can be at most 5:1. The height of the root chamber to the depth of the root chamber can be at least 1:5. The height of the root chamber to the depth of the root chamber can be about 1:1. The height of the root chamber to the depth of the root chamber can be at most 5:1. The root chamber can be created by a cavity of a first layer and a second layer. The first layer can comprise a polydimethylsiloxane (PDMS) layer. The second layer can comprise a glass layer. The first layer can be reversibly attached to the second layer. The first layer can be permanently bond to the second layer. The inlet channel, the outlet channel, and the plant reservoir are disposed in the first layer. The device can be formed using a mold. The mold can comprise a base piece and a side piece, and wherein the base piece is reversibly attached to the side piece to form the mold. The medium can comprise one or more microorganisms. The medium can comprise a solid medium, a liquid medium, a gaseous medium, or a combination thereof. The device and/or the root chamber can be configured for vertical or placement or operation. The device and/or the root chamber can be configured for horizontal placement or operation.

In some embodiments, the device comprises an upper chamber and a lower chamber. The lower chamber can comprise a base connected to a vertical section (e.g., tube). The upper chamber can comprise a vertical section (e.g., a tube). The height of the tube can be selected based on the plant (e.g., expected height of the plant). A rubber gasket between the lower chamber and the upper chamber can form an air-tight seal between the lower chamber and the upper chamber.

In some embodiments, the system comprises: a device for determining plant-microbe interactions, and a docking station for one or more of temperature control of the device, media introduction into the device, sampling from the device, lighting of the device, imaging a plant grown in the device, and spectroscopy analysis of the plant grown in the device, wherein the plant is grown in a medium comprising one or more microorganisms.

In some embodiments, the root chamber has a volume of 1-5 ml. The height of the root chamber to the diameter of the root chamber can be at least 1:5. The height of the root chamber to the diameter of the root chamber can be about 1:1. The height of the root chamber to the diameter of the root chamber can be at most 5:1. The height of the root chamber to the width of the root chamber can be at least 1:5. The height of the root chamber to the width of the root chamber can be about 1:1. The height of the root chamber to the width of the root chamber can be at most 5:1. The height of the root chamber to the depth of the root chamber can be at least 1:5. The height of the root chamber to the depth of the root chamber can be about 1:1. The height of the root chamber to the depth of the root chamber can be at most 5:1. The root chamber can be created by a cavity of a first layer and a second layer. The first layer can comprise a polydimethylsiloxane (PDMS) layer. The second layer can comprise a glass layer. The first layer can be reversibly attached to the second layer. The first layer can be permanently bond to the second layer. The inlet channel, the outlet channel, and the plant reservoir are disposed in the first layer. The device can be formed using a mold. The mold can comprise a base piece and a side piece, and wherein the base piece is reversibly attached to the side piece to form the mold. The medium can comprise one or more microorganisms. The medium can comprise a solid medium, a liquid medium, a gaseous medium, or a combination thereof. The device and/or the root chamber can be configured for vertical or placement or operation. The device and/or the root chamber can be configured for horizontal placement or operation. In some embodiments, the device comprises an upper chamber and a lower chamber. The lower chamber can comprise a base connected to a vertical section (e.g., tube). The upper chamber can comprise a vertical section (e.g., a tube). The height of the tube can be selected based on the plant (e.g., expected height of the plant). A rubber gasket between the lower chamber and the upper chamber can form an air-tight seal between the lower chamber and the upper chamber.

In some embodiments, the docking station comprises at least one docking bay for receiving the device. The docking station can comprise a growth light. The system can comprise, or be connected to, a liquid handling device. The system can comprise, or be connected to, a storage device.

In some embodiments, the method comprises: growing a plant using a device for determining plant-microbe interactions; and performing an analysis of the plant.

In some embodiments, the root chamber has a volume of 1-5 ml. The height of the root chamber to the diameter of the root chamber can be at least 1:5. The height of the root chamber to the diameter of the root chamber can be about 1:1. The height of the root chamber to the diameter of the root chamber can be at most 5:1. The height of the root chamber to the width of the root chamber can be at least 1:5. The height of the root chamber to the width of the root chamber can be about 1:1. The height of the root chamber to the width of the root chamber can be at most 5:1. The height of the root chamber to the depth of the root chamber can be at least 1:5. The height of the root chamber to the depth of the root chamber can be about 1:1. The height of the root chamber to the depth of the root chamber can be at most 5:1. The root chamber can be created by a cavity of a first layer and a second layer. The first layer can comprise a polydimethylsiloxane (PDMS) layer. The second layer can comprise a glass layer. The first layer can be reversibly attached to the second layer. The first layer can be permanently bond to the second layer. The inlet channel, the outlet channel, and the plant reservoir are disposed in the first layer. The device can be formed using a mold. The mold can comprise a base piece and a side piece, and wherein the base piece is reversibly attached to the side piece to form the mold. The medium can comprise one or more microorganisms. The medium can comprise a solid medium, a liquid medium, a gaseous medium, or a combination thereof. The device and/or the root chamber can be configured for vertical or placement or operation. The device and/or the root chamber can be configured for horizontal placement or operation.

In some embodiments, the device comprises an upper chamber and a lower chamber. The lower chamber can comprise a base connected to a vertical section (e.g., tube). The upper chamber can comprise a vertical section (e.g., a tube). The height of the tube can be selected based on the plant (e.g., expected height of the plant). A rubber gasket between the lower chamber and the upper chamber can form an air-tight seal between the lower chamber and the upper chamber.

In some embodiments, the analysis includes imaging the plant and spectroscopy analysis of the plant. Imaging the plant comprises light imaging the plant and performing Nanostructure-Initiator Mass Spectrometry (NIMS) analysis of the plant.

BRIEF DESCRIPTION OF THE DRAWINGS

FIGS. 3A1-3A3, 3B1-3B2, and 3C-3G show bonding PDMS to microscope slides.

FIGS. 5A1-5A2, 5B, 5C1-5C2, 5D, 5E1-5E2, and 5F show non-limiting exemplary components of 3D printed molds for plant growth device fabrication. Top and tilted views of a casting frame (FIGS. 5A1-5A2). Top and tilted views of an insert (FIG. 5B). Top and tilted views of a standard mold base (FIGS. 5C1-5C2). Top and tilted views of a wide-outlet mold base (FIGS. 5E1-5E2). Assembled molds for fabricating standard and wide-outlet plant growth devices (FIGS. 5D and 5F), respectively. The oval dimensions are approximately 51 mm×34 mm for a small plant growth mold and approximately 76 mm×62 mm for a large mold.

FIGS. 6A1-6A2, 6B1-6B2, and 6C1-6C2 show non-limiting exemplary designs of clamps for plant growth systems, including top and tilted views of a top clamp plate (FIGS. 6A1-6A2), top and tilted views of a bottom clamp plate (FIGS. 6B1-6B2), and top and tilted views of assembled clamp with four sets of hex cap screws (FIGS. 6C1-6C2).

FIG. 7 shows a non-limiting schematic of a plant growth system with independent LED growth light setup. The inset shows *Brachypodium* growing in a plant growth system with growth light on.

FIGS. 8A-8D show a non-limiting protocol of installing LED growth lights on a plant growth system. The protocol can include marking out the locations for a number of LED clips in a spiral around a plant growth container (FIG. 8A), attaching LED clips to the plant growth container (FIG. 8B), threading a LED strip through these clips (FIG. 8C), and connecting the LED strip to a controller wired with a 24V power supply (FIG. 8D). FIG. 8E shows a non-limiting exemplary schematic of wire connections to the controller.

FIGS. 9A-9F show the application of plant growth systems with independent LED growth light to grow plants under different light duration.

FIGS. 10A-10D show transferring seedlings into a plant growth system: FIG. 10A shows *Brachypodium distachyon* plants grown for 2 days on a 0.5 Murashige and Skoog (MS) plate. FIG. 10B shows filling the root chamber with plant growth medium. FIG. 10C shows using a tweezer to insert the root into the plant reservoir. FIG. 10D shows sealing the plant growth container with micropore tape, after adding 3 mL of water to the bottom of the container.

FIGS. 12A-12E show an exemplary integration of plant growth systems with NIMS imaging technique.

FIGS. 15A1-15A18 and 15B1-15B17 are non-limiting exemplary screenshots of videos showing root growth (FIGS. 3A1-15A18) and root-microbe interactions (FIGS. 15B1-15B17).

FIGS. 24A-24D show non-limiting exemplary white light photographs of *Brachypodium* incubated with four rhizobacteria strains.

FIGS. 27A-27G show using a plant growth system to study root morphology. FIGS. 27A-27F show root development of *Brachypodium distachyon* growing in EcoFABs filled with 0.5 MS medium during first three weeks: FIG. 27A: two days, FIG. 27B: four days, FIG. 27C: seven days, FIG. 27D: 11 days, FIG. 27E: 14 days, FIG. 27F: 21 days of growth. Averaged root surface areas shown in FIG. 27G were estimated by ImageJ software.

FIGS. 29A-29F are photographs of non-limiting exemplary plant growth systems used to grow a wide range of plants.

FIGS. 30A-30C show non-limiting exemplary schematic illustrations of a docking station of a plant growth platform.

DETAILED DESCRIPTION

Figure 1:
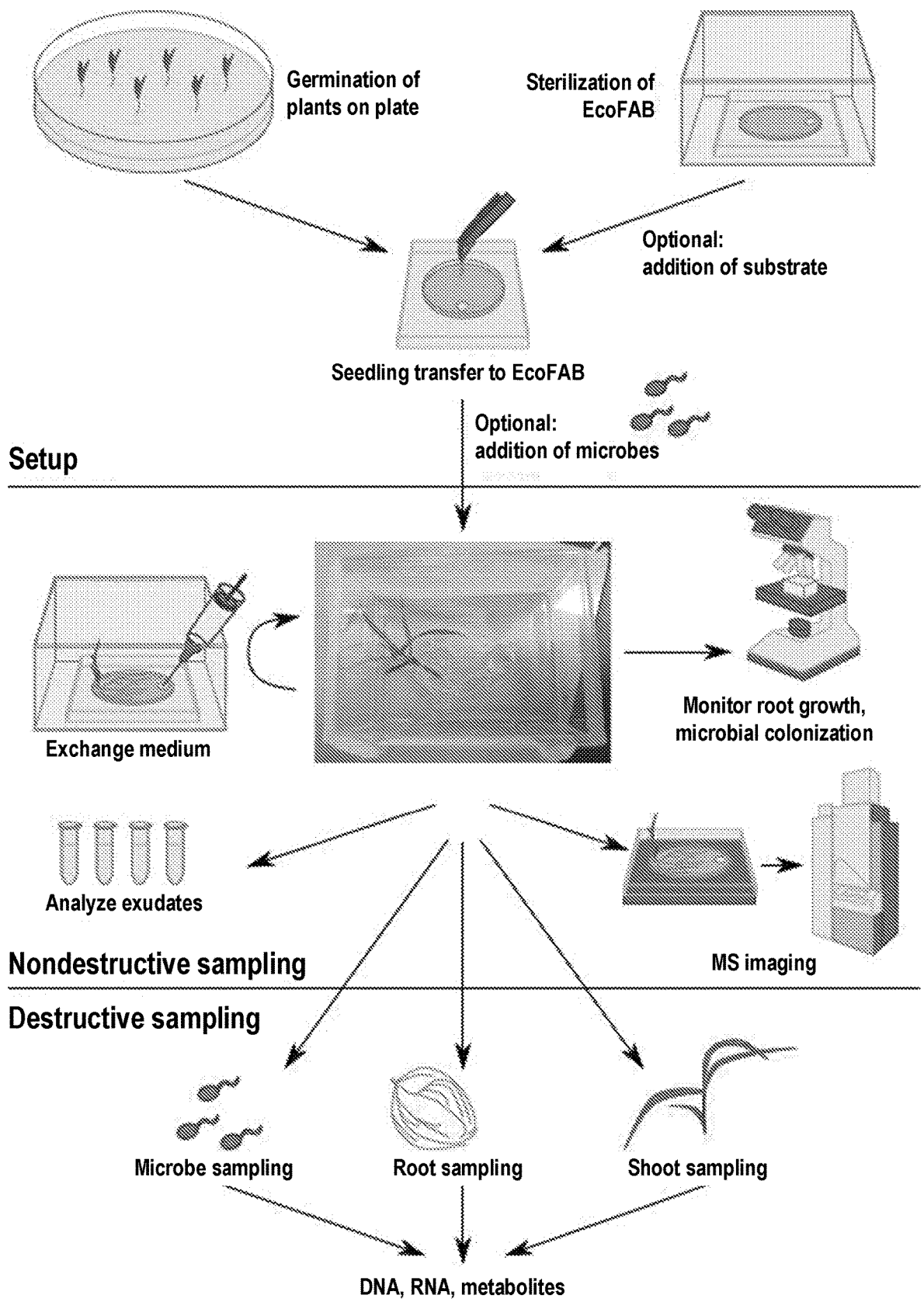
FIG. 1 is a non-limiting exemplary schematic illustration of a plant growth platform workflow.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Spring Harbor Press (Cold Spring Harbor, N.Y. 1989).

Beneficial plant-microbe interactions offer a sustainable biological solution with potential to boost low-input food and bioenergy production. A better mechanistic understanding of these complex plant-microbe interactions can be used for improving plant production as well as performing basic ecological studies investigating plant-soil-microbe interactions. Disclosed herein are plant growth platforms, systems, and devices for determining plant-microbe interactions. In some embodiments, a plant growth platform can be an ecosystem fabrication (EcoFAB) platform that utilizes an EcoFAB system with an EcoFAB device. Such EcoFAB platform, system, or device can be made using manufacturing technologies, such as three dimensional (3D) printing, to create controlled and/or reproducible laboratory habitats for mechanistic studies of plant-microbe interactions within specific environmental conditions. The size of an EcoFAB system or device can be adjusted for investigation of microbial interactions with various plant species (such as *Arabidopsis thaliana*, *Brachypodium distachyon* and *Panicum virgatum*). An EcoFab device can be a flow-through device that allows for controlled manipulation and sampling of root microbiomes, root chemistry, and/or imaging of root morphology and microbial localization.

Disclosed herein are methods for maintaining sterile conditions inside EcoFABs and mounting independent LED light systems onto EcoFABs. Also disclosed herein include methods for addition of different forms of media (such as soils, sand and liquid growth media) coupled to characterization of these systems using imaging and metabolomics. An EcoFab platform, system, or device can enable dynamic and detailed investigation of plant and plant-microbial consortia including manipulation of microbiome composition (such as mutants), monitoring of plant growth, root morphology, exudate composition, and microbial localization under controlled environmental conditions. In some embodiments, an EcoFAB platform, system, or device can be standardized for creating experimental conditions and investigating plant-microbe interactions.

Disclosed herein are methods for ecosystem fabrication to create platforms, systems, and devices (referred to herein as plant growth or EcoFAB platforms, systems, and devices) for systematic plant biology studies in highly controlled conditions (e.g., laboratory conditions). Advances in 3D printing provide widely accessible technologies for constructing and iteratively refining plant growth platform, system, and device designs. A plant growth device can include a root chamber suitable for imaging microscopy and maintaining sterility enabling controlled addition of microbes to investigate plant-microbe interactions. A plant growth platform can be compatible with various plant species. A root chamber can be narrow or wide (e.g., relative to a natural growth environment). In some embodiments, plant growth systems can mimic natural plant growth environments. For example, experimental results obtained and analyses thereof can be generalized to plants growing in natural environments. In some embodiments, growing plants in narrow root chambers can have physiological effects on plant growths.

In some embodiments, the use of sterile chambers and LED grow light enables investigation of the effects of various light conditions, including wavelength, intensity and duration, on plant growth and related physiological parameters in parallel. Reversible bonding root chambers can allow the use of solid substrates as well as to spatially collect solid samples for biochemical and genetic analysis. The applications of solid substrates, such as soils, sand and quartz beads, offer the possibilities of using plant growth platforms, systems, and devices to construct more ecologically relevant laboratory ecosystems. In some embodiments, saturated liquids (e.g., hydroponic cultures) can be used. Such saturated liquids may have effects on plant growths compared to natural soils. For example, natural soils can include air pockets. In some embodiments, saturated liquids can be modified to mimic soils with air pockets.

In some embodiments, cameras and microscopes can be used to image root system morphology development at both bulk to cellular levels. This suitability for monitoring root morphology imaging and quantification can be helpful understanding the regulatory mechanisms of plant physiological and molecular signals triggered by plant genotypic adaptions to growth conditions. A plant growth device and root chamber can be oriented horizontally or vertically. In natural environments, the roots gravitropic response can lead to a predominantly vertical development of the root system. Horizontal placements of plant growth devices and growths of plants can be used to investigate non-natural growth environments. Whether a plant growth device and root chamber have a horizontal or vertical orientation, root morphology parameters in various conditions, or in response to microbes, can be analyzed. High resolution imaging can be applied to capture root colonization dynamics of single isolates or communities, providing information about which plant parts can be colonized in various nutrient sufficient and deficient conditions. Accordingly, plant growth platforms, systems, can devices can generate new insights into how plant microbiomes are assembled, and how these dynamics change over time, for example as the roots develop.

In some embodiments, plant growth platforms and systems can include microfluidic devices for imaging of very young plants and collecting metabolites for LCMS analysis. In some embodiments, plant growth platforms can be used for imaging of root morphology when either the plants are transformed with chemiluminescent construct (Glo-root) or with NMR-based methods. Compared to soil-based systems (such as rhizotrons), metabolite extractions from plant growth systems and devices of the disclosure are not time consuming because of small volume of samples. In some embodiments, plant growth devices can be fabricated like microfluidic devices. Plant growth devices can be simple to use and inexpensive to reproduce. The size of the root chamber (or plant growth chamber or container) can be adjusted to grow plants with small or large root systems, up to their reproductive stages. The size of the root chamber (or plant growth chamber or container) can be different in different implementations. In some embodiments, simultaneous observations of root morphology changes and root exudation can be performed. A plant growth system and device can be kept sterile, enabling controlled addition of specific microbes.

Plant growth platforms, systems, and devices can enable controlled introduction and sampling of microbes and metabolites. For example, liquids collected from root growth chambers can be sufficient for mass spectroscopic metabolite profiling. The integration of mass spectrometry imaging (e.g. NIMS technique) can provide a non-destructive approach of studying metabolite spatial distributions of root systems. This technique can be helpful in stable isotope tracing experiments and mapping microbial localization to specific metabolites. A plant growth platform, system, and device can be sued to investigate single isolates and more complex communities. The sample volumes and biomass within the plant growth systems can sufficient for further integration with DNA sequencing technologies, which can allow characterization and monitoring microbial community structure and gene expression.

In some embodiments, plant-microbe interactions can be investigated using the platforms, systems, devices, and methods of the disclosure. The platforms, systems, devices, and methods can be simple, accessible, extensible, and generate reproducible results. In some embodiments, a plant growth platform can include a temperature control system such that each plant growth device can have independently controlled light and temperature. In some embodiments, a plant growth platform can include, or coupled to, a liquid handling system for automated sampling and refilling of the plant growth root chambers.

In some embodiments, a plant growth platform includes one or more plant growth docking stations and one or more plant growth systems. One or more plant growth systems can be placed in a plant growth docking station. A plant growth system can include one plant growth container (or chamber) and a plant growth device placed therein.

Plant Microbiome

The vital role microbiomes play in essentially all aspects of life on Earth have been increasingly recognized. Environmental microbial communities largely govern global nutrient cycling, including the carbon and nitrogen cycles, and microbiomes associated with soils and plants are vital to agriculture. Understanding how microbial communities associated with crop plants can promote low-input, high-productivity agriculture can be important. It has been known for some time that up to 50% of carbon fixed by plants is exuded by the roots. Likely a major portion of this is to attract and support beneficial microbes. Yet, significant research has been conducted on only a few key plant-microbe mutualisms, such as legume-rhizobia or mycorrhizal symbioses, which enable plants to access otherwise unavailable nitrogen and phosphorus sources.

Approaches based on Laboratory Consortia and Field Study

The application of beneficial plant microbes in agriculture offers great potential to increase sustainable food and biofuel production to provide for a growing population. Plant microbiomes play important roles in plant nutrient uptake, tolerance to stresses, and resistance to disease. However, it may be difficult to investigate these mechanisms of plant-microbe interactions in field ecosystems due to the complexity and associated irreproducibility and inability to precisely control microbiome composition and genetics (e.g., using microbial mutants). Approaches based on laboratory consortia may be hard to be connected to authentic fields, while approaches based on field studies may be very complicated. Critical details are missing about even these common forms of plant-microbe symbiosis and about a wide range of other growth promoting microbial interactions within the rhizosphere. Microbiome work to understand these interactions holds great promise to reduce the amount of fertilizer and water required for agriculture, while displacing petroleum-based products and improving the sustainability and yield of current practices.

Despite the investment and promise of plant-associated microbiome research, we lack vital understanding of the plant-microbe-soil interactions that govern these communities. Most approaches aimed at improving the understanding of soil microbial communities focus on examination of individual isolates or field studies of complex native communities. One research and development direction is constructing laboratory consortia, since these have the advantage that the constituent isolates can (in most cases) be characterized independently and even genetically manipulated to determine causal mechanisms. While these consortia systems allow researchers to test hypotheses about community interactions, the validity of extrapolating consortia-based findings to authentic 'field' communities has not been determined. Conversely, approaches for studying field microbial communities are challenging because they are so unconstrained and complex, and they often show irreproducible results such that definitive links between specific taxa and effects on plant growth or ecosystem function cannot be identified.

Model Ecosystems

In some embodiments, systems, methods, and devices for investigating model soil ecosystems and for controlled, replicated laboratory experiments that can be validated in the field are disclosed. Broad scientific community acceptance of a few of these model ecosystems can exponentially increase our understanding of microbial communities as a whole by focusing diverse expertise and capabilities on the same systems. By analogy, model organisms (e.g. mice) have been instrumental in determining the molecular and cellular biology of multicellular organisms. Indeed, human diseases are often studied using organisms that dramatically differ from humans (e.g. zebrafish) because they provide reproducible systems that can be manipulated in controlled experiments in labs around the world.

Plant Growth System Overview

Disclosed herein are systems, methods, and devices for determining plant-microbe interactions. In some embodiments, the device comprises: a root chamber for the root of a plant to grow, wherein the root chamber is connected with: an inlet channel for introducing a medium into the root chamber, an outlet channel for collecting plant exudates and metabolites, and a plant reservoir for the plant shoot of the plant to grow. FIGS. 6A1-6A2, 6B1-6B2, and 6C1-6C2 are non-limiting exemplary schematic illustrations of components of a plant growth device. FIGS. 14A-14B and 16A-16B show non-limiting exemplary schematic illustrations of a plant growth system.

New technologies are urgently needed to construct these model ecosystems with the capability of controlling the "microbial microenvironment"—the sum of all chemical and physical interactions impressed upon a cell by its biotic and abiotic environment. Studying these microenvironments by engineering and manipulating them and measuring their phenotypic outputs builds strong bottom-up understanding of the foundational chemical and genetic factors structuring microbial communities. While this may sound futuristic, advances in two dimensional (2D) and three dimensional (3D) fabrication of biomaterials could rapidly enable the construction of microbiomes with controlled microenvironments and targeted cellular interactions. Critically, these synthetic microbiomes can be at a range of scales (e.g. aggregate scale, plant-scale) and will allow use of extant microbial and host genetics tools to test the roles of individual taxa and combinations of genes and microbes in their microenvironment and interaction contexts, thus establishing causal connections. Central to this approach will be unlocking the enormous treasure trove of genetic diversity currently beyond the reach of laboratory microbiologists by using microenvironment control to enable high-throughput culturing of the "unculturable". FIGS. 5A1-5A2, 5B, 5C1-5C2, 5D, 5E1-5E2, and 5F show on-limiting exemplary illustrations of molds for fabricating a plant growth system of the disclosure.

Disclosed herein are plant growth platforms, systems, and devices for determining plant-microbe interactions. In some embodiments, a plant growth platform can be an ecosystem fabrication (EcoFAB) platform that utilizes an EcoFAB system with an EcoFAB device. The plant growth systems disclosed herein can be used for constructing reproducible and complex model ecosystems for the environment has the potential to greatly advance microbiome science. In some embodiments, these systems can be designed to be disseminated between scientists, bringing together diverse expertise and approaches to study the same controlled ecosystems to greatly accelerating our understanding of microbial communities.

An EcoFAB platform, system, or device can be used to construct model ecosystems (e.g., reproducible or simplified ecosystems) to enable controlled, replicated laboratory experiments investigating plant-microbe interactions to generate insights that can be further tested in larger scale or in the field. In some embodiments, an EcoFAB platform, system, or device can mimic growth conditions, such as soil-filled pots or on agar slabs within greenhouses or incubators, or below-ground conditions (e.g., to study below-ground processes, such as rhizosphere metabolites in soil. In some embodiments, an EcoFAB platform, system, or device can be used to monitor and manipulate plant growth environments in a precise, controlled, and/or reproducible manner. In some embodiments, an EcoFAB platform, system, or device can enable high throughput analysis using advanced microfluidic devices for plant phenotyping with micrometer-scale spatial resolution to monitor the early growth stages of the small model plant (e.g., monitoring the growth in *Arabidopsis thaliana* in liquid flow medium). In some embodiments, an EcoFAB platform, system, or device can be imaged using a two-layer imaging platform (e.g., root hair imaging of *Arabidopsis thaliana* at seedling stage).

Disclosed herein are plant growth platforms, systems, and devices for determining plant-microbe interactions. In some embodiments, a plant growth platform can be an ecosystem fabrication (EcoFAB) platform that utilizes an EcoFAB system with an EcoFAB device. An EcoFAB platform, system, or device can be used to investigate or determine microbe interactions with various plant species (such as *Arabidopsis thaliana, Brachypodium distachyon*, the ecologically important wild oat *Avena barbata,* and the bioenergy crop *Panicum virgatum* (switchgrass)). In some embodiments, an EcoFAB platform can be a sterile plant growth platform that includes two primary components: an EcoFAB device and a sterile plant-sized transparent container. The EcoFAB device can be made using a plastic manufacturing process. For example, a polydimethylsiloxane (PDMS) manufacturing process can be used to manufacture an EcoFAB device, which can include as casting PDMS layers from a 3D printed plastic mold and bonding PDMS layers onto microscope slides. Disclosed herein are embodiments of an EcoFAB method or workflow, which can include EcoFAB device fabrication, sterilization, seed germination, seedling transplantation, microbe inoculation/coc-ultivation, sample preparation and analysis. FIG. 1 is a non-limiting exemplary schematic illustration of an EcoFAB method. An EcoFAB method can include setup (e.g., plants are germinated on plate and transferred to the sterilized EcoFAB, and microbes can be added), nondestructive or semi-nondestructive sampling (e.g., root exudates can be sampled and imaged, and root morphology can be visualized) and/or destructive sampling which can allow analysis of microbe, root and shoot parameters in detail.

In some embodiments, an EcoFAB method includes the installation of controlled growth lights (e.g., computer controlled LED growth lights shown in FIGS. 7 and 8A-8D) and the utilization of solid substrates. Imaging techniques can be used to investigate root morphology changes, microbial colonization of roots, and mass spectroscopic imaging of root exudates are described. In some embodiments, an EcoFAB platform, system, or device can used for standardizing and/or community collaboration of studies of laboratory plant—microbiome interactions. In some embodiments, an EcoFAB platform, system, or device can include an inexpensive design and manufactured using readily available materials.

In some embodiments, a plant growth device (e.g., an EcoFAB device) of a plant growth system comprises a plant growth device in, or placed in, a plant growth container or chamber, which allows for controlled, replicated laboratory experiments that can be validated in the field study. The plant growth device can include a root chamber. The root chamber and/or plant growth container or chamber can be designed in SolidWorks. A 3D plastic printer can be used to print the mold for casting PDMS layers, which can be attached to the glass substrates (e.g., via plasma triggered permanent bonding or reversible sealing). The capacity of the plant growth device can be varied from 1.5 ml medium volume to 5 ml or lager volume depending on the plant size. In some embodiments, two polytetrafluoroethylene (PTFE) tubes can be connected to inlet and outlet channels of the root chamber (or plant growth container or chamber). The liquid medium as well as microbes can flow into the root chamber (or plant growth container or chamber) through the inlet channel. Plant exudates and other metabolites from plant-microbe interactions will be collected through the outlet channel.

In some embodiments, the size of the root chamber can be, or be about, 1 ml, 2 ml, 3 ml, 4 ml, 5 ml, 6 ml, 7 ml, 8 ml, 9 ml, 10 ml, 11 ml, 12 ml, 13 ml, 14 ml, 15 ml, 16 ml, 17 ml, 18 ml, 19 ml, 20 ml, 21 ml, 22 ml, 23 ml, 24 ml, 25 ml, 26 ml, 27 ml, 28 ml, 29 ml, 30 ml, 31 ml, 32 ml, 33 ml, 34 ml, 35 ml, 36 ml, 37 ml, 38 ml, 39 ml, 40 ml, 51 ml, 52 ml, 53 ml, 54 ml, 55 ml, 56 ml, 57 ml, 58 ml, 59 ml, 60 ml, 61 ml, 62 ml, 63 ml, 64 ml, 65 ml, 66 ml, 67 ml, 68 ml, 69 ml, 70 ml, 71 ml, 72 ml, 73 ml, 74 ml, 75 ml, 76 ml, 77 ml, 78 ml, 79 ml, 80 ml, 81 ml, 82 ml, 83 ml, 84 ml, 85 ml, 86 ml, 87 ml, 88 ml, 89 ml, 90 ml, 91 ml, 92 ml, 93 ml, 94 ml, 95 ml, 96 ml, 97 ml, 98 ml, 99 ml, 100 ml, or a number or a range between any two of these values. In some embodiments, the size of the root chamber can be at least, or at most, 1 ml, 2 ml, 3 ml, 4 nil, 5 ml, 6 ml, 7 nil, 8 ml, 9 ml, 10 ml, 11 ml, 12 ml, 13 ml, 14 ml, 15 ml, 16 ml, 17 ml, 18 ml, 19 ml, 20 ml, 21 ml, 22 ml, 23 ml, 24 ml, 25 ml, 26 ml, 27 ml, 28 ml, 29 ml, 30 ml, 31 ml, 32 ml, 33 ml, 34 ml, 35 ml, 36 ml, 37 ml, 38 ml, 39 ml, 40 ml, 51 ml, 52 ml, 53 ml, 54 ml, 55 ml, 56 ml, 57 ml, 58 ml, 59 ml, 60 ml, 61 ml, 62 ml, 63 ml, 64 ml, 65 ml, 66 ml, 67 ml, 68 ml, 69 ml, 70 ml, 71 ml, 72 ml, 73 ml, 74 ml, 75 ml, 76 ml, 77 ml, 78 ml, 79 ml, 80 ml, 81 ml, 82 ml, 83 ml, 84 ml, 85 ml, 86 ml, 87 ml, 88 ml, 89 ml, 90 ml, 91 ml, 92 ml, 93 ml, 94 ml, 95 ml, 96 ml, 97 ml, 98 ml, 99 ml, or 100 ml.

The ratio of the height of the root chamber to the diameter of the root chamber can be different in different implementations. In some embodiments, the ratio of the height of the root chamber to the diameter of the root chamber can be, or be about, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, or a number or a range between any two of these values. In some embodiments, the ratio of the height of the root chamber to the diameter of the root chamber can be at least, or at most, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, or a number or a range between any two of these values. In some embodiments, the ratio of the height of the root chamber to the diameter of the root chamber can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, or a number or a range between any two of these values. In some embodiments, the ratio of the height of the root chamber to the diameter of the root chamber can be at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, or 100:1.

The ratio of the height of the root chamber to the depth of the root chamber can be different in different implementations. In some embodiments, the ratio of the height of the root chamber to the depth of the root chamber can be, or be about, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, or a number or a range between any two of these values. In some embodiments, the ratio of the height of the root chamber to the depth of the root chamber can be at least, or at most, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, or a number or a range between any two of these values. In some embodiments, the ratio of the height of the root chamber to the depth of the root chamber can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, or a number or a range between any two of these values. In some embodiments, the ratio of the height of the root chamber to the depth of the root chamber can be at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, or 100:1.

The ratio of the height of the root chamber to the width of the root chamber can be different in different implementations. In some embodiments, the ratio of the height of the width chamber to the diameter of the root chamber can be, or be about, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, or a number or a range between any two of these values. In some embodiments, the ratio of the height of the root chamber to the width of the root chamber can be at least, or at most, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, or a number or a range between any two of these values. In some embodiments, the ratio of the height of the root chamber to the width of the root chamber can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, or a number or a range between any two of these values. In some embodiments, the ratio of the height of the root chamber to the width of the root chamber can be at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, or 100:1.

In some embodiments, plant growth systems can be used by the larger scientific community, including laboratory, field and computational scientists. Thus, assemblies of communities of scientists around specific plant growth systems, analogous to the existing *Brachypodium* and *Arabidopsis* communities may be important.

In some embodiments, advantages of the plant growth systems include easy and simplicity of use. Plant growth systems can be used to create a sterile environment for reproducible experiments. Plant growth systems can be integrated with microscopic imaging for determining root growth and root-microbe interactions. Plant growth systems can be used for LC-MS analysis of root exudates and root-microbe interactions. Plant growth systems can allow root exudates to be easily collected and metabolites easily collected because of the small volume (e.g., 2-5 ml, 0.1-10 ml) of root growth chambers in plant growth devices of plant growth systems. Plant growth systems can be integrated with NIMS imaging, a nearly non-destructive approach to image root metabolites. Plant growth systems with growth light (e.g., LED growth light) can enable many experiments to be performed at the same time efficiently and cost effectively. Experiments with Plant growth systems can allow easy reproducibility.

In some embodiments, it can be advantageous to seal the root chamber (or plant growth container or chamber) during part or the entire experiment circle, which can reduce the possibility of any contaminations. The plant growth systems can require very small volume of plant growth media, which can concentrate root metabolites and reduce the tremendous effort for sample analysis. The reversible sealing design of the plant growth systems enables studying and investigating plant-microbe interactions in soil or other solid media. Soil samples from plant root systems can be spatially collected. The plant growth systems can be integrated with the mass imaging approach to study the plant or plant-microorganisms interactions. The plant growth systems can fit into the microscope setup, which allows for determining root growth and root-microbe interactions visually. Furthermore, grow light (e.g., LED growth light) can be coupled to each individual plant growth chamber. The light power and exposure time can be controlled using a controller. With this capability, many plant grow conditions can be studied simultaneously at a very low cost as well as small space, especially when comparing with plant incubators and green houses. Plant growth systems disclosed herein provide a platform to advance understanding of plant microbiomes. The plant growth systems can be used to investigate the mechanisms how plants select beneficial microbes and how these beneficial microbes improve plant productivity and environmental tolerance.

Applications

In some embodiments, the plant growth systems disclosed herein can be used for research and development (e.g., as general research tools). In some embodiments, the plant growth systems can be used to deconstruct ecological processes between soil-plants-microbes using imaging, systems biology, and synthetic biology tools. For example, one or more genes associated with a pathway that makes a metabolite (e.g., a secondary metabolite) can be knocked out of or added in a microbe (or a plant). Then how this modification impacts the plant, the plant microbiome, and the composition of metabolites in the soil in which the plant grows can be tested and determined. The location of where the metabolite is made can be determined and localized. As another example, the plant growth systems can be used to discover or determine plant and microbial genes that confer enhanced, low-input (e.g., low water, nitrogen, or phosphorous input) plant growth, or that build soil carbon in soils.

Docking Station

In some embodiments, a plant growth system can include a docking station. The docking station can be a reusable device for plant growth devices that can be plugged into the docking station. The docking station can include capabilities, such as heating, cooling, lighting, controlling media introduction, sampling (e.g., gas, liquid, or solid sampling), imaging (e.g., light microscopy imaging), and spectroscopy. The docking station can be connected to a control system the capabilities of the docking station. In some embodiments, the plant growth devices can be disposable, while the docking station can be reusable.

FIGS. 30A-30C show non-limiting exemplary schematic illustrations of a docking station of a plant growth platform. A plant growth docking station can include a modular station complete with "docking bays" and self-contained equipment for the liquid and gas flow and sampling of a small set of plant growth devices in plant growth containers or chambers. FIG. 30A shows a single modular, self-contained docking station or bay that can be connected to resources for growing plants (e.g., an air tank). FIG. 30B shows a docking station with several docking bays that can be connected to and operated by a single docking station.

Figure 31A:
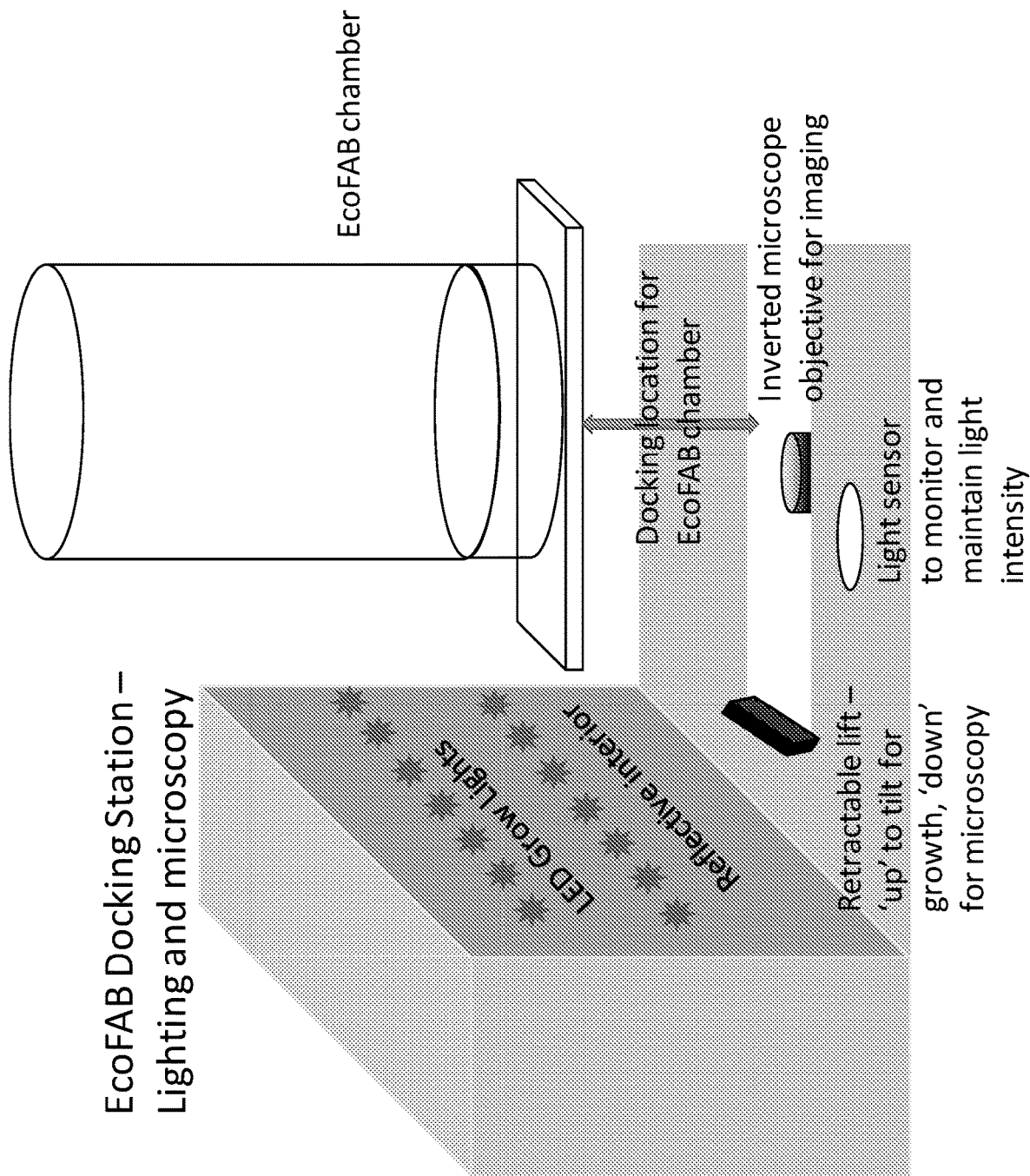
FIGS. 31A-31B show a schematic illustration of a docking station with growth lights.
Figure 31B:
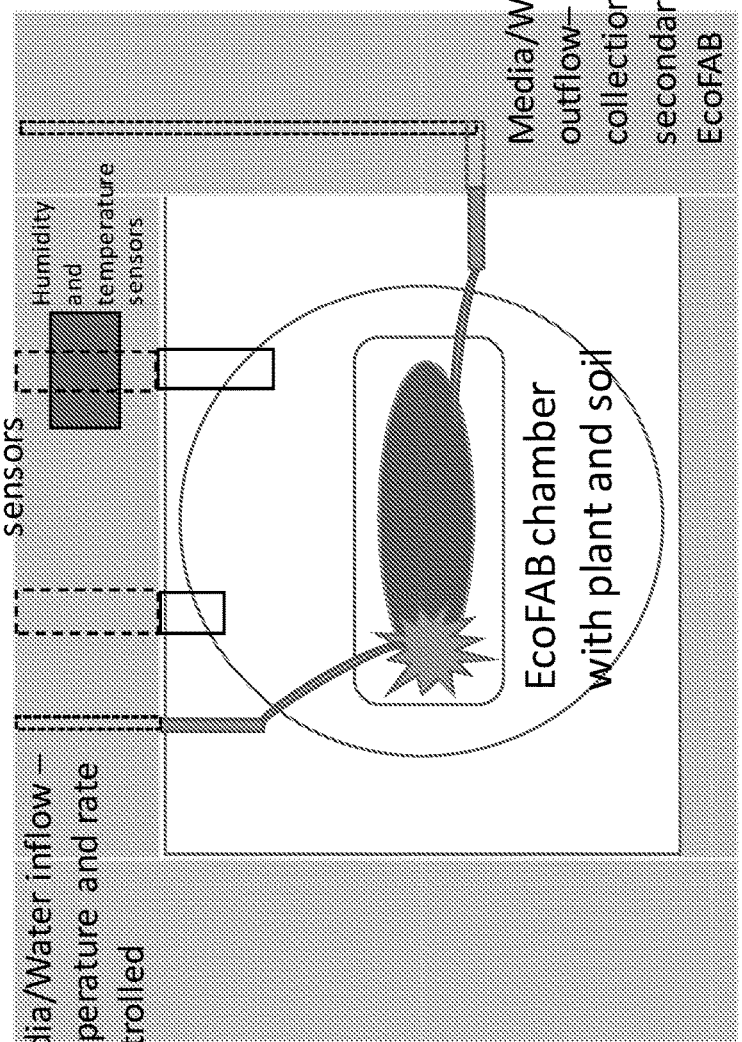

FIGS. 31A-31B show a schematic illustration of a docking station with growth lights. Each docking bay can be designed to provide a controlled environment for plant growth devices or chambers. Lights (e.g., LED lights) can provide the desired and/or proper growth conditions, and the interior of the bay can be reflective to improve lighting efficiency. The number and/or intensity of the lights can be monitored and adjusted based on a light sensor within the docking bay. Each plant growth device with a root chamber can be placed in a plant growth container or chamber. The plant growth chamber (thus the plant growth device and root chamber) can sit on an open base to allow for inverted microscopy and a retractable lift can be engaged when not being imaged to better simulate natural gravity and flow in the chamber.

In some embodiments, temperature, sampling rate, carbon dioxide concentration, humidity can be monitored (e.g., via effluent gas readings) and then adjusted through the gas and liquid supplies. Effluents from a planted growth device or chamber can then be directed to storage vessels for collection or to secondary, non-planted growth devices for subsequent analyses.

In some embodiments, a docking station can be used for controlling heating or cooling of the device, media introduction into the device, sampling from the device, lighting of the device, imaging the plant in the device, or spectroscopy analysis of the plant in the device. The number of docking bays for receiving plant growth devices or chambers per docking station can be different in different implementations. In some embodiments, the number of docking bays per docking stations can be, or be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more. In some embodiments, the number of docking bays per docking stations can be at least, or at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. The number of growth lights per docking station can be different in different implementations. In some embodiments, the number of growth lights per docking stations can be, or be about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more. In some embodiments, the number of growth lights per docking stations can be at least, or at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. The docking station can comprise a growth light. The system can comprise, or be connected to, a liquid handling device. The system can comprise, or be connected to, a storage device.

EXAMPLES

Some aspects of the embodiments discussed above are disclosed in further detail in the following examples, which are not in any way intended to limit the scope of the present disclosure.

Experimental Materials and Methods

The following experimental materials and methods were used for Examples described below.

Plant growth device fabrication and sterilization

Microscopic slides (75×50×1 mm slides purchased from VWR, 102×83×1.3 mm slides purchased from Ted Pella) of plant growth devices were cleaned thoroughly and rinsed with MilliQ water, and then baked for 1 hours in a 400° C. oven (Agilent 6890N). Molds for PDMS layers of plant growth devices were designed in SolidWorks 2016 and printed with Vero White Plus material by a PolyJet 3D plastic printer. Siloxane base and Pt-based catalyst (Dow Corning Sylgard 184 Silicone kit, Ellsworth Adhesives) were mixed following the ratios of 5:1, 10:1, 30:1 and then was cured under vacuum for 30 minutes to remove air bubbles. The mixture was poured into the molds and placed on a 70° C. hot plate for 4 hours to form PDMS device layers. Microscopic slides and PDMS layers fabricated with 5:1 base-catalyst mixture were assembled by a set of clamps (as shown in FIGS. 6C1-6C2) that was designed in SolidWorks 2016 and printed with acrylonitrile butadiene styrene (ABS) material by a 3D plastic printer (LulzBot TAZ 6, LulzBot). PDMS layers from 10:1 base-catalyst mixture were bonded onto microscopic slides with 2 minutes oxygen plasma exposure (PDC-32G, Harrick Plasma) while PDMS layers from 30:1 base-catalyst mixture can reversibly attach onto microscopic slides without any treatment.

Plant growth devices were placed inside clear acrylic boxes (44×65×90 mm for small plant growth devices and 240×240×140 mm for large plant growth devices, Amazon) that were filled with one third of 70% ethanol solution (Sigma-Aldrich). The acrylic boxes with plant growth devices were shaken thoroughly to make sure ethanol solution cover every corner of the boxes as well as growth chambers of plant growth devices. 70% ethanol solution was removed from the plant growth boxes after 1 hour, and then the boxes were soaked with 100% ethanol with lids open for 12 hours in a sterile hood (AC600 Series PCR Workstations, AirClean® Systems) to get rid of all the solvent residues. The plant growth boxes were further sterilized by UV light inside the sterile hood for 2 hours right before use.

Plant growth media

Murashige & Skoog salt (MS, Phytotechnologies Laboratories) medium were prepared by mixing 2.115 g macronutrient and 0.05 g micronutrient salt solution in 1 L Milli-Q water. The soil (Pro-Mix PGX, Hummert International) and water mixture with 100 g/L soil was shaken in a 4° C. cold room for 2 hour, and then pumped through a filter bottle with pore size of 0.22 um to remove soil particles and get clear soil extract medium. Both MS medium and Soil extract medium were autoclaved for further sterilization and stored in a 4° C. refrigerator to avoid precipitation.

Seed sterilization and germination

Switchgrass seeds (Alamo switchgrass, obtained from The Samuel Roberts Noble Foundation) were suspended with 60% sulfuric acid (Sigma-Aldrich) for 1 hours before sterilization to improve their germination rates. All three types of seeds, including Arabidopsis (Arabidopsis thaliana, WT-24 Col-4 Columbia wild type, Lehle Seeds), Brachypodium (Brachypodium distachyon, standard Bd-21 line, from John Vogel's group) and Switchgrass, were first suspended in 70% ethanol for 2 minutes. After removing ethanol, seeds were soaked in 50% bleach solution for 5 minutes and then rinsed with sterile water for three times. The seeds were kept in wet Eppendorf tubes and stored in a 4° C. refrigerator. After 2 days stratification, the seeds were plated onto MS medium solidified with 0.6% phytagel (Sigma-Aldrich). The seedling plants were transferred into plant reservoirs of plant growth devices after 2 days germination.

Root Exudates Collection and Extraction

Plant root exudates were collected into Eppendorf tubes through the flow outlets of plant growth devices in a sterile hood and were then freeze-dried by a lyophilizer (FreeZone 2.5 Plus, LABCONCO) to remove water. 300 μL methanol (Sigma-Aldrich) was added into the tubes and sonicated for 30 minutes. The salts or other precipitations sit on the bottom of the tubes after 5 minutes centrifuge at 6000×g force. Supernatant solutions from the tubes were collected and dried in a SpeedVac Concentrator (Savant™ SPD111 SpeedVac, Thermo Scientific). 150 μL methanol with LC-MS internal standards (Info) was added into each tube and incubated for 12 hours in a 4° C. refrigerator. After incubation, root exudate samples were centrifuged again and then filtered with 0.22 um filter tubes to remove any salt residues.

Instrumentation: LC/MS analysis

Metabolites from extracts of plant growth root growth chambers were chromatographically separated using hydrophilic interaction chromatography on SeQuant ZIC-HILIC column (Millipore 50447, 100×2.1 mm, 200 A, 3.5 um) on an Agilent 1290 LC system. Metabolites were analyzed on a downstream Thermo Scientific™ Q Exactive™ Hybrid Quadrupole-Orbitrap Mass Spectrometer equipped with a HESI-II source probe using Full MS with Data Dependent tandem MS. Method parameters were as indicated in Table 1. Each sample was injected in two sequential injections, first for positive mode analysis and second for negative mode analysis. Sample injections were randomized with solvent blank injections between each; internal and external standards were used for quality control purposes and retention time predictions of compounds in an in-house standards library. Data were analyzed using Metabolite Atlas and custom Python scripts. Metabolite identification was based on m/z values, retention time and possible compound fragmentation patterns by comparison to a library of metabolite standards.

TABLE 1

Method Parameters of Liquid-Chromatography Mass Spectrometry.

| Q Exactive parameters | | | |
|---|---|---|---|
| Methods | NEG_MSMS, POS_MSMS | LC parameters | |
| | | Chromatography 1: | HILIC |
| Instrument mode | Q Exactive Full MS -> ddMS2 | Binary pump Thermostated column compartment | G4220A G1316C |
| Sheath gas flow rate | 55 | Autosampler | G4226A |
| Aux gas flow rate | 20 | ALS thermostat | G1330B |
| Sweep gas flow rate | 2 | Column compartment temperature: | held at 40 degrees C. |
| Spray voltage (|kV|) | 3 | Column Model: | 50447 |
| Capillary temp. (degrees C.) | 400 | Column Manufacturer: | Millipore |
| S-lens RF level | 50 | Column serial #: | 658875 |
| FULL MS | | Composition of mobile phase solvent A: | 5 mM ammonium acetate in water |
| resolution | 70000 | Composition of mobile phase solvent B: | 5 mM ammonium acetate in 95:5 acetonitrile: water |
| AGC target | 3.00E+06 | Autosampler settings: | draw and eject speeds at 20 uL/min, 1 mm draw position w 2 second equilibration time and 5x flush out factor, 3 second flush port needle wash enabled |
| Max. IT | 100 ms 70-1050 | Timetable | |
| Scan range | m/z | Time | % B | Flow (uL/min) |
| Spectrum data type | Centroid | 0 | 100 | 0.45 |
| dd-MS2 settings | | 1.5 | 100 | 0.45 |
| resolution | 17500 | 15 | 65 | 0.45 |
| AGC target | 1.00E+05 | 18 | 0 | 0.6 |
| Max. IT | 50 ms | 23 | 0 | 0.6 |
| Loop count | 2 | 25 | 100 | 0.45 |
| TopN | 2 | 30 | 100 | 0.45 |

TABLE 1-continued

Method Parameters of Liquid-Chromatography Mass Spectrometry.

| | |
|---|---|
| isolation window (m/z) | 2 |
| (N)CE/stepped nce | 10,20,30 |
| Spectrum data type | Centroid |
| dd Settings | |
| MM. AGC target | 1.00E+03 |
| Charge exclusion | >3 |
| Exclude isotope | on |
| Dynamic exclusion | 10 seconds |

Instrumentation: Nanostructure-Initiator Mass Spectrometry (NIMS) Imaging

NIMS chips were fabricated by an electrochemical etching approach for 15 minutes, as discussed previously. The liquid initiator for coating NIMS chips was BisF17 from Gelest. NIMS imaging of plant roots was acquired by an AB Sciex TOF/TOF 5800 MALDI mass spectrometer that was configured at positive ionization mode. OpenMSI program was used to generate NIMS images of root metabolites.

Setup of Plant Growth Systems with LED Growth Light

Nano coated LED grow strips (3:1 red/660 nm to blue/450 nm LEDS, LED World) were attached to the outside of plant growth boxes with silicon LED clips that were glued on the boxes using a hot glue gun. The input channel of a TC420 LED controller (RGBSIGHT, Amazon.com) was connected to a power supply (110-120 V input, 24 V output, LED World) and its output channels were linked to one ends of LED strips. The LED controller was programmed with a Windows software, Pled. Besides adjusting light duration cycles and intensity, the controller also has pulse width modulation functions to enable gradual fades between different brightness levels.

Example 1

Casting PDMS Layers

This example demonstrates casting PDMS layers for plant growth systems.

Materials and Equipment 1. 3D printed mold, plug, and casting tray (STL files available from Northen Lab)
2. PDMS: Dow Corning Sylgard 184 Silicone Elastomer Clear Kit (Ellsworth Adhesives)
3. Vacuum chamber
4. Hot plate/heating block
5. Compressed gas duster
6. Utility knife Protocol 1. Plant Growth Device Fabrication: Casting PDMS Layers 1.1. Measure out and pour 40 mL of PDMS elastomer base into a mixing container. Each layer uses ~40 mL of elastomer base. To make more or less layers per batch, adjust volume used accordingly.

1.2. Add 4 mL of elastomer curing agent to form a 10:1 ratio of base to curing agent. A 30:1 ratio will make a softer, stickier layer that can be reversibly adhered to glass. A 5:1 ratio will make a harder, less-adhesive layer that can be used in conjunction with a clamp and reversely bond to a NIMS chip. Mix gently with a stirring stick to avoid introducing air bubbles, but enough to fully incorporate the curing agent.

1.3. Place the mixture in a vacuum chamber to de-gas for 30-45 minutes, or until no air bubbles remain.

1.4. Fit the mold into the casting tray. Check that mold is level. Add the plug to the mold. If there is not a tight seal between the mold and casting tray, try wrapping the mold's edge with lab tape, then press into tray.

1.5. Pour the elastomer mixture into the clean mold. Pour slowly to avoid introducing air bubbles. If desired, use a large disposable syringe to add the mixture, although this may introduce air bubbles.

1.6. Use a compressed gas duster to blow away any bubbles sticking to the mold's surface or to the plug.

1.7. Place the mold on a heating block set to 85° C. for 1 hour. PDMS can be cured at various temperatures. Hotter curing temperatures will result in faster curing times.

1.8. Test if the PDMS has set by prodding the surface with a stirring stick. The surface should be firm and rubbery, and should not be wet or gooey.

1.9. Gently pull out the plug. Use a thin spatula or stirring stick to help separate the PDMS from the plug. Do not rip the PDMS layer.

1.10. Slowly run a utility knife down between the tray and PDMS to separate them. Also cut and remove any PDMS that may have leaked through the tray on the underside of the mold.

1.11. Press the mold with the PDMS out of the tray. Try not to warp the mold, as it is a thermoplastic and will become slightly flexible when heated.

1.12. Use the knife to gently separate the PDMS from the mold at the edges.

1.13. Starting at a corner, slowly peel the PDMS layer off of the mold.

1.14. Store PDMS layer in a dust-free container. Avoid touching the bonding side (the side that was in contact with the mold). If storing multiple layers, stack them bonding to bonding side to keep this surface clean of PDMS "crumbs" and uncured PDMS.

1.15. Clean off the mold and casting trays of PDMS debris. Use tape or tweezers to remove any remaining "crumbs" of PDMS. Rinse with methanol, then air-dry.

Figure 2B:
FIGS. 2A-2J show casting of PDMS layers.
Figure 2D:
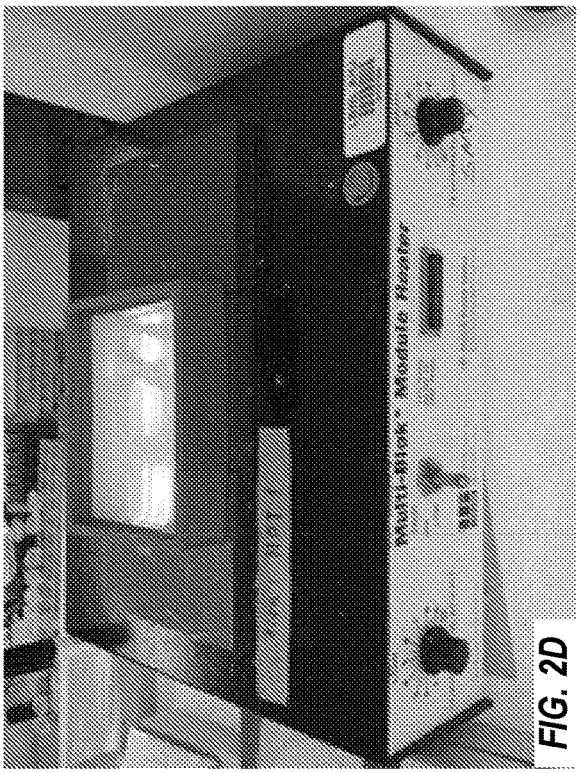
Figure 2A:
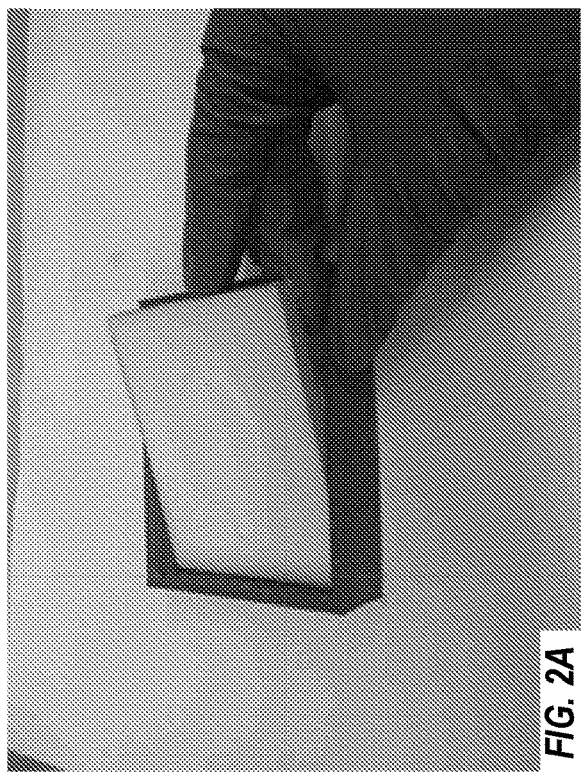
Figure 2C:
Figure 2E:
Figure 2F:
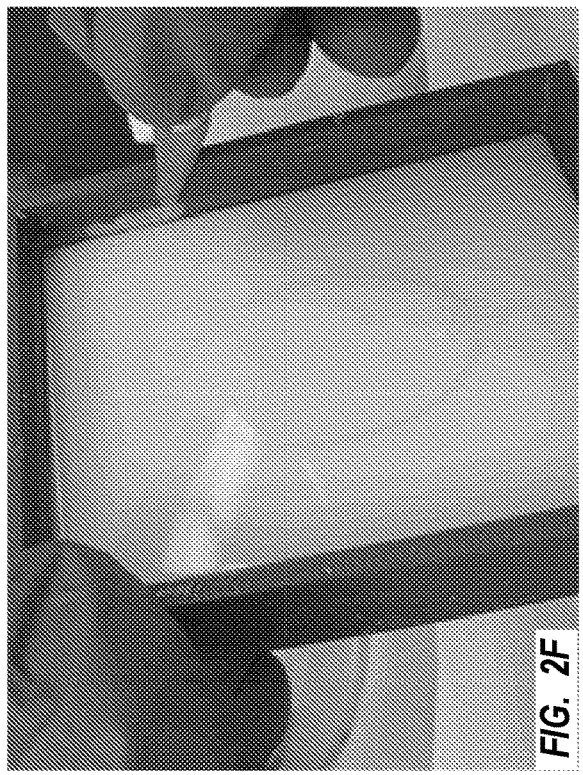
Figure 2G:
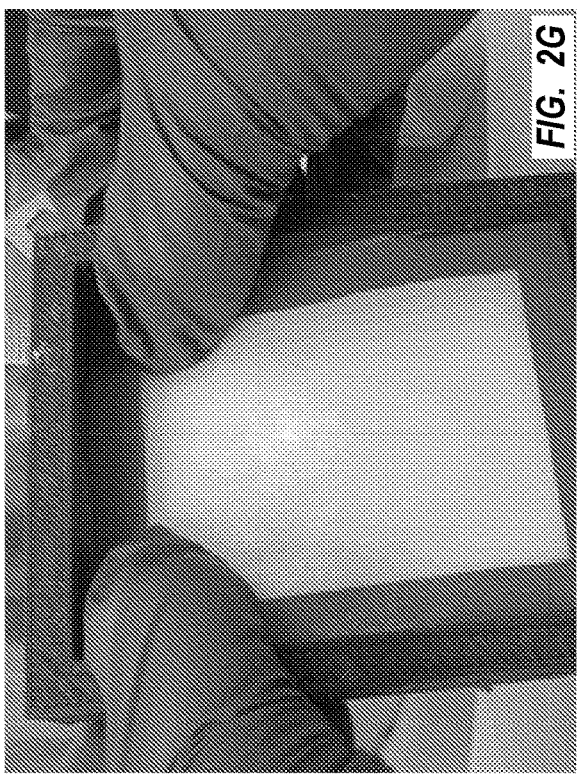
Figure 2H:
Figure 2J:
Figure 2I:
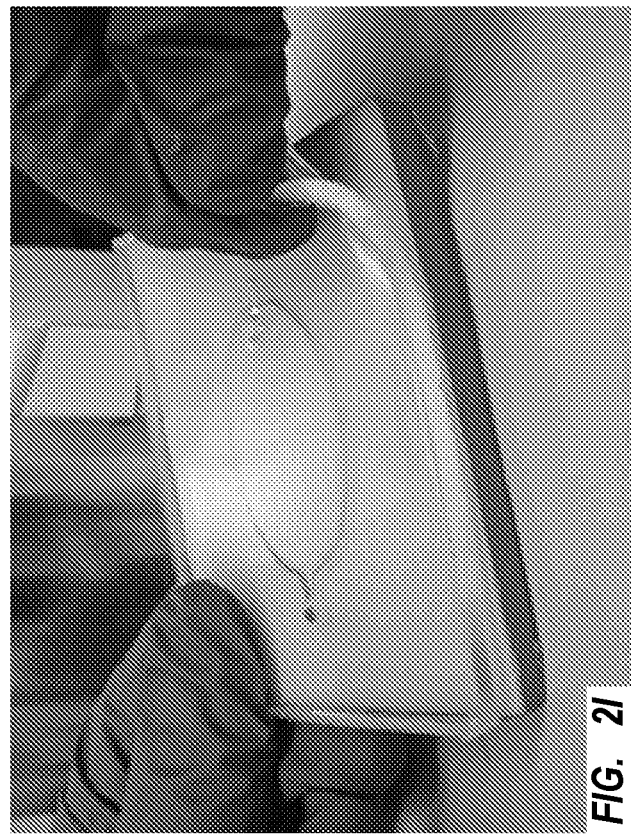

FIGS. 2A-2J show casting of PDMS layers. FIG. 2A shows inserting the mold (top) into the casting tray (bottom). FIG. 2B shows inserting the plug into the mold, creating a reservoir opening for the plant shoot. FIG. 2C shows pouring the mixed elastomer base and curing agent into the cast. Pour slowly to avoid air bubbles. FIG. 2D shows heating uncured PDMS at approximately 85° C. for one hour. FIG. 2E shows after testing the PDMS for firmness, gently removing the plug, using a spatula to help separate the plug from the PDMS without tearing. FIG. 2F shows using a utility knife to separate the PDMS from the casting tray, and cut away any PDMS that leaked through to the underside. FIG. 2G shows pushing the mold out of the casting tray. FIG. 2H shows using a knife to separate the PDMS from the mold along the edges. FIG. 2I shows peeling the PDMS layer slowly off of the mold, starting from a corner. Touching the underside of the PDMS should be avoided. FIG. 2J shows stacking finished PDMS layers bonding side to bonding side (the side that was touching the mold), to avoid contamination of these surfaces.

Altogether, these data demonstrates casting a PDMS layer with a mold.

Example 2

Bonding PDMS Layers to Microscope Slides

This example demonstrates bonding PDMS layers to microscope slides.

Materials and Equipment

1. Microscope glass slides (3"×2" for small plant growth devices, 4"×3¼" for large plant growth devices)
2. Baking oven (for sterilization)
3. Plasma Cleaner (Harrick Plasma, Model PDC-001)
4. Hot plate/heating block Protocol 2. Plant Growth Device Fabrication: Chemically Attaching PDMS Layers onto Microscope Slides 2.1. Wash glass slides with warm soap and milli-Q filtered water.

2.2. Bake glass slides at 400° C. for 1 hour to sterilize and remove trace compounds.

2.3. With scissors or utility knife, cut the PDMS layer to fit the glass slide (3"33 2" for the small size, 4" by 3¼" for the large size). Even if the large sized PDMS fits on the large glass slide without trimming, still trim off the edges of the PDMS. The edges often have a raised lip from being cast, and this lip will prevent PDMS from making complete contact with glass during bonding. Avoid allowing the PDMS to overhang the glass.

2.4. Using a 15 gauge blunt needle, punch out holes to create openings as flow channels. The standard mold has an inlet and outlet port that needs to be punched out, while the wide-outlet mold only needs the inlet port to be punched out.

2.5. Rinse the bonding side of the PDMS layer with methanol. Air dry or blow the surface with an ultra pure compressed nitrogen gun.

2.6. Place a glass slide and PDMS layer into the plasma cleaner, bonding sides up. Make sure they are not touching each other.

2.7. Close the chamber and gas vent, switch the RF level to "OFF", and turn on the "vacuum" and "power" switches. Run for one minute.

2.8. Switch RF Level to "HI" for 15 seconds. You should observe a pink/purple glow in the chamber from the ionized oxygen.

2.9. Turn off the "vacuum" and "power" switches, and release pressure in the chamber.

2.10. Quickly (within 15 seconds) remove the glass and PDMS, and press the PDMS layer onto the glass, applying even pressure for about 15 seconds. Once PDMS has touched glass, do NOT attempt to peel it off and re-stick. This will prevent a permanent bond from forming. Align the PDMS onto the glass correctly the first time. Make sure the center oval region of the PDMS layer (root growth chamber), where the plant root will grow, does NOT touch the glass.

2.11. Place the sealed chip on the heating block at 50° C. for 20 minutes. Allow chip to finish sealing overnight at room temperature before checking the seal. Do not stack plant growth devices on each other during this time. The glass from one device may bond with the PDMS layer from the device below. If properly sealed, when you attempt to peel the PDMS off the glass, the PDMS should tear itself apart before separating from the glass.

2.12. Keep the assembled plant growth chip/devices in a clean, dust-free environment.

Figure 3D:
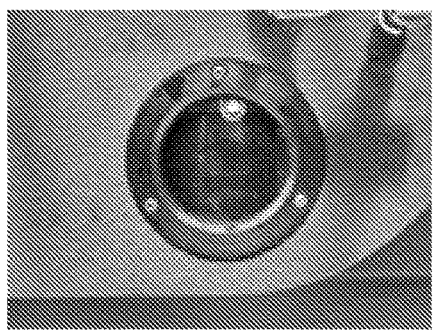
Figure 3E:
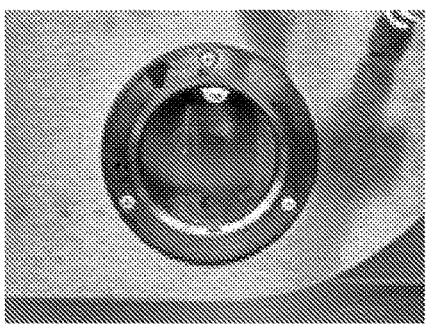
Figure 3F:
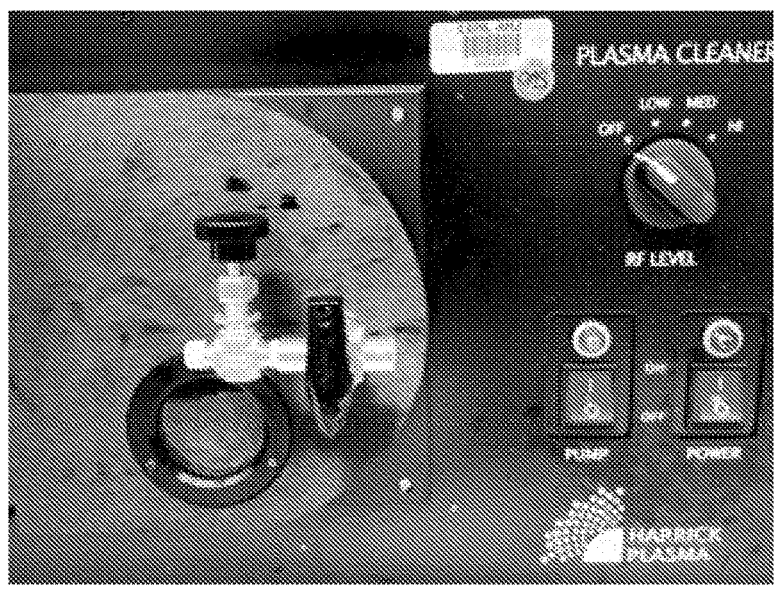

FIGS. 3A-3F show bonding PDMS to microscope slides. FIG. 3A shows punching out the inlet and outlet holes with a 15 gauge needle. A PDMS layer can be placed underneath to ensure a clean punch. FIG. 3B shows placing the PDMS layer and glass in the plasma cleaner with bonding sides facing up. FIG. 3C shows closing the valve, and switching on "Pump" and "Power", and leaving RF level at "OFF." FIGS. 3D-3E show after one minute, turning the "RF Level" to "HI" for 15 seconds. The chamber should go from dark (FIG. 3D) to glowing purple/pink (FIG. 3F). FIG. 3F shows quickly removing glass and PDMS; firmly and evenly press the two layers together around the edges, avoiding the root chamber region.

Altogether, these data demonstrates bonding PDMS layers to microscope slides efficiently and effectively.

Example 3

Molds

This example demonstrates molds for making the PDMS layers.

Figure 4A:
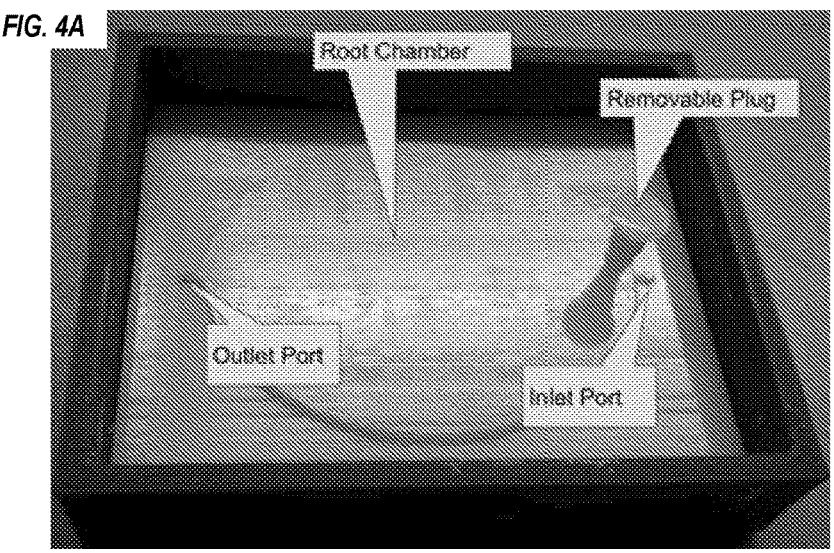
FIGS. 4A-4C show non-limiting exemplary plant growth molds.
Figure 4B:
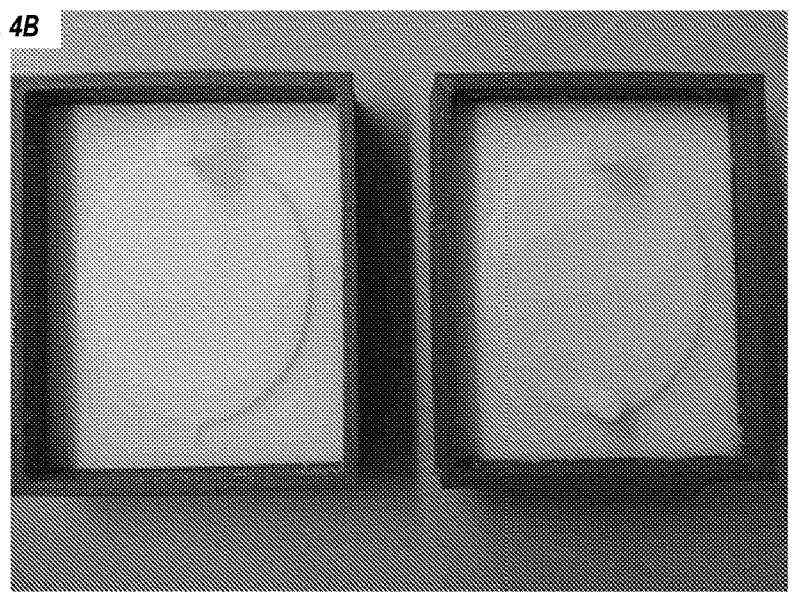
Figure 4C:
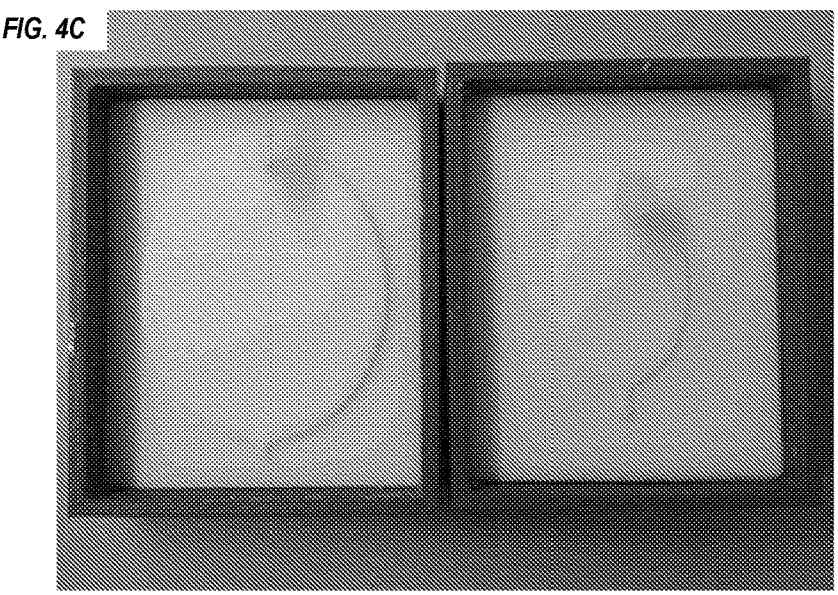

FIGS. 4A-4C show two molds of plant growth devices. FIG. 4A shows a non-limiting exemplary layout of the mold. The removable plug can be removed after the PDMS has been poured and cured, creating a reservoir for the plant shoot to grow out of. FIG. 4B shows the standard mold, on the left, has narrow inlet and outlet ports, while the variant mold on the left has a wide outlet port. The standard mold allows for users to connect flow pumps directly to the plant growth device for precise fluidic control. The variant mold on the left can be helpful when the user wishes to collect root exudates by hand with a pipette or syringe. FIG. 4C shows molds in two sizes. The larger left mold creates a 5 mL root chamber, while the right mold creates a 2 mL root chamber.

Altogether, this example shows molds each with a base piece and a side piece for easy separation of the PDMS layer from the mold.

Example 4

Plant Growth Device Fabrication

This example demonstrates plant growth device fabrication and sterilization.

Protocol 1'. Plant Growth Device Fabrication—Casting PDMS Layers (Embodiment 2)

1.1. Construct the plant growth device molds using 3D printing techniques (the design files are available at ecofab.org. Each mold includes three parts: a casting frame, a featured mold base and an insert, as shown in FIGS. 5A1-5A2, 5B, 5C1-5C2, 5D, 5E1-5E2, and 5F).

Print the mold base and insert out of rigid opaque photopolymers using a 3D plastic printer, utilize a minimum of 100 micron resolution, and print the casting frame with acrylonitrile butadiene styrene (ABS).

1.2. Mix 40 ml of siloxane elastomer base with curing agent in a disposable 1 L container. Depending on the desired experiment (see Protocol 2.1 and 2.2 below in this Example), volume ratios of 5:1 base to curing agent, 15:1, or 30:1 are utilized. For example, for a 5:1 volume ratio, 32 mL of base are mixed with 8 mL or curing agent. Steps 1.3 to 1.8 can be performed for all kinds of mixtures.

Figure 3G:
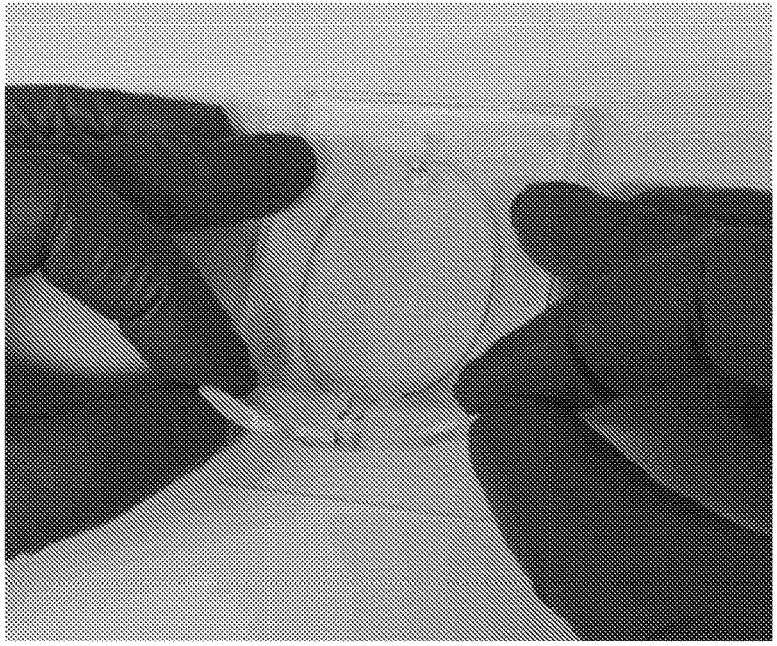

Plant growth device fabrication can include pouring the mixture of elastomer base and curing agent into the mold (FIG. 2C), heating the mold with mixture at 85° C. for 4 h (FIG. 2D), removing the insert from the mold (FIG. 2E), separating the PDMS from the casting frame (FIG. 2F), pushing the mold base out of the casting frame (FIG. 2G), using a knife to separate the PDMS from the mold along the edges (FIG. 2H), peeling the PDMS layer slowly off of the mold base (FIG. 2I), poking holes for both inlet and outlet channels of the standard PDMS layer (FIGS. 3A1-3A2) or poking a hole for the inlet channel of the wide-outlet PDMS layer (FIG. 3A3), rinsing and transferring the PDMS layer (made of a 15:1 elastomer base to curing agent mixture) and a microscope slide into a plasma cleaner for bonding (FIGS. 3B1-3B2), using clamps to hold the PDMS layer (made of a 5:1 elastomer base to curing agent mixture) onto a microscope slide (FIG. 11C), and pressing the PDMS layer (made of a 30:1 elastomer base to curing agent mixture) directly onto a microscope slide (FIG. 3G).

1.3. Place the container in a vacuum chamber for at least 30 min to remove air bubbles from the elastomer mixture.

1.4. Pour the mixture into the assembled 3D printed plastic mold (FIG. 2C) and keep the mold on an 85° C. heating block for 4 h (FIG. 2D).

1.5. Let the mold cool down for 5 minutes. Then pull out the insert from the mold gently (FIG. 2E), and then slowly run a utility knife inserted between the casting frame and PDMS (the solidified elastomer mixture) to separate them (FIG. 2F).

1.6. Press the mold base with PDMS up out of the casting frame (FIG. 2G). Use a knife or other tools to gently separate the PDMS layer from the mold base at the edges (FIG. 2H), and then slowly peel it off from the mold surface (FIG. 2I).

1.7. Create inlet and outlet channels on the PDMS layers by poking ~1.6 mm holes for the inlet and outlet ports with a 15 gauge blunt needle (FIGS. 3A1-3A3).

The standard mold has an inlet and outlet port that needs to be punched out (as shown in FIGS. 3A1-3A2). The wide-outlet mold needs the inlet port to be punched out while the outlet port may not need to be punched out (See FIG. 3A3).

1.8. Use a scissor to trim the edges of PDMS layers.

The trimmed PDMS layers could be ≥approximately 76 mm×51 mm rectangles for small plant growth devices and ≥approximately 102 mm×83 mm rectangles for large plant growth devices.

Protocol 2'. Plant Growth Device Fabrication: Chemically Attaching PDMS Layers onto Microscope Slides 2.1. Permanently bonding the PDMS layers to microscope slides 2.1.1. Rinse the bonding side of the PDMS layer (made of a 15:1 elastomer base to curing agent mixture) and 7.6×5 cm microscope slide with methanol and then blow dry with compressed air or an ultra-pure nitrogen gun.

2.1.2 Place the microscope slide and PDMS layer into a plasma cleaner with their bonding sides facing up (FIGS. 3B1-3B2). If a plasma cleaner is not available, go directly to step 2.2.

2.1.3. Close the chamber and gas vent valve of the plasma cleaner, and turn on the vacuum and pump down the chamber for 1 minute.

2.1.4. Turn on the power of the plasma generator, and switch the radio frequency (RF) level to "HI" for 1 minute.

2.1.5. Turn off both vacuum pump and plasma power, and vent the chamber to atmosphere.

2.1.6. Take out the microscope slide and PDMS layer from the plasma chamber, and quickly press all four edges of the PDMS layer onto the slide with even pressure (FIG. 3G). Make sure the center oval region of the PDMS layer (the root chamber) does not touch the slide.

2.1.7. Place the sealed plant growth device on a 120° C. heating block for 20 min to further secure the permanent bonding between the PDMS layer and the microscope slide.

2.1.8. Let the device cool down for 5 minutes. Trim off the extra edges of the PDMS layer with a knife.

2.2. Reversible physical sealing of the PDMS layers to microscope slides 2.2.1. The reversible sealing technique utilizes a set of custom clamps (either printed by a 3D plastic printer or machined in metal, the drawings are shown in FIGS. 6A1-6A2, 6B1-6B2, and 6C1-6C2).

2.2.1.1. Place the microscope slide into the cutout on the bottom clamp plate, and then align the PDMS layer (made of a 5:1 elastomer base to curing agent mixture) on top of the slide.

2.2.1.2. Place the top clamp plate over the PDMS layer. Secure the top and bottom plates together using four hex cap screws, orienting the screws so that the nuts are threaded on from the top of the clamp.

2.2.2. Adhering PDMS directly to microscope slides 2.2.2.1. Position the PDMS layer (made of a 30:1 elastomer base to curing agent mixture) on top of a microscope slide.

2.2.2.2. Press the PDMS layer to the slide. The soft, very adhesive 30:1 PDMS layer should stick to the slide creating a waterproof seal without the permanent chemical bonding or physical press from a clamp (FIG. 3G).

Protocol 3. Plant Growth Device Sterilization 3.1. Rinse plant growth devices with ultrapure water.

3.2. Place one plant growth device in a plant growth container, and add 70% ethanol until the device is submerged. Close the container lid and shake gently to wet all surfaces inside with ethanol. Make sure the root growth chamber of the plant growth device is filled with ethanol, with very few or no air bubbles.

3.3. After 30 min incubation at room temperature, pour off 70% ethanol, and repeat the incubation with 100% ethanol for 5 minutes.

3.4. Drain out ethanol, and incubate the sterilized plant growth system for 16 h in a laminar flow hood to dry completely. If available, additionally sterilize the system by turning on the UV within hood for 1 h.

3.5. Store the sterilized plant growth systems in a sterile hood or autoclaved bags for future use.

Altogether, the data demonstrates casting a PDMS layer with a mold and bonding PDMS layers to microscope slides to fabricate a plant growth system device.

Example 5

Plant Growth Systems with Independent Growth Light

This example demonstrates using individually controlled LED lights for plant growth devices.

A commercial plant incubator for plant related studies can be expensive. It is also a time consuming process when designing parallel experiments of studying plant responses under different growth conditions with only one plant incubator. In some embodiments, plant growth systems were built with LED growth light strips, which were independently controlled by a TC420 LED controller and allows to adjust the growth light conditions for individual plant.

Unlike a traditional growth chamber, this setup will allow each plant to have a customized light schedule. Nano coated LED grow strips (3:1 red/660 nm to blue/450 nm LEDS, LED World) were attached to the outside of plant growth boxes with silicon LED clips that were glued on the boxes using a hot glue gun. The input channel of a TC420 LED controller (RGBSIGHT, Amazon.com) was connected to a power supply (110-120 V input, 24 V output, LED World) and its output channels were linked to one ends of LED strips. The LED controller was programmed with a Windows software, Pled. Besides adjusting light duration cycles and intensity, the controller also has pulse width modulation functions to enable gradual fades between different brightness levels.

Figure 7:
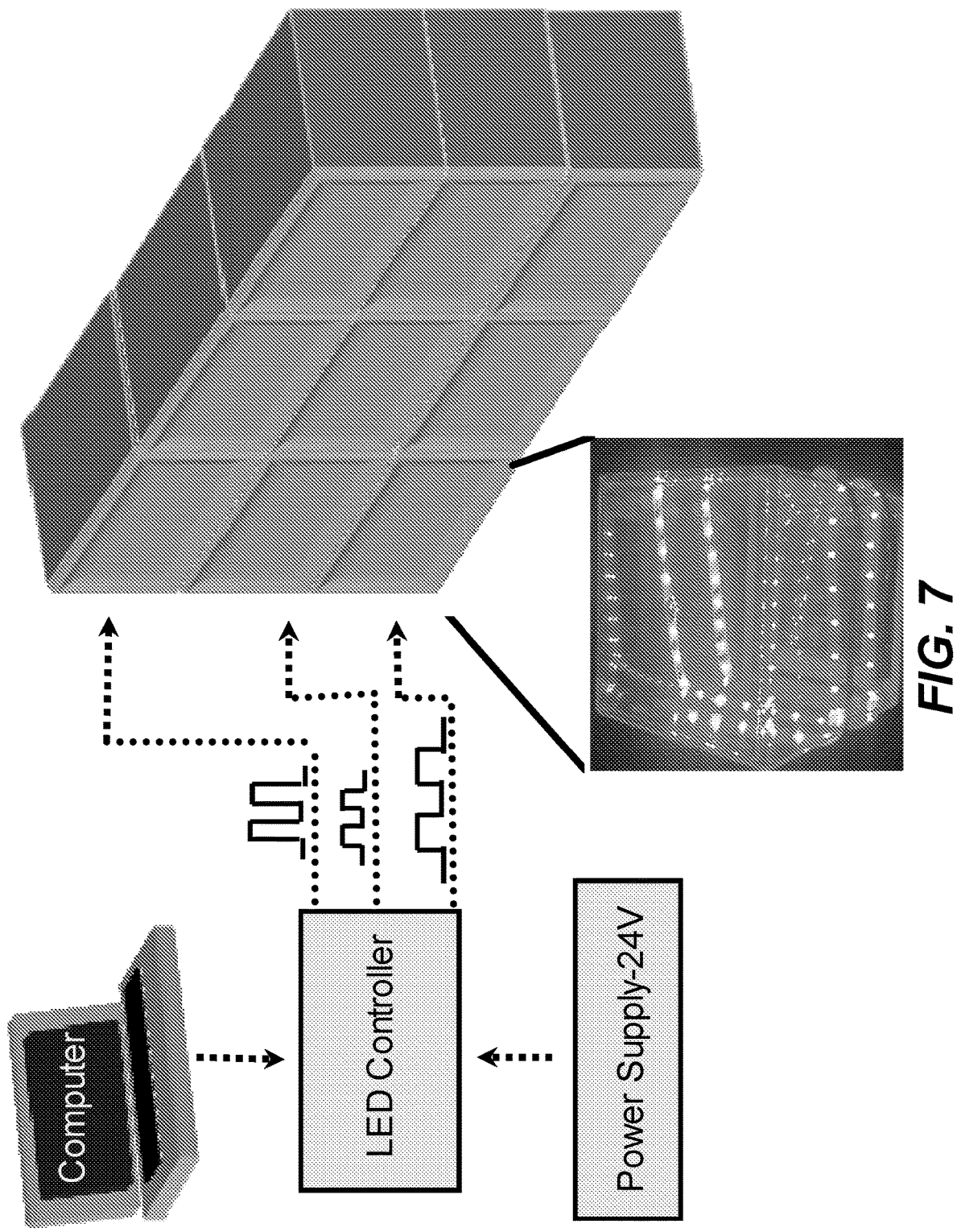

As shown in FIG. 7, the LED controller was programmed with a Windows software, Pled, to output diverse bias signals through each of its output channels that were linked with LED strips attaching outside of plant growth boxes. All the light growth conditions, such as light intensity, cycles and colors, can be adjusted for each plant growth system so various plant studies with different light parameters can be pursued synchronously with a low budget. FIGS. 8A-8D show a non-limiting protocol of installing LED growth lights on a plant growth system. The protocol can include marking out the locations for a number of LED clips in a spiral around the plant growth container (FIG. 8A), attaching LED clips to the plant growth container (FIG. 8B), threading a LED strip through these clips (FIG. 8C), and connecting the LED strip to a controller wired with a 24V power supply (FIG. 8D). FIG. 8E shows a non-limiting exemplary schematic of wire connections to the controller.

Protocol 4. Plant Growth Device with LED Growth Lights 4.1. Attach LED strips onto plant growth containers 4.1.1. Mark out locations on the plant growth container for 9 LED clips. Start with the first clip 120 mm up from the bottom of the container along an edge (FIG. 8A), and proceed to mark out clip locations in a spiral around the container, with each next clip dropping 10 mm. The end result could be a spiral of 9 clips that allows a 1 m LED strip to wrap around the container twice.

4.1.2. Hot glue an LED clip to each marked position by adding two dabs of hot glue onto the container, aligned with where the clips' mounting holes will go. Press the clip holes into these two dabs of glue, then add another dab of glue on top of the holes. Repeat for all clips until 9 clips form a spiral (FIG. 8B).

4.1.3. Thread the LED strip through the clips in a spiral shape, LEDs facing into the container. The strip should circle around twice (FIG. 8C).

4.2. Connecting LED strips to the power supply with a controller (FIG. 8D shows a non-limiting exemplary plant growth container or chamber with illuminated lights, the programming of the controller is described in step 3).

4.2.1. Connect the positive and negative terminals of the power supply to the "INPUT: V+" and "INPUT: V-" terminals of the controller using 2-wire cable (FIG. 8E shows a non-limiting exemplary schematic drawing of the controller setup).

4.2.2. Connect the negative lead from the bare end of a female-to-bare cable to one "OUTPUT" channel on the controller. If five channels on the controller was utilized, up to five 1 m LED strips can be supported.

4.2.3. Connect all of the positive leads of the cables to a compact splicing connector (if more than one channels are needed), and then link this connector to the "OUTPUT V+" terminal of the controller.

4.2.4. Plug each LED strip into the female end of the cables, so each LED has its own channel to be controlled. If desired, use female-to-male cables to extend the reach.

4.3. Programming the controller for a desired light cycle

FIGS. 9A-9F shows a group of plants, three *Brachypodium* and three Switchgrass, were growing under different growth light duration from 8 hours to 16 hours per day. FIGS. 9A-9C show 4 weeks old *Brachypodium* plants grow in the plant growth systems with independent light under different light irradiation time: 8, 12 and 16 hours/day. FIGS. 9D-9F show 4 weeks old Switchgrass plants grow in the plant growth systems with independent light under different light irradiation time: 8, 12 and 16 hours/day.

Altogether, these data demonstrates integrating independent growth light controlled by a controller can enable studying plant responses under different growth conditions with one plant incubator.

Example 6

Growing Plants in Plant Growth Systems

This example demonstrates growing plants in plant growth systems.

Materials and Equipment

1. Sterile Hood
2. Luer-lock Syringes and 15 gauge needles
3. Containers for plant growth devices (Amazon, part #B00P9QVOS2 for large size, part #B005GAQ25Q for small size)
4. Sterile surgical tape (e.g., VWR, 3M Micropore™)

If sterility is required, the following steps can be performed in a sterile flow hood.

Protocol 5. Growing Plants in Plant Growth Devices 5.1. Germinate seeds of interest on agar plates for several days until the seeds are large enough to be put in plant growth systems without the seeds floating away in the root chamber (2 days for the case of *B. distachyon*, 7 days for *P. virgatum*).

5.2. Rinse plant growth chips or devices to be used with milli-Q filtered water.

5.3. Place one chip in each container, and add 70% ethanol until chip is submerged. Close container lid and shake gently to wet all surfaces inside with ethanol. Make sure the chip's root chamber is fully filled with ethanol, with no air bubbles. Allow to soak for 30 minutes.

5.4. Pour off 70% ethanol, and do a second soak with 100% ethanol for 5 minutes.

5.5. Pour off 100% ethanol and allow chips and containers to air-dry completely (usually overnight). UV sterilize as well if desired.

5.6. Using a syringe and 15 gauge needle (or micropipette), flush the device's root chamber three times with growth media.

5.7. Fill the chip root chamber with growth media.

5.8. Using tweezers, place a single seedling into the seedling reservoir. The root should be fully submerged into the root chamber, with the shoot sticking out of the reservoir.

5.9. Add 2-5 mL of sterile water into the container, but not in the plant growth device. This will help increase humidity and reduce evaporation of medium from the root chamber.

5.10. Close the container. If sterility is required, seal the lid with micropore tape.

5.11. Place it into an incubation chamber.

5.12. Periodically check on plant growth systems to refill media and add water to the container. Adding media may get progressively difficult as the plant develops its root system.

For the standard chip, tilt the chip and gently tap it on the table to knock air bubbles up toward the plant stem side. Maintain this angle and add media through the outlet channel (the port on the bottom), allowing air to escape around the plant stem. For the wide-port chip, tilt so that bubbles float up to the wide port, then add medium into the wide port end. Experiment to see what works best for your plant system.

Protocol 5'. Growing Plants in Plant Growth Devices 5.1. Seed sterilization and germination The seed sterilization and all following steps with seedlings have to be performed in sterile conditions.

The sterilization process discussed below is suitable to the seeds of *Arabidopsis thaliana, Avena barbata, Brachypodium distachyon* and *Panicum virgatum*. *Panicum virgatum* seeds should be suspended in 60% sulfuric acid for 1 h before the sterilization process. It is advised to prepare 1-2 seeds per plant growth device, taking into account the germination rate and the homogeneity of germination.

5.1.1. Soak the seeds in 70% ethanol for 2 minutes.

5.1.2. Remove ethanol with a pipette, and rinse the seeds with sterile water three times.

5.1.3. Leave the seeds in 10% bleach solution for 5 minutes.

5.1.4. Remove the bleach solution, and thoroughly wash the seeds using sterile water three times.

5.1.5. Add sterile water to the seeds, and incubate the microcentrifuge tube in a 4° C. refrigerator for 7 days.

5.1.6. Evenly spread the seeds on 0.5 Murashige & Skoog (MS) medium with 0.6% phytagel and seal the plates with micropore tape.

5.1.7. Grow the plants to a root length of about 5 mm for transfer to plant growth devices (FIG. 10A). For the experiments presented here, a 16 h light/8 h dark illumination regime in a 22° C. growth chamber was applied, and plants were incubated 2-7 d before transfer to plant growth devices (2 days for *Avena barbata* and *Brachypodium distachyon*, 7 days for *Arabidopsis thaliana* and *Panicum virgatum*).

5.2. Transferring seedlings into plant growth devices with liquid medium (FIGS. 10B-10C)

5.2.1. Using a sterile syringe or micropipette, flush the root chamber of a plant growth device with sterile water for three times, and then fill the root chamber with the growth medium of interest, for example 0.5 MS medium (FIG. 10B, see step 5.1.6).

5.2.2. Insert a single seedling into the plant reservoir of the plant growth device (FIG. 10C). The root can be fully submerged inside the root chamber, with the shoot sticking out of the reservoir.

5.2.3. Add 3 mL of sterile water into the container, avoiding the device. This will increase humidity and reduce evaporation of medium from the root chamber.

5.2.4 Close the container, and seal the lid with micropore tape (FIG. 10D).

5.2.5. Place the plant growth device into a plant incubator, or utilize the plant growth illumination system in a controlled temperature environment suitable for the growth of the respective plant (see Protocol 4 in Example 4). For the data presented here, the chamber was set to 24° C.

5.2.6. Periodically check on plant growth devices to refill growth media inside the root growth chamber and add water to the container. All steps should be performed in sterile conditions. For early plant growth stages, refilling of the root growth chamber (or root chamber) can occur every 5 to 7 days. For later growth stages, a refilling can occur every 2 to 3 days.

If desired, use a syringe or pipette to collect root exudate solution from the root growth chambers into a microcentrifuge tube and store it in a −80° C. freezer; also, image the root morphology with a gel imager or microscope.

5.3. Transferring seedlings into plant growth devices with solid substrates 5.3.1. Use root chambers fabricated with a 5:1 elastomer base to curing agent mixture if using a set of custom clamp to attach it to a microscope slide (FIGS. 11C, 6A1-6A2, 6B1-6B2, and 6C1-6C2); or choose a PDMS layer made of 30:1 base to curing agent mixture if adhering PDMS layers to slides directly (See Protocol 2.2 in Example 4).

5.3.2. Sterilize the plant growth containers or chambers, as described in Protocol 3 in Example 4.

5.3.3. Add sterilized soil/sand into the root chamber: turn the PDMS layer upside down, and add the substrate to the root chamber. Avoid any particulate fall on the area that will be in contact with the microscope slide, since this will reduce adhesion.

5.3.4. Place the microscope slide on top of the PDMS layer, and press all the edges firmly. Flip the plant growth device so that no soil/sand falls out of the reservoir opening. For plant growth devices made of a 5:1 base to curing agent mixture, a custom clamp can be used to secure the seal.

5.3.5. Flow liquid medium or water through the inlet or outlet channel of the plant growth device, and transfer a seedling into its plant reservoir, as described in Protocol 3.3 in Example 4.

5.4. Adding microbes into plant growth devices 5.4.1. Transfer a microbial colony to an incubation tube with 8 mL LB broth, and grow it to OD 0.5 (approximately 12 h).

5.4.2. Transfer the culture solution into a 15 mL centrifuge tube, and centrifuge it at room temperature for 5 min at 3000×g to pellet microbes.

5.4.3. Remove supernatant, and add 8 mL of plant growth medium used in the target plant growth device. Suspend the pellet of microbes, and centrifuge the tube at room temperature for 5 min at 3000×g.

5.4.4. Repeat step 5.4.3 two times to completely remove any LB nutrient traces.

5.4.5. Add plant growth medium to the washed microbe pellet until its optical density is about 0.5 at 600 nm incident light.

5.4.6. Add 20 μL of the microbe solution into the root chamber through the plant growth outlet. The strains used in this publication traveled to plant roots within 2-3 days, and started colonizing root surfaces.

5.4.7. For engineered chemiluminescent microbes (such as *Pseudomonas* WCS 417, *Pseudomonas* 2-79, *Pseudomonas* Q8r1 and *Ralstonia* sp. UNC404CL21), make sure to include the inducer (1 mM IPTG) in plant growth medium to induce luciferase expression.

FIGS. 10A-10D show growing plants in plant growth systems. FIG. 10A shows *Brachypodium* seeds that had been germinated for two days and are ready for transferring to plant growth systems. FIG. 10B shows after rinsing 3 times, filling root chamber with growth media. FIG. 10C shows using tweezers, inserting root end of seedling into the plant reservoir without damaging the root or shoot. FIG. 10D shows adding 2-5 mL (2 ml for small plant growth systems, 5 ml for large plant growth systems) of water into the bottom of the container, then close and seal the lid with Micropore tape.

Altogether, these data demonstrates using plant growth systems to grow plants by planting germinating seeds that are sufficiently large into root chambers.

Example 7

Metabolite Profiling of Root Exudates from Plant Growth Systems

This example shows an exemplary protocol for metabolite profiling of root exudates from plant growth systems
Protocol 6. Metabolite Profiling of Root Exudates from Plant Growth Devices 6.1. Sample preparation for LC/MS based metabolomics analysis 6.1.1. Put the microcentrifuge tubes with root exudates collected from plant growth devices in a lyophilizer, and turn on the lyophilizer to remove all the water from the tubes.

6.1.2. Add 300 µL LC-MS grade methanol into each tube, and sonicate for 30 min.

6.1.3. Place the tubes in a centrifuge, and centrifuge them at 3000×g for 5 min.

6.1.4. Transfer the supernatant solutions into new microcentrifuge tubes, and evaporate methanol in a vacuum concentrator.

6.1.5. Add 150 µL methanol with 1 mM LC-MS internal standards into each tube, and incubate the tubes in a 4° C. refrigerator for 12 h.

6.1.6. Centrifuge the tubes at 3000×g for 5 min, and transfer the supernatant into 0.22 µm filter tubes.

6.1.7. Centrifuge the filter tubes, and transfer the filtered solutions into 2.0 mL LC/MS vials with 200 µL inserts.

6.1.8. Place the vials inside a LC/MS rack, and load the rack inside the LC/MS auto-sampler.

6.2. Data analysis 6.2.1. Access Metabolite Atlas and custom Python scripts or use other data analysis software.

6.2.2. Identify metabolites based on m/z values, retention time and compound fragmentation patterns using a library of metabolite standards.

Example 8

Plant Growth Systems Used with NIMS Imaging

This example demonstrates using plant growth systems with NIMS imaging.

NIMS imaging has become an effective tool to visualize the spatial distributions of metabolite compositions across cells, biofluids and biological tissues. An approach was developed for integrating plant growth systems with NIMS techniques to locate specific positions of diverse metabolites released from root systems.
Protocol 7. Mass Spectroscopic Imaging of Plant Roots in Plant Growth Devices Plant growth devices made of a 5:1 elastomer base to curing agent mixture with custom clamps (FIG. 12A) were used for root stamping onto nanostructure-initiator mass spectrometry (NIMS) chips, since PDMS layers can be reversely bonded to the surfaces of NIMS chips.

7.1. Sterilize a NIMS chip surface with UV light for 1 h.

7.2. Pick a plant growth device with a growing plant from the incubator, and place it in a sterile hood.

7.3. Open up the plant growth container, and remove the top plate of the clamp.

Figure 12B:
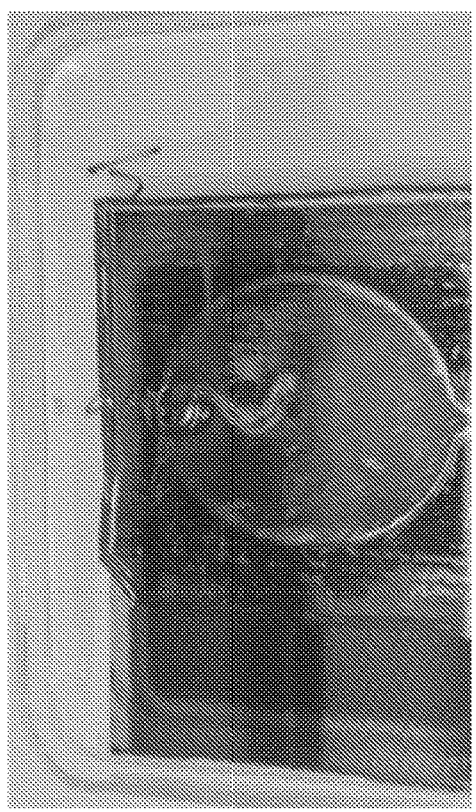
Figure 13A:
FIGS. 13A-13D show an exemplary integration of plant growth systems with NIMS imaging technique.
Figure 13B:
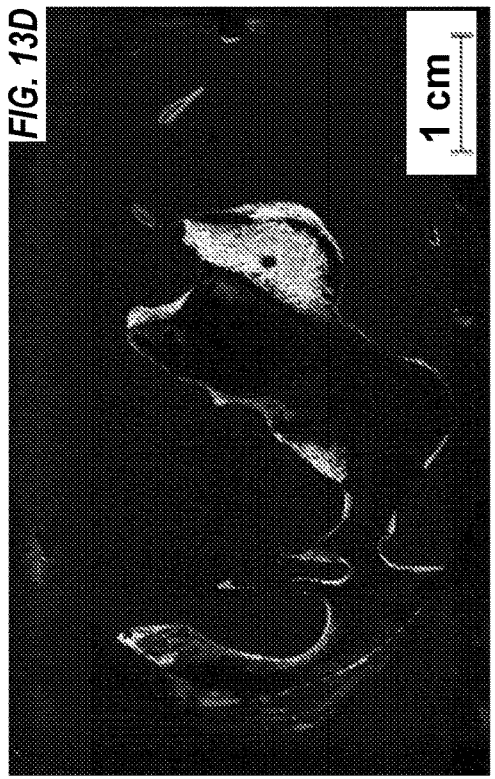

7.4 Lift up the PDMS layer together with the plant inside, and attach the PDMS layer with the plant onto a NIMS chip (FIGS. 12B, 12D, 13B). Once the root touches the NIMS chip surface, it should not be moved. This prevents "smearing" of the root metabolites.

7.5. Gently press down on the roots through the PDMS layer until the roots fully contact the NIMS surface. Leave the roots on the NIMS surface for 20 min.

7.6. Lift off the PDMS layer including the plant from the NIMS chip, again avoiding moving the root across the NIMS surface. Return the plant to the clamp if desired.

7.7. Attach the NIMS chip onto a custom MALDI plate and load the plate into a MALDI spectrometer for mass imaging (FIG. 12C).

7.8. Use OpenMSI program to generate the NIMS image of root metabolites (FIGS. 12D-12E, 13A-13D).

Figure 12C:
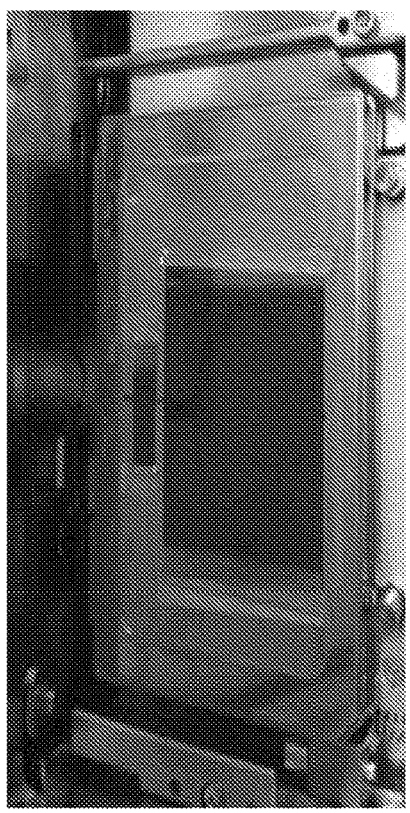
Figure 12A:
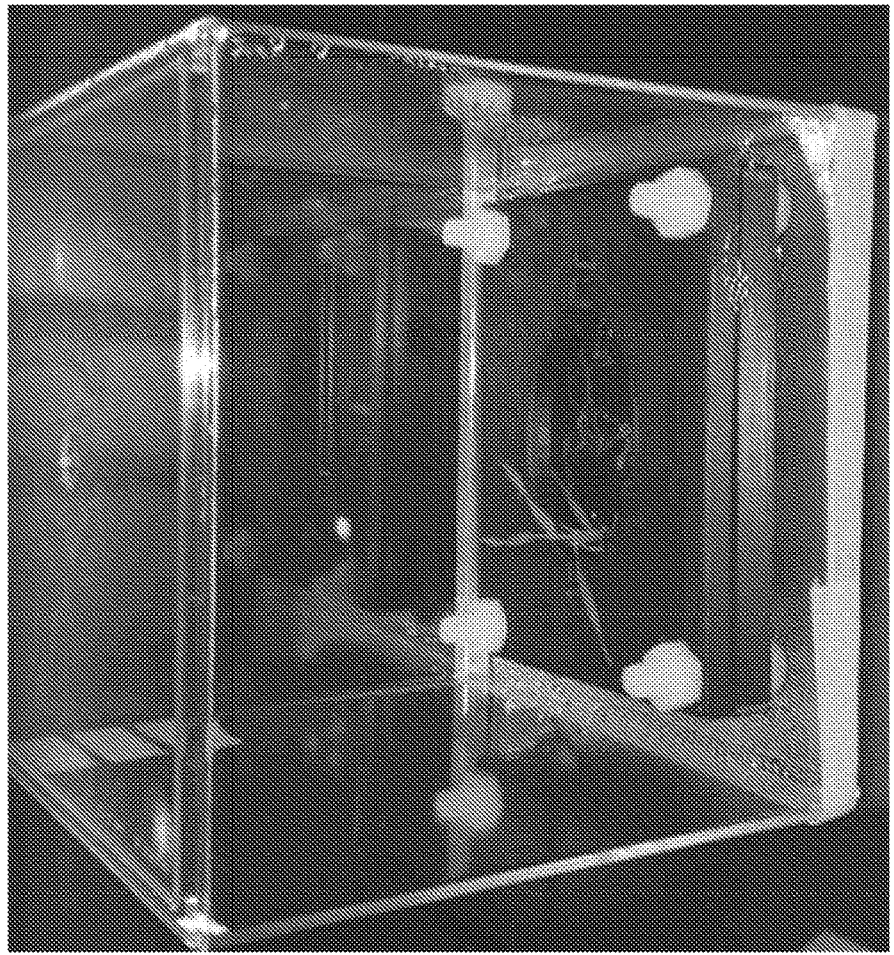

FIGS. 12A-12E show NIMS imaging of plant roots in plant growth devices. FIG. 12A shows *Brachypodium distachyon* growing in a sterile plant growth device placed in a plant growth container or chamber. FIG. 12B shows attaching the PDMS layer with the plant onto a NIMS chip for 20 minutes. FIG. 12C shows using copper tape to attach the NIMS chip onto a custom MALDI plate, and loading it into a MALDI mass spectrometer. FIGS. 12D-12E show one seven-day old *Brachypodium distachyon* plant used for NIMS imaging (FIG. 12D) and the corresponding NIMS image (FIG. 12E). FIG. 12D shows the plant growth PDMS layer with the plant was removed from the clamp and then attached onto a NIMS surface, and FIG. 12E shows a NIMS image of the plant root.

PDMS layers with more rigid textures were fabricated using 5:1 siloxane base/Pt-based catalyst mixtures, and they were sealed onto microscope slides with a set of custom clamps for growing plants as regular plasma sealed plant growth devices (FIG. 12A). PDMS layers with plants were separated from microscope slides and then were attached onto NIMS surfaces for 20 minutes to ensure sufficient metabolites deposited on NIMS surfaces (FIG. 12D). After metabolite stamping, PDMS layers with plants were assembled back onto microscopic slides with clamps, and root growth chambers were refilled with plant growth medium for plants. FIG. 12E shows an example of root NIMS images from a 7 days old *Brachypodium*, and various metabolites were detected along plant roots. NIMS imaging of *Brachypodium* roots at different growing stages (7, 10, 20 days old, FIG. 13A-13D) indicate the changed metabolite profiles from root exudates, which was in agreement with the LC-MS analysis in FIG. 25.

Figure 13C:
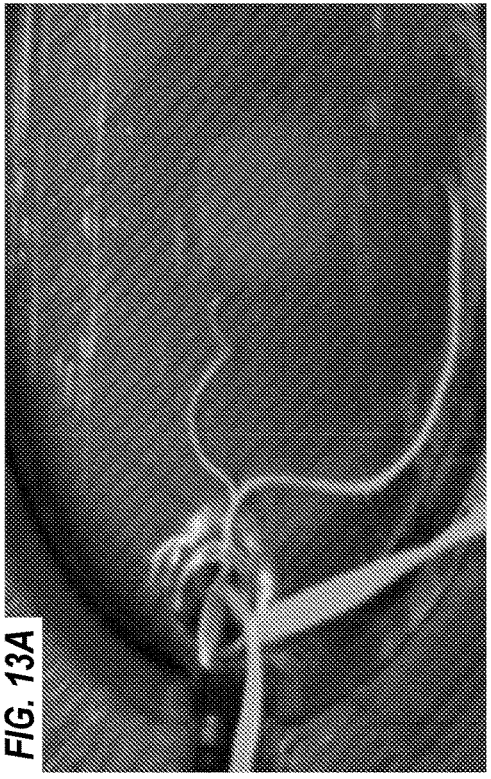
Figure 13D:
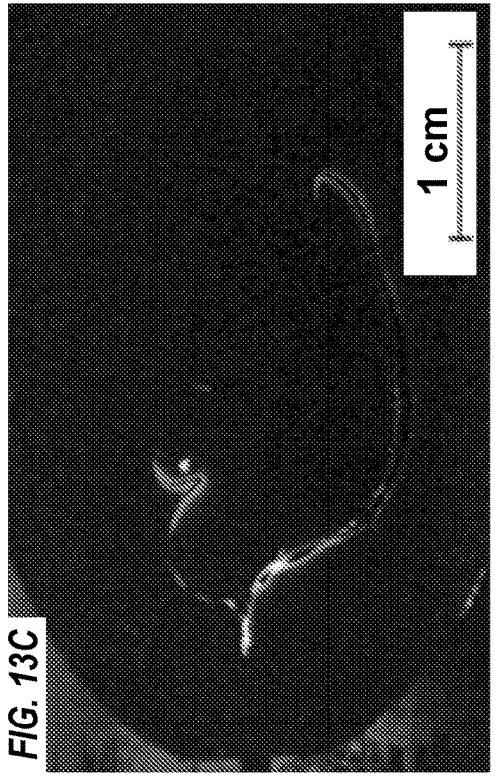

FIGS. 13A-13D show the integration of plant growth systems with NIMS imaging technique. FIG. 13A shows a 10 days old *Brachypodium*. FIG. 13B shows a 20 days old *Brachypodium*. FIGS. 13C-13D show the NIMS images of the root systems from these two plants in FIGS. 13A-13B, respectively. FIGS. 13B and 13D show one 20-day old *Brachypodium distachyon* plant used for NIMS imaging (FIG. 13B) and the corresponding NIMS image (FIG. 13D). The predominant ions are shown in different shadings.

Altogether, these data demonstrates the plant growth systems can be used with NIMS imaging by removing the PDMS layer from a corresponding microscope slide and attaching the PDMS layer with a NIMS surface for metabolite stamping.

Example 9

Integration of Plant Growth Systems with NIMS Imaging

This example shows using plant growth devices in conjunction with nanopore initiated mass spectrometry (NIMS) to "image" root systems of plants.

A 5:1 elastomer base to curing agent can be used for the PDMS layer, which can be reversely bonded to a NIMS chip (a higher-ratio PDMS layer, such as 10:1 base-curing agent, can form permanent bondings with NIMS surfaces). Using a clamp allows one to easily separate the PDMS from the glass slides without disturbing plant root systems. The PDMS layer with plants can then be transferred onto a NIMS chip, and metabolites from roots can be spatially sorbed onto NIMS surfaces.

Materials and Equipment
1. NIMS chips (Northen Lab)
2. 3D printed two-piece clamps (STL files available from Northen Lab)
3. ¼-20×¼ hex cap PTFE screw and nuts
4. Laser desorption ionization mass spectrometer (AB-Sciex 5800 MALDI TOF/TOF)

Protocol 7'. Mass Spectroscopic Imaging of Plant Roots in Plant Growth Devices 7.1. Make a small-sized PDMS layer, using a 5:1 ratio of elastomer base to curing agent. The cured PDMS should be firmer and less sticky than the 10:1 version. Trim the PDMS layer to fit on a 2"×3" glass slide.

7.2. Sterilize the trimmed PDMS layer, a cleaned 2"×3" glass slide, and the top and bottom clamp plates in a large plant growth container by soaking in 70% ethanol for a½hour, then 100% ethanol for 5 minutes. Allow to air-dry completely overnight.

7.3. Rinse the glass slide and PDMS layer with growth media 3 times.

7.4. Assemble the clamp. Place the glass slide into the cutout on the bottom plate of the clamp. Place the PDMS layer on top of the glass slide. Place the top plate of the clamp over the PDMS layer. Secure the top and bottom plates together using for hex cap screws, orienting the screws so that the nuts are threaded on from the top of the clamp.

7.5. Fill the root chamber with growth media, and place a germinated seed into the root chamber.

7.6. Place the clamp setup into a plant growth large container, orienting the container so that the lid is on bottom. This allows easier access to the plant when opening the container.

7.7. Add 2-5 mL of sterile water into the bottom of the container. This increases humidity and prevents evaporation of the growth media.

7.8. After one week of growth, drain out the growth media, undo the clamps, and lift the PDMS layer with the plant and roots off of the glass slide.

7.9. Transfer the PDMS with the plant onto a NIMS chip, so that the roots are evenly distributed across the NIMS chip. When place the roots onto the NIMS chip, minimize repositioning of the roots; Once the root touches the NIMS chip surface, it should not be moved. This prevents "smearing" of the image.

7.10. Gently press down on the roots through the PDMS layer until the roots fully contact the NIMS surface. Liquid adhesion should help hold the roots to the NIMS chip.

7.11. Let roots sit on surface of NIMS chip for 20 minutes.

7.12. Lift off the roots and PDMS layer from the NIMS chip, again avoiding any smearing. The plant can be returned to the clamp if desired.

7.13. Attach the NIMS chip onto a custom MALDI plate and then load the plate into a MALDI spectrometer for metabolite mass imaging requisition.

FIGS. 11A-11E show integration of plant growth systems with NIMS imaging.

Figure 11A:
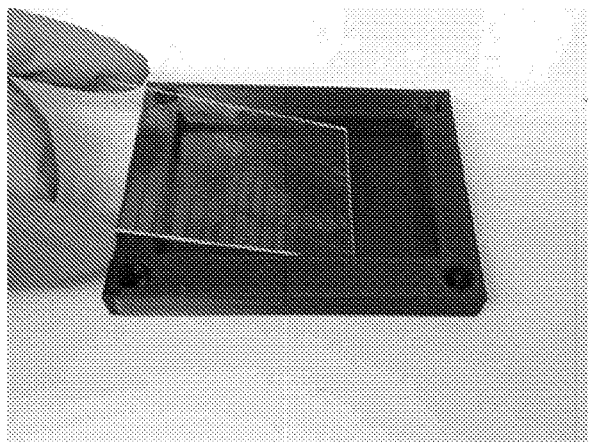
FIGS. 11A-11E show an exemplary integration of plant growth systems with NIMS imaging.
Figure 11B:
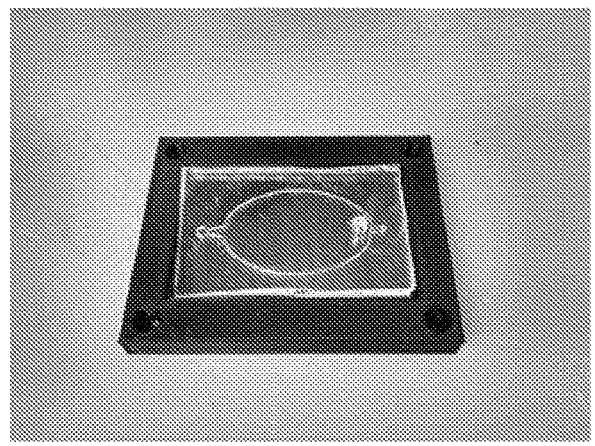
Figure 11C:
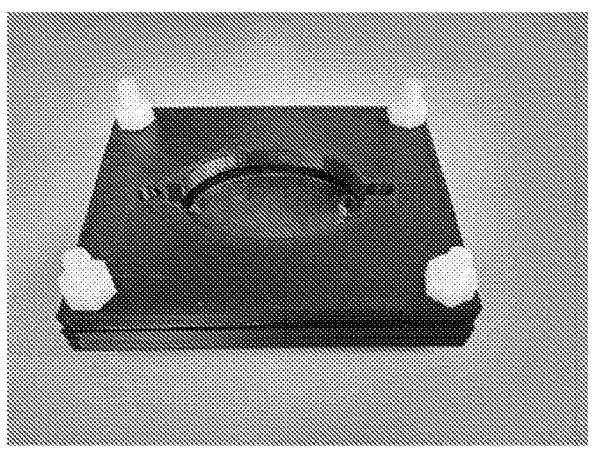
Figure 11D:
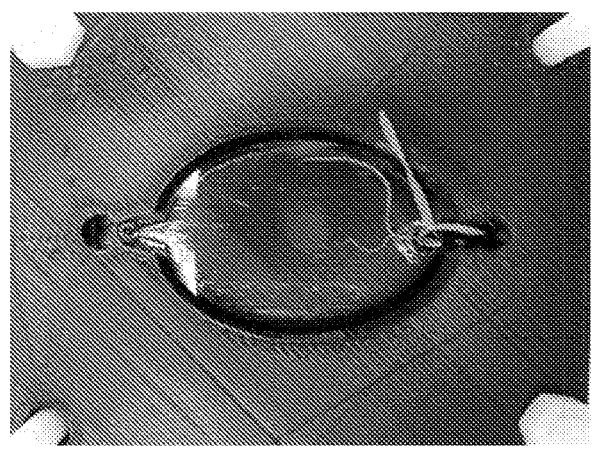
Figure 11E:
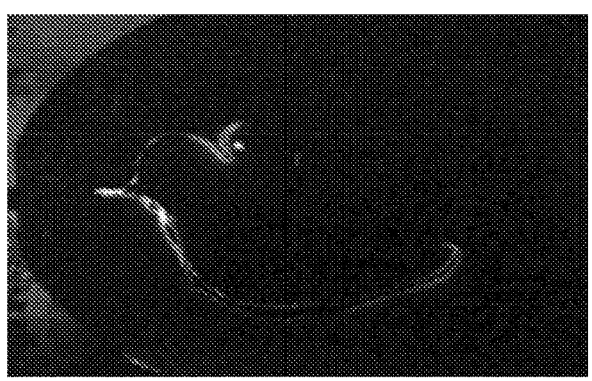

FIG. 11A shows inserting a clean glass slide into the bottom plate of the clamp. FIG. 11B shows placing a PDMS layer on top of the glass, so that a root chamber is formed. FIG. 11C shows adding the top plate of the clamp and fasten with screws. FIG. 11D shows growing *Brachypodium distachyon* in the plant growth clamp. FIG. 11E shows an example of plant root NIMS imaging.

Altogether, these data demonstrates using plant growth systems with NIMS imaging by attaching a PDMS layer removed from a glass slide with a NIMS surface for metabolite stamping.

Example 10

Design of Plant Growth Systems

This example demonstrates designs of plant growth systems each with a plant reservoir, a flow inlet for medium injection and an outlet for metabolites collection. The plant reservoir can be sandwiched between a glass substrate and a PDMS layer.

Each plant growth system can include a plant growth device and a plant sized transparent plastic box. The plant growth device can be designed with a trapezoid shaped plant reservoir, a ¹⁄₁₆" flow inlet for medium injection and a ¹⁄₁₆" outlet for metabolites collection. The dimensions of the plant reservoir can be 4 mm for its top opening and 2 mm for its bottom opening. This design can reduce the chance of flow leakage during liquid injection and also ensures enough space required by plant growth.

Figure 14A:
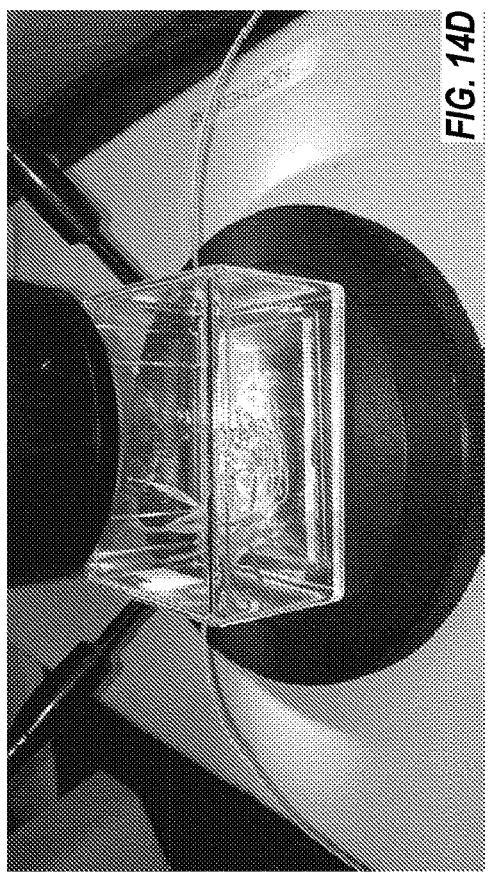
FIGS. 14A-14E show a non-limiting exemplary schematic of a plant growth system and its integration with microscope stations for real-time imaging.
Figure 14B:
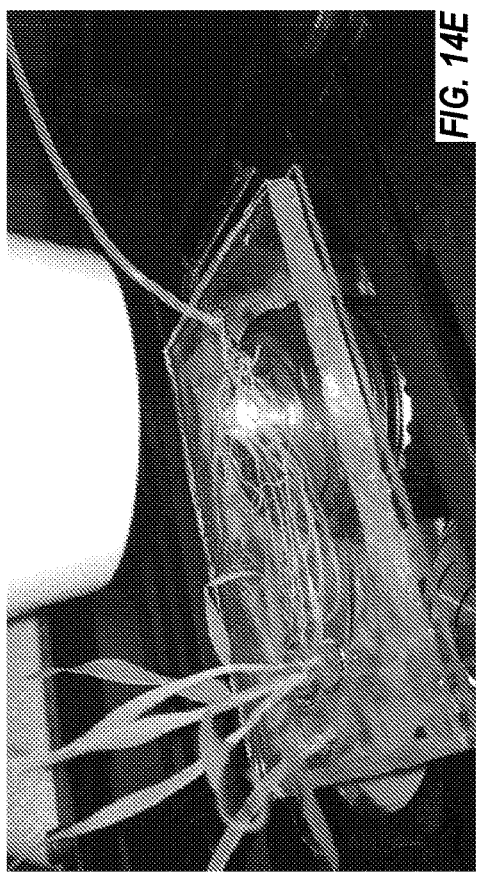
Figure 14C:
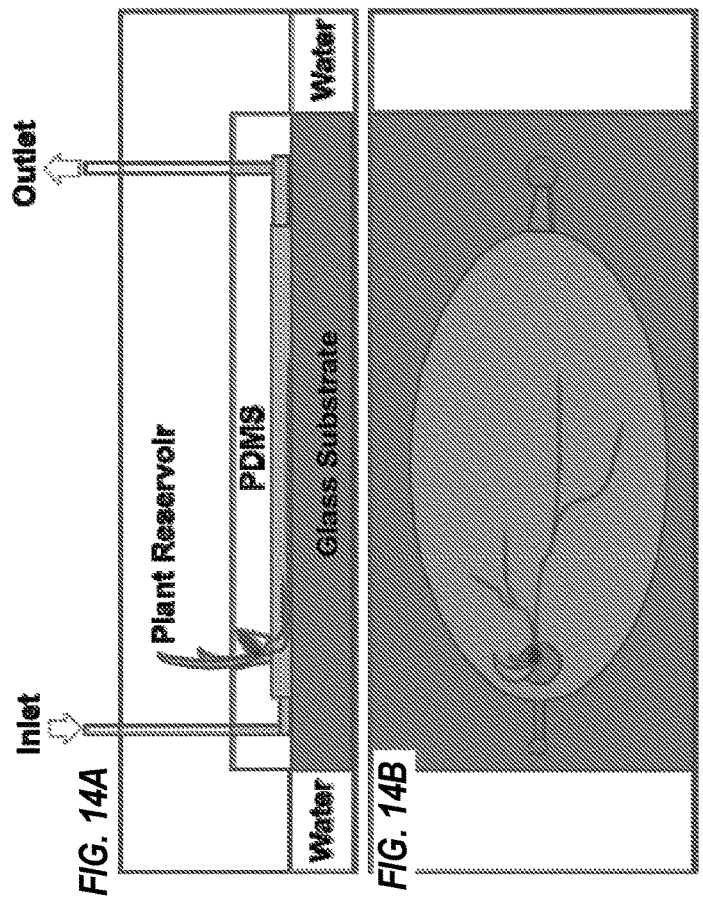
Figure 14D:
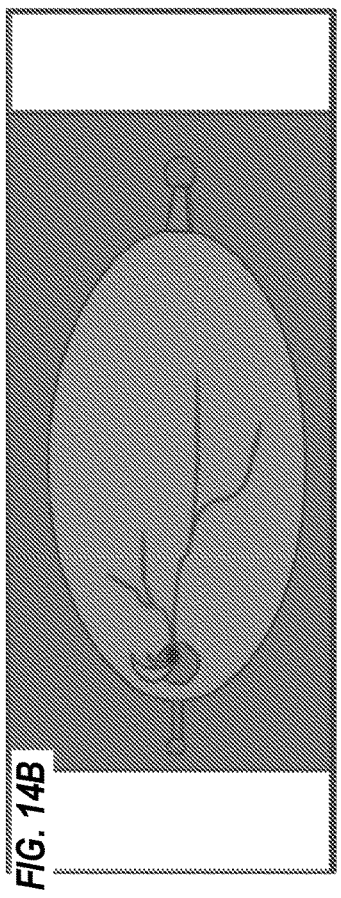
Figure 14E:
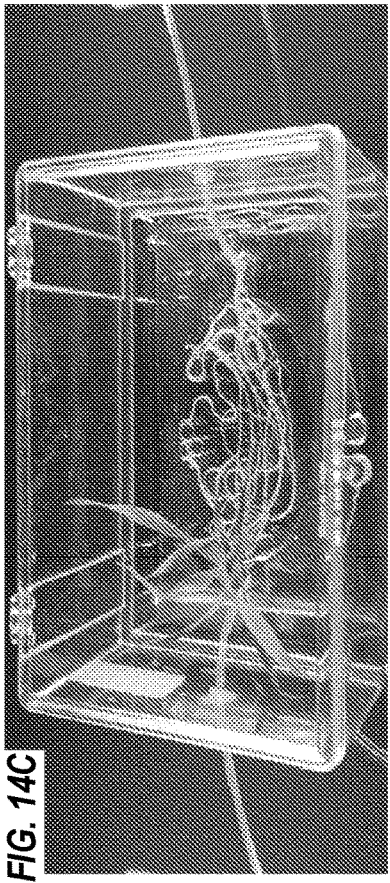

FIGS. 14A-14E show a non-limiting exemplary schematic of a plant growth system and its integration with microscope stations for real-time imaging. FIG. 14A shows a non-limiting exemplary side view of plant growth designs. FIG. 14B shows a non-limiting exemplary top view of plant growth designs. FIG. 14C shows a *Brachypodium distachyon* growing in a plant growth system. FIG. 14D shows direct observation of root growth from a long work distance microscope setup. FIG. 14E shows direct observation of root-microbe interactions from a high resolution microscope setup.

As shown in FIG. 14A, a plant growth device was placed inside a box with drilled holes on the sides so that PTFE tubes can connect with both inlet and outlet channels. The plant root growth chamber of the plant growth device had an oval shape with 1.5 mm depth that can fit the root systems of many model plants, as shown in FIG. 14B. FIG. 14C shows an example of a three weeks old *Brachypodium distachyon* growing in a plant growth system with PTFE tubes connected to its inlet and outlet channels. A plant growth system can be used for integrating both low and high resolution microscopic setups for capturing plant root growth (FIGS. 15A1-15A18) and root-microbe interactions (FIGS. 15B1-15B18), as shown in FIGS. 14D and 14E, respectively.

Figures 16A, 16B:
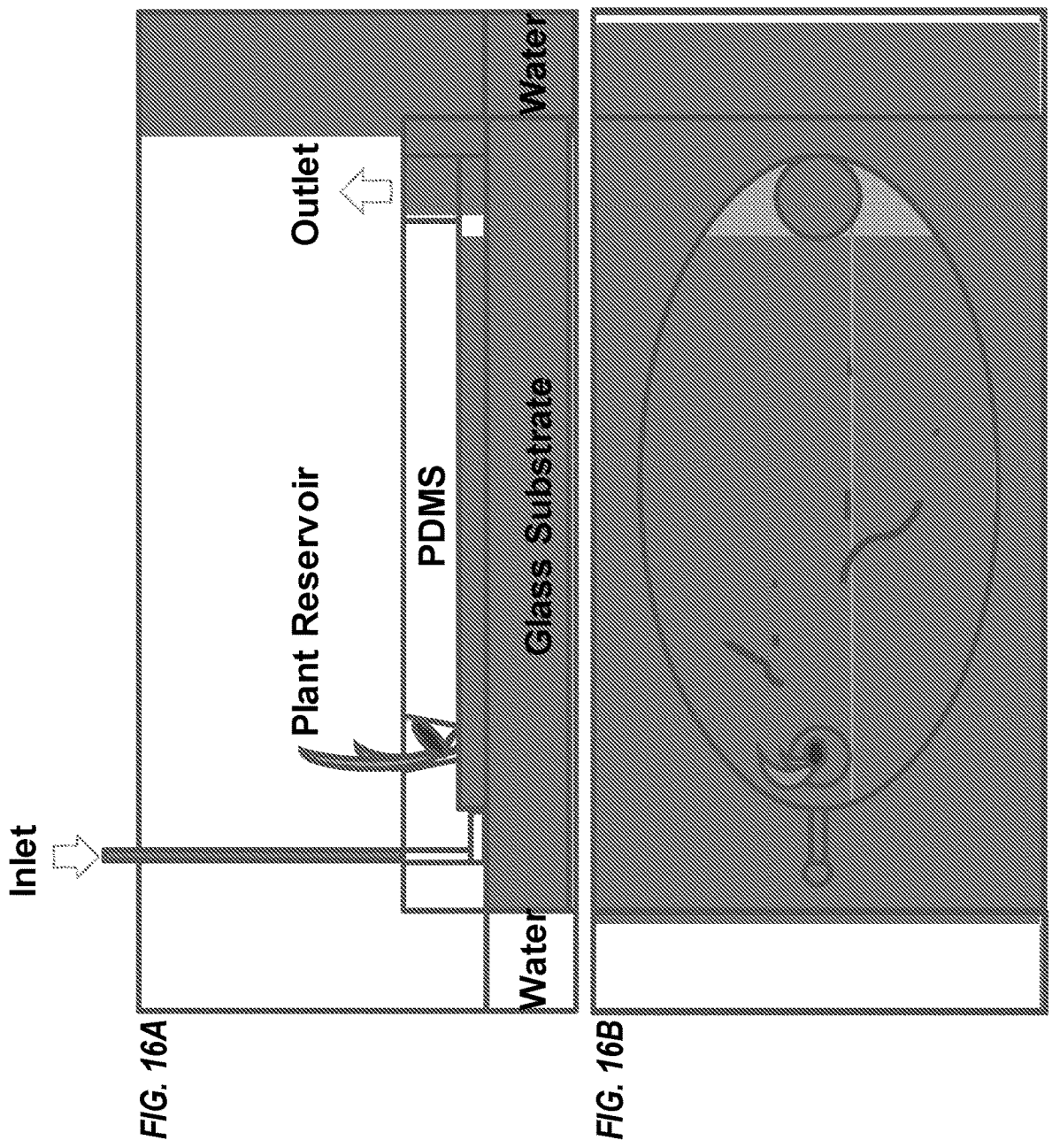
FIGS. 16A-16B show an non-limiting exemplary schematic of a plant growth system with an open outlet channel of 8 mm diameter.

Another design of plant growth devices (FIGS. 16A-16B) can have a wide outlet channel with 8 mm diameter to reduce flow resistance of the outlet. This design can be used when growing plants with thicker root systems. FIGS. 16A-16B shows another non-limiting exemplary schematic of plant growth systems with an open outlet channel of 8 mm diameter. FIG. 16A shows a non-limiting exemplary side view of a plant growth system design. FIG. 16B shows a non-limiting exemplary top view of a plant growth system design. The open outlet design shown in FIGS. 16A-16B can facilitate long term root exudates collection.

Altogether, these data demonstrates integrating a plant growth system with low and high resolution microscopic setups for capturing plant root growth and root-microbe interactions.

Example 11

Plant Growth Systems Used in Various Plant Species and Forms of Growth Media

This example demonstrates using plant growth systems for growing *Arabidopsis, Brachypodium* and switchgrass using liquid and solid growth media.

Figure 17C:
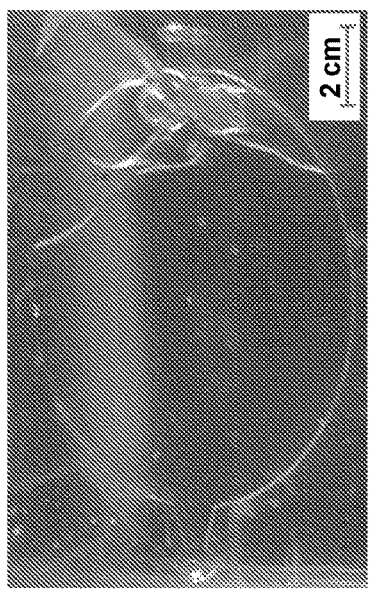
FIGS. 17A-17F show an application of plant growth systems in growing model plants with different forms of media.
Figure 17B:
Figure 17A:
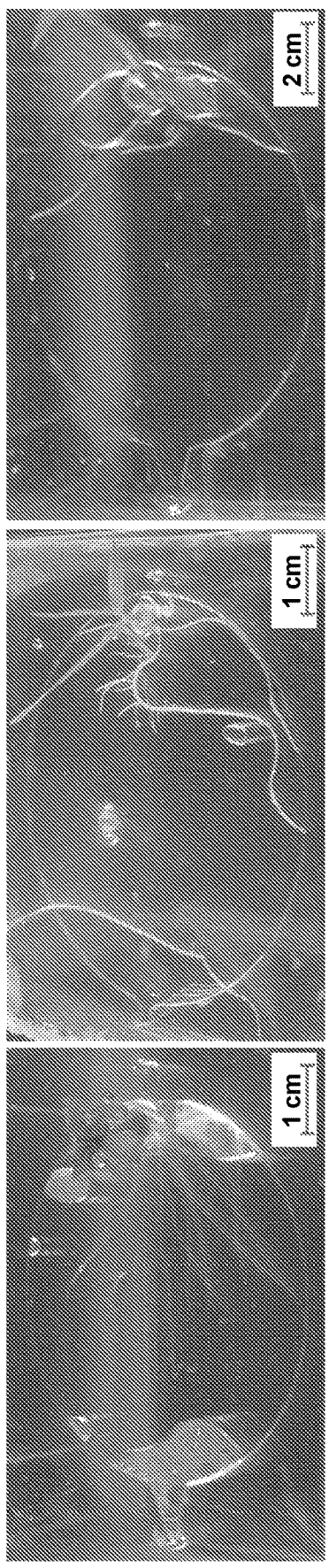
Figure 17F:
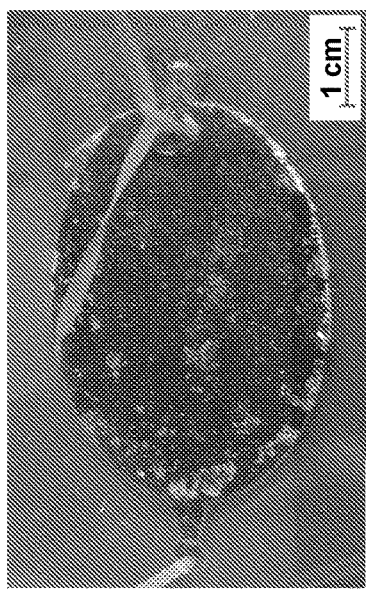
Figure 17E:
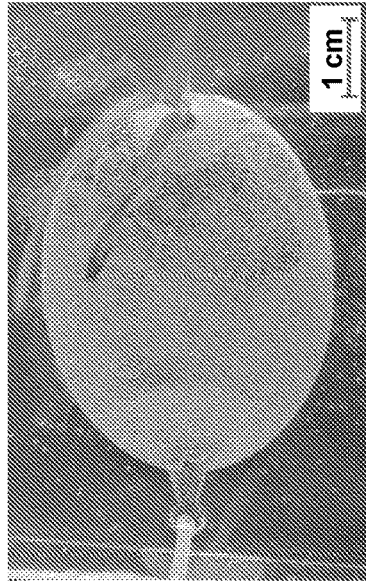
Figure 17D:
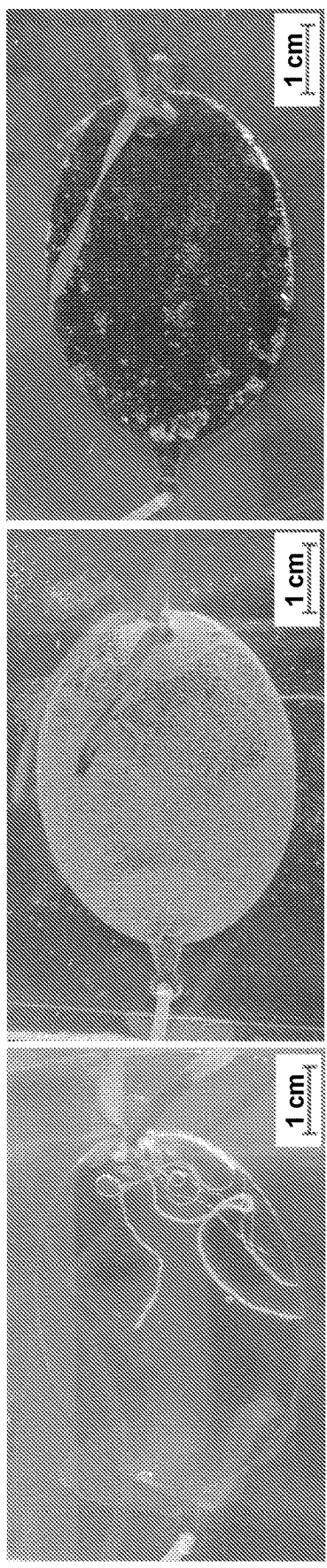

Three types of model plants, *Arabidopsis, Brachypodium* and switchgrass, were used to examine the plant growth system as a general platform in studying different plant species. FIGS. 17A-17F show the applications of plant growth systems in growing model plants with different forms of media. FIG. 17A shows a non-limiting exemplary photograph of 7 days old *Arabidopsis* grown in Murashige & Skoog (MS) salt solution. FIG. 17B shows a non-limiting exemplary photograph of 7 days old *Brachypodium* in MS salt solution. FIG. 17C shows a non-limiting exemplary photograph of 7 days old Switchgrass in MS salt solution. FIG. 17D shows a non-limiting exemplary photograph of 14 days old *Brachypodium* in MS salt solution. FIG. 17E shows a non-limiting exemplary photograph of 14 days old *Brachypodium* in sand medium. FIG. 17F shows a non-limiting exemplary photograph of 14 days old *Brachypodium* in soil medium.

Figure 18A:
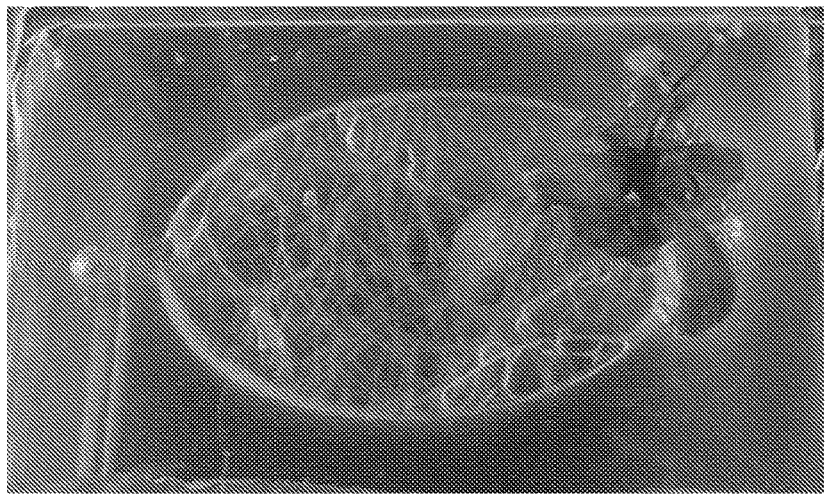
FIGS. 18A-18C show non-limiting exemplary photographs of *Brachypodium ditachyon* and *Arabidopsis* in its respective reproduction stage.
Figure 18B:
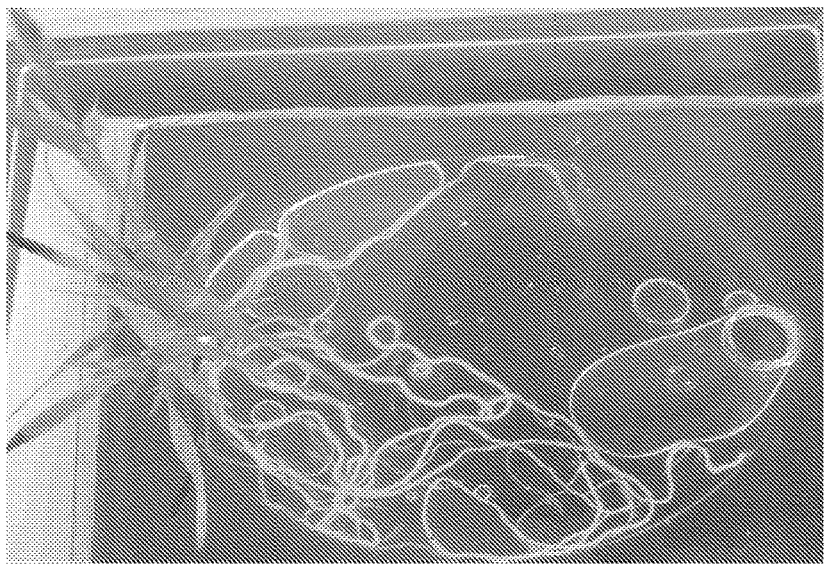
Figure 18C:
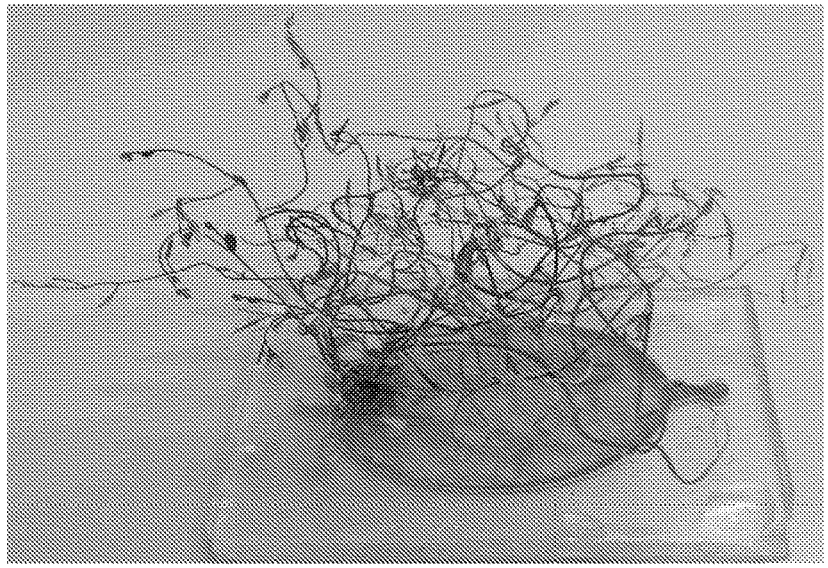

FIGS. 17A-17C show one week old *Arabidopsis, Brachypodium* and switchgrass in plant growth systems, respectively. All these three species were grown in the plant growth systems for at least six weeks. Some of the plants were able to live up to their reproduction stages when growing under optimal light conditions (FIGS. 18A-18C). Thus, plant growth systems can be used for systematic studies of plants, such as their metabolisms and microbiome communities at their different growth stages across their entire life cycles.

Besides liquid nutrient solutions, plant growth systems were used to grow plants in solid media. The PDMS layers of plant growth devices used for solid media were fabricated following 30: 1 ratios of siloxane base and curing agent so they can directly stick onto the microscope slides after loading solid media inside root growth chambers without the aid of plasma treatment. FIGS. 17D-17E show a group of *Brachypodium* plants growing in plant growth systems for two weeks with MS salt solution, sand and soil media, respectively. The thin solid medium layer in root growth chambers allows light penetrate through for the microscopic imaging of root systems, and the reversible sealing feature of plant growth devices enables precise sample collection from specific regions of root rhizospheres.

Altogether, these data demonstrates using plant growth systems for growing various plant species using various forms of growth media, including solid media, until reproduction stages of plants.

Example 12

Plant Growth Systems used in Determining Root Architectures

This example demonstrates using plant growth systems for investigating root architectures.

A root architecture can refer to the spatial configuration and distribution of a plant root system. Root architectures can affect essential physiology responses to diverse growth environments, such as nutrient or water availability. For example, root architectures of many plant species including *Arabidopsis*, maize, rice and tomato can be dramatically influenced by nutrient availabilities in their growth media. *Arabidopsis* under stress of low phosphorus concentration tends to develop root branches in the form of lateral roots and root hairs to enhance its capability of absorbing phosphorus. However, the relevant mechanisms of root architecture developments are lacking.

Figure 19A:
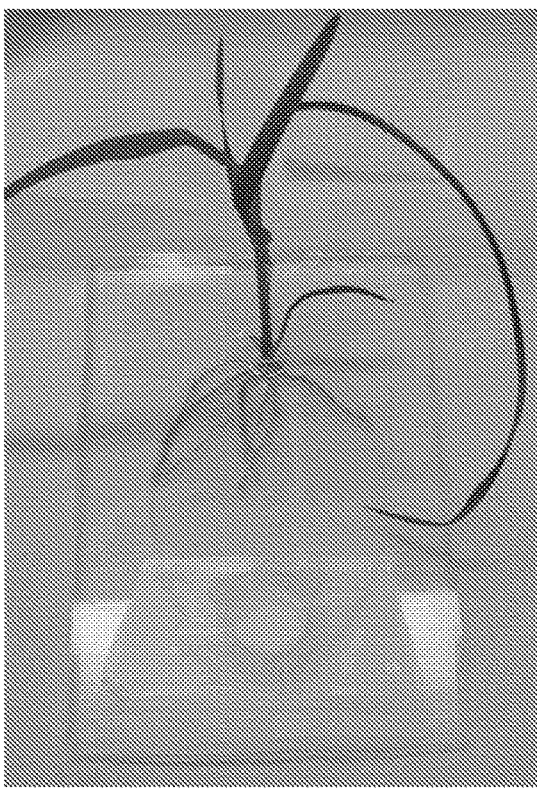
FIGS. 19A-19C show a non-limiting exemplary application of using plant growth systems in tracking root architectures.
Figure 19B:
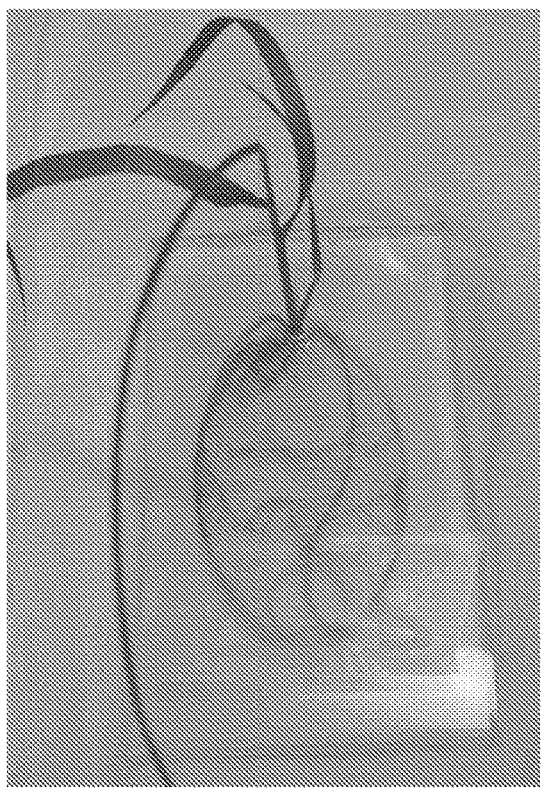
Figure 19C:
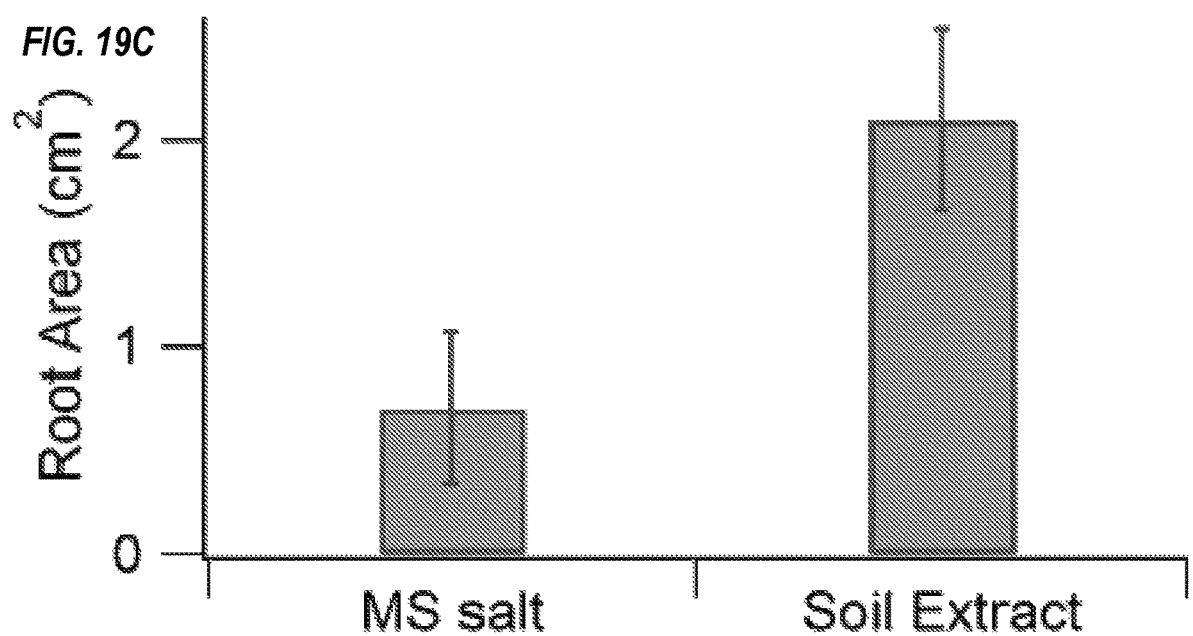

Plant growth systems were used as a convenient approach to explore plant behaviors under different nutrient conditions. FIGS. 19A-19C show a non-limiting exemplary application of plant growth systems in tracking root architectures. FIG. 19A shows a typical switchgrass plant growing in MS salt solution. FIG. 19B shows a typical switchgrass plant growing in soil extract solution. FIG. 19C shows averaged root surface areas of these two groups of switchgrass estimated by ImageJ software (n=3, full picture sets of switchgrass are shown in FIGS. 20A-20G).

As shown in FIGS. 19A-19C, switchgrass generated completely different root morphologies and textures when growing in different medium solutions. Switchgrass in MS salt solution developed a fibrous type of root architectures with short and thick root configurations while the root system of switchgrass in soil extract medium appeared as a type of taproot structures that grew downward to the end of root growth chambers. Averaged root surface area of switchgrass from soil extract medium was three times as big as the surface area from MS salt medium, which could be attributed to nutrient deficiency of soil extract solution that drives switchgrass develop long roots with rich root hairs.

Figure 20A:
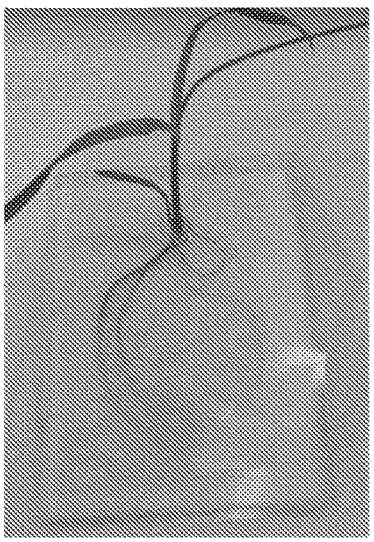
FIGS. 20A-20G show the impact of different media to the root architectures.
Figure 20B:
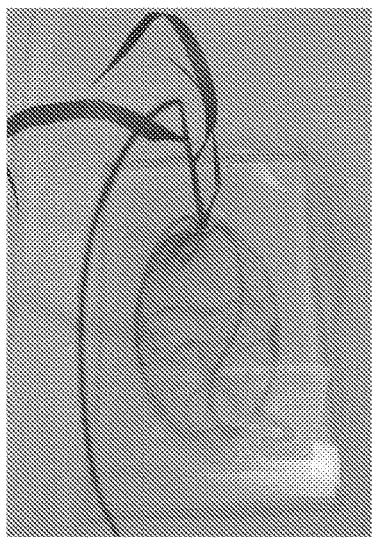
Figure 20C:
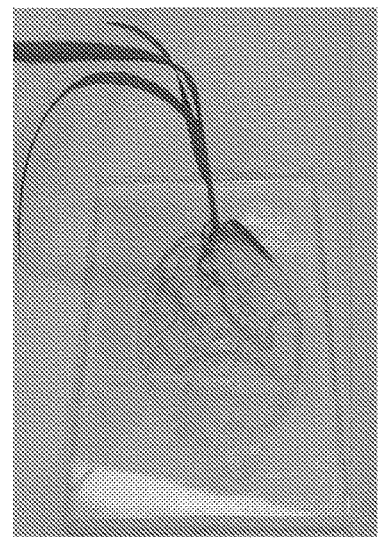
Figure 20D:
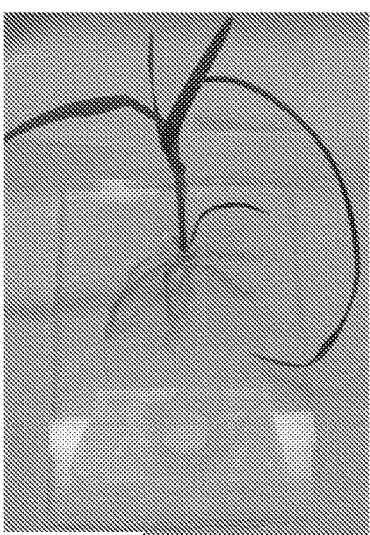
Figure 20E:
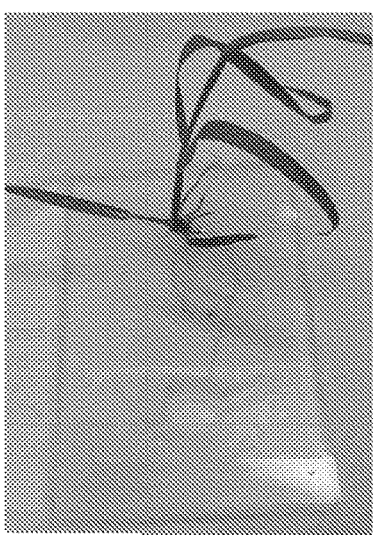
Figure 20F:
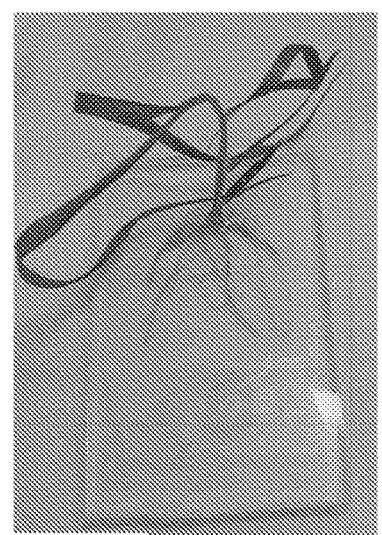
Figure 20G:
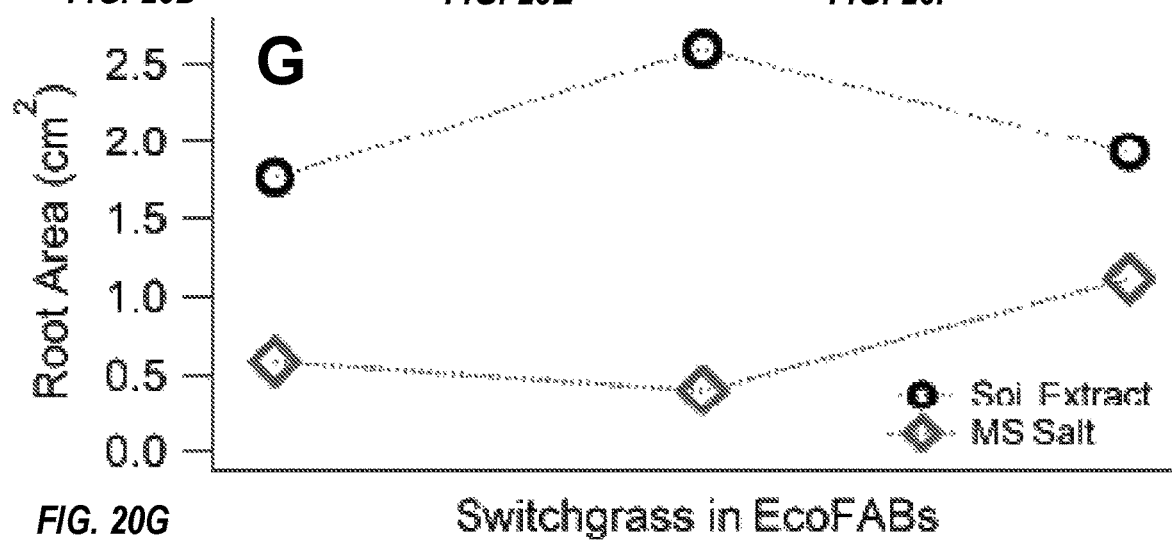

FIGS. 20A-20G show the impact of different media to the root architectures. FIGS. 20A-20C are non-limiting exemplary photographs of switchgrass grown in soil extract medium. FIGS. 20D-20F are non-limiting exemplary photographs of switchgrass grown in MS salt medium. FIG. 20G is a non-limiting exemplary plot showing relative root areas of switchgrass were calculated from ImageJ.

Altogether, these data demonstrates the ability of plant growth systems for imaging and quantifying root architectures can help understand the regulatory mechanisms of plant physiological and molecular signals triggered by plant genotypic adaptions to growth conditions, and promote plant selections targeted for specific growth environments, such as nitrate or phosphorus efficient plants to reduce fertilizer usage.

Example 13

Plant Growth Systems Used in Determining Plant-Microbe Interactions

This example demonstrates using plant growth systems and devices in determining plant-microbe interactions.

In natural environments, plants can interact with a diversity of microorganisms simultaneously. Some species of root microbiome can directly promote plant growth by protecting plants from pathogens or improving nutrient acquisition, while others can alter plant growth environments in a complex manner. Although plant-microbe interactions provide potential strategies to improve plant growth, unraveling the complexity of these interactions and understanding the underlying mechanisms can be difficult. Plant growth systems not only offer a simple approach to visualize root-microbe interactions in real time (FIGS. 15B1-15B17), but also enable us track their metabolomics behaviors over different plant growth periods in a highly controlled environment.

Figure 21C:
FIGS. 21A-21F show that *Brachypodium* roots interacted with *Pseudomonas fluorescens* WCS417 in different media.
Figure 21B:
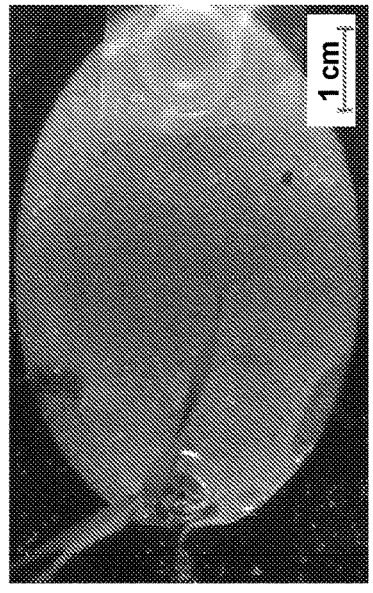
Figure 21A:
Figure 21F:
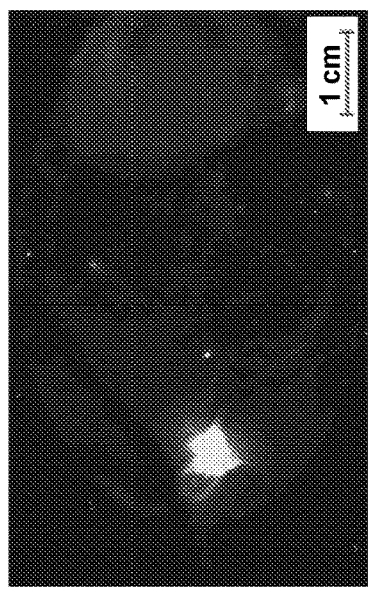
Figure 21E:
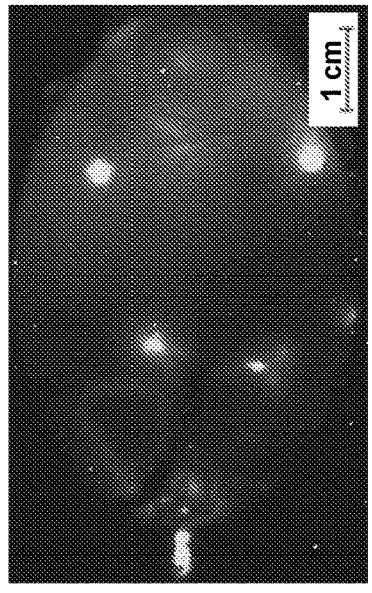
Figure 21D:
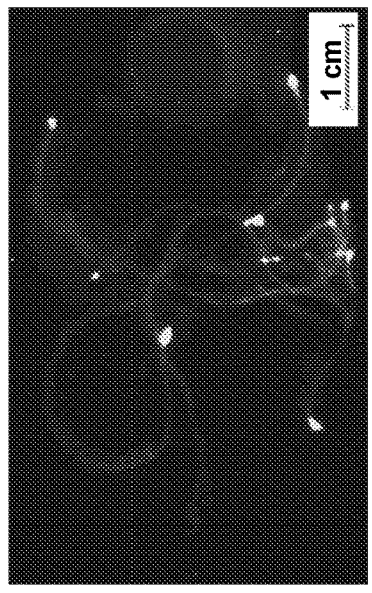
Figure 22A:
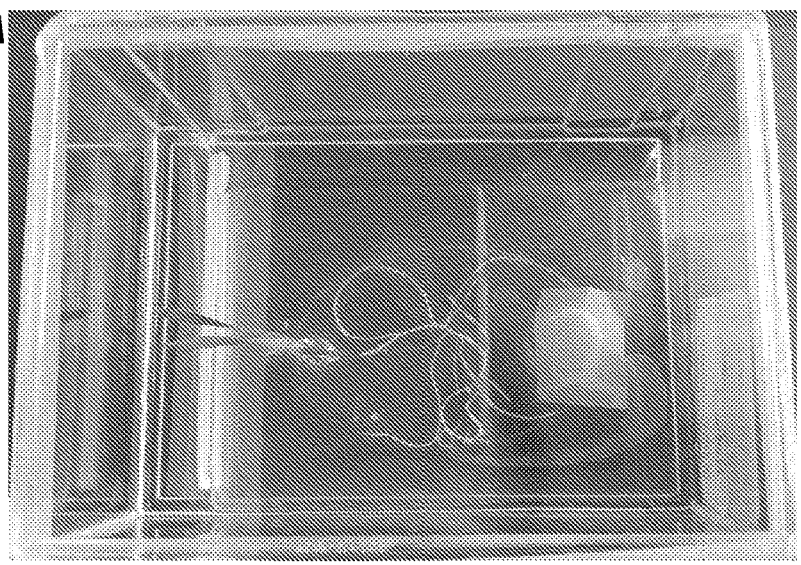
FIGS. 22A-22C are non-limiting exemplary photographs of *Brachypodium* incubated with the *Pseudomonas fluorescens* WCS417 strain in plant growth systems.
Figure 22B:
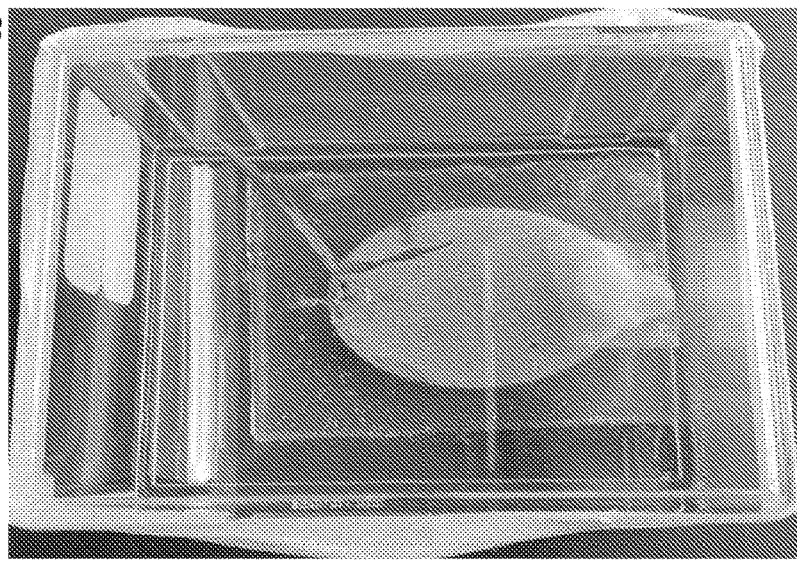
Figure 22C:
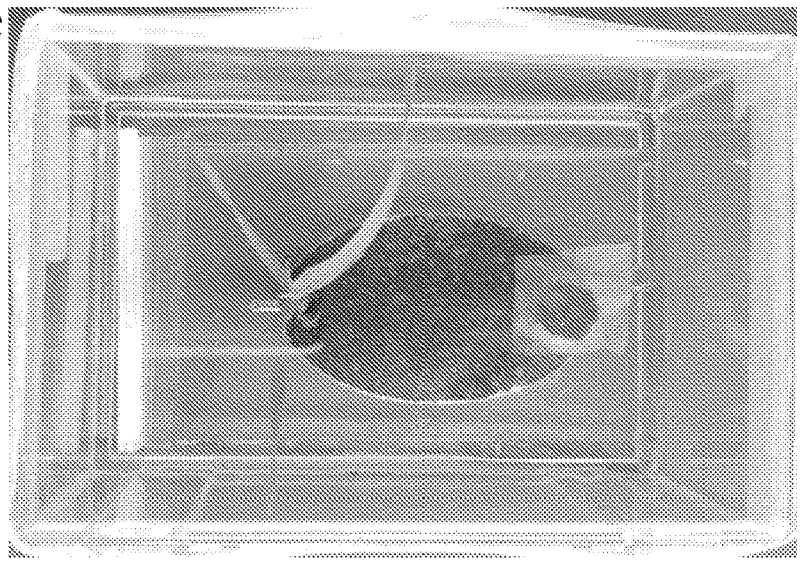

Microorganisms can be transferred into root growth chambers of plant growth devices via outlet channels, and plant-microbe interactions will be tracked over time by direct imaging or exometabolomic analysis. FIGS. 21A-21F show that *Brachypodium* roots interacted with *Pseudomonas fluorescens* WCS417 in different media. FIGS. 21A-21C show non-limiting exemplary white light photographs of the root systems from 15 days old *Brachypodium* growing in MS liquid medium, solid sand medium and soil medium. FIGS. 21D-21F show the corresponding chemiluminescent images of the WCS417 microbes, respectively. The relative photographs of these plants in the entire plant growth systems are shown in FIGS. 22A-22C.

As shown in FIGS. 21A-21F, *Pseudomonas fluorescens* WCS417 (WCS417), a plant growth-promoting rhizobacteria with fluorescent labels, was added into *Brachypodium* root systems with a concentration of $10^6$ cells per plant. The strong chemiluminescent signal from WCS417 was detected with a BIO-RAD gel imager, which indicated the spatial distribution of WCS417 microbes in root growth chambers. In both MS liquid medium and sand solid medium, WCS417 microbes colonized the surfaces of the entire root systems and a great population of microbes gathered around the root tip areas due to the active nutrient production of root tips (FIGS. 21D-21F). On the other hand, the WCS417 microbes in soil medium accumulated around the plant reservoir region instead of root tips (FIG. 21F), which indicated the sufficient nutrient sources from the soil medium so the microbes migrated to the plant reservoir for optimal respiration conditions.

Besides the *Pseudomonas* WCS417 strain, another three rhizobacteria strains with fluorescent labels, *Pseudomonas* 2-79, Ralstonia sp. UNC404CL21 and *Pseudomonas* Q8rl were injected into the root growth chambers with *Brachypodium* growing inside. As shown in FIGS. 22A-22C, all these strains colonized the root surfaces in a similar manner and migrated with root growth over time.

Figure 23B:
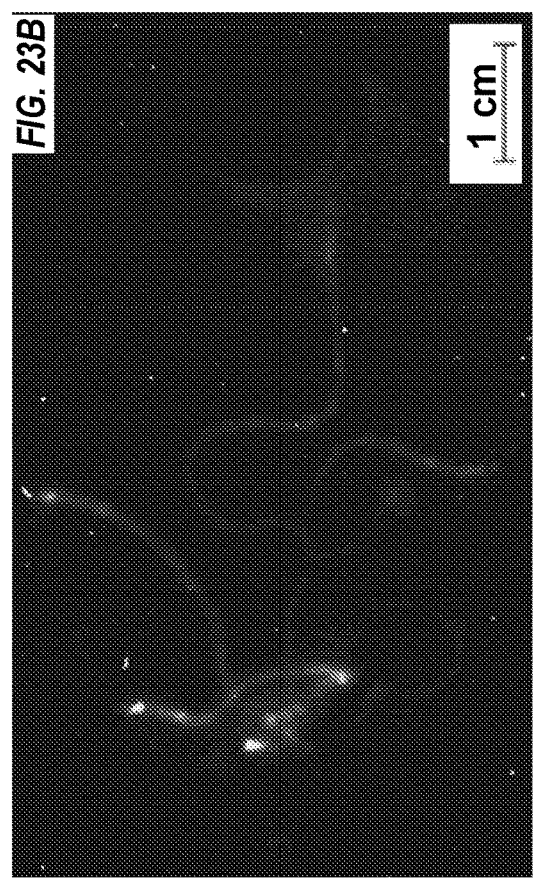
FIGS. 23A-23D are non-limiting exemplary chemiluminescent photographs of *Brachypodium* incubated with four rhizobacteria strains.
Figure 23D:
Figure 23A:
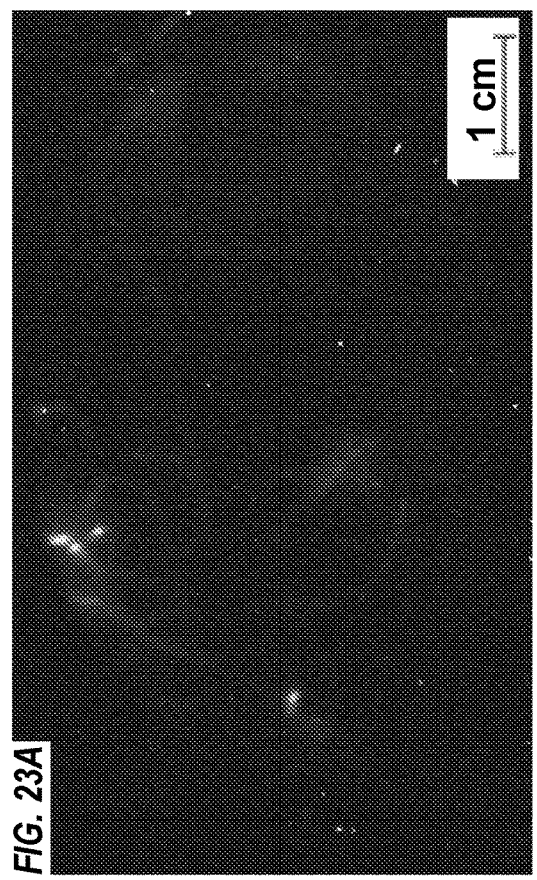
Figure 23C:
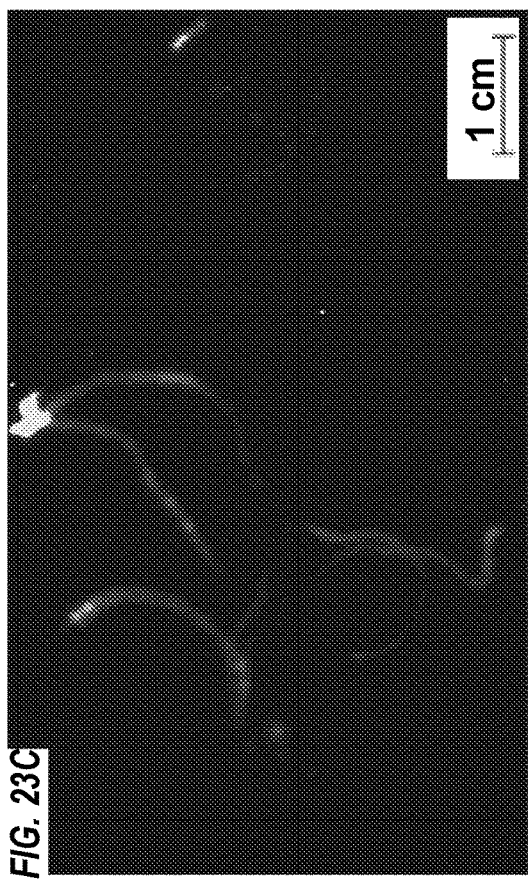

FIGS. 23A-23D are non-limiting exemplary chemiluminescent photographs of *Brachypodium* incubated with four rhizobacteria strains: *Pseudomonas fluorescens* 2-79 (FIG. 23A), *Ralstonia* sp. UNC404CL21 (FIG. 23B), *Pseudomonas fluorescens* Q8rl (FIG. 23C), and *Pseudomonas fluorescens* WCS417 (FIG. 23D). The relative white light photographs of these root systems are shown in FIGS. 24A-24D. FIGS. 24A-24D show non-limiting exemplary white light photographs of *Brachypodium* incubated with four rhizobacteria strains: *Pseudomonas fluorescens* 2-79 (FIG. 24A), *Ralstonia* sp. UNC404CL21 (FIG. 24B), *Pseudomonas fluorescens* Q8rl (FIG. 24C), and *Pseudomonas fluorescens* WCS417 (FIG. 24D).

Figure 25:
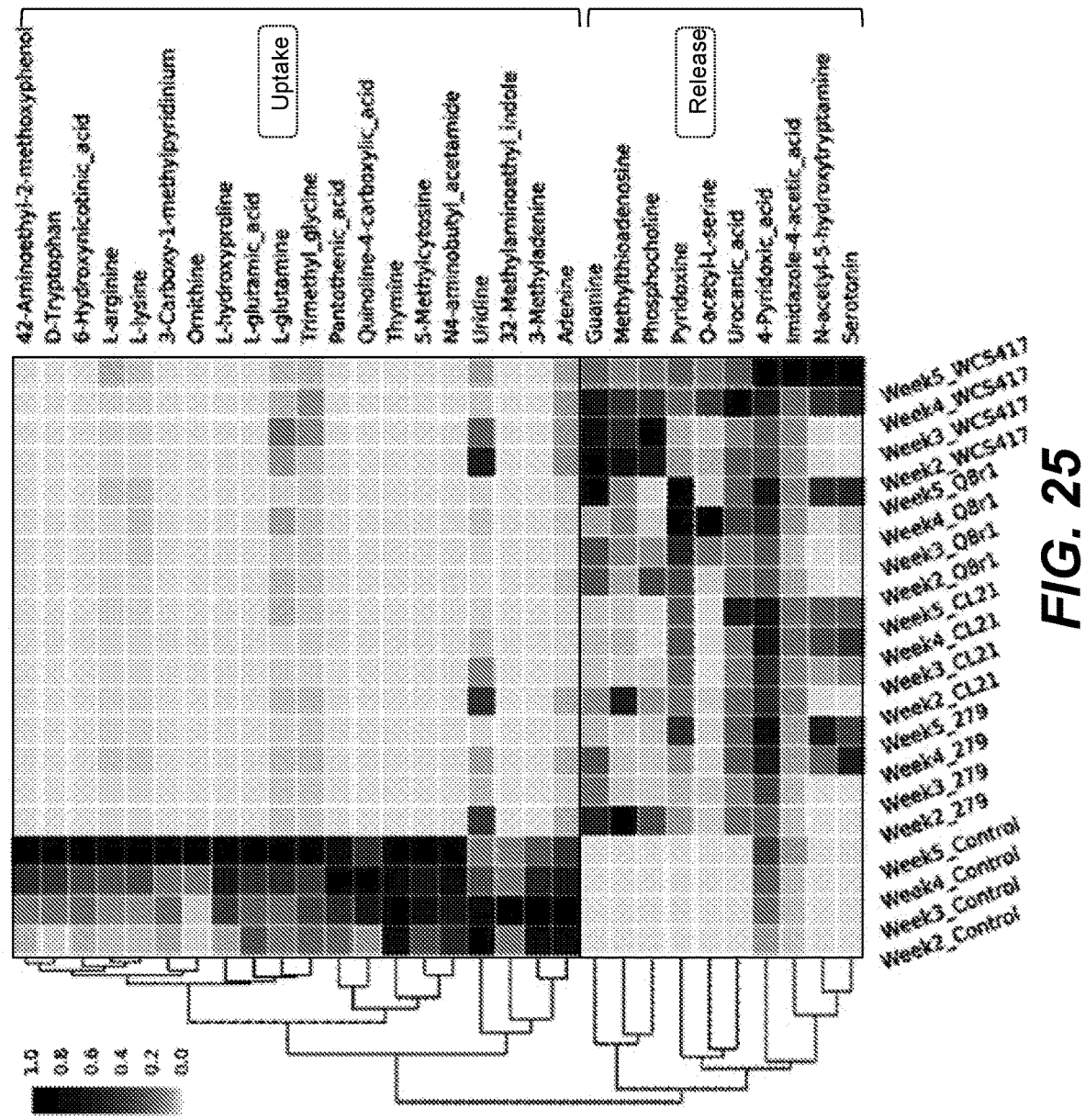
FIG. 25 shows uptake and release of metabolites by plant roots and rhizobacteria strains.

To study metabolite uptake and release from plant-microbe interactions, the exudate solutions from the root growth chambers were collected across different time points of *Brachypodium* growth period (2, 3, 4, 5 week), and then were extracted into methanol solutions for liquid chromatography-mass spectrometry (LC-MS) analysis. As shown in FIG. 25, there was a diversity of metabolites that were detected only when plant roots were colonized with microbes while the amount of some other metabolites were significantly reduced or absent in the root-microbe exudate samples comparing with root exudates without microbes.

FIG. 25 shows uptake and release of metabolites by plant roots and rhizobacteria strains. *Brachypodium* were incubated with four individual strains (*Pseudomonas fluorescens* 2-79, *Ralstonia* sp. UNC404CL21, *Pseudomonas fluorescens* Q8rl, *Pseudomonas fluorescens* WCS417) for five weeks. The intensity of each metabolite was normalized by the maximum value of this ion's LC-MS signals. The control samples were the root exudates of *Brachypodium* without adding any microbes. The comparison of root exudates with individual isolate and without isolates (control samples) are shown in FIGS. 26A-26D.

Figure 26B:
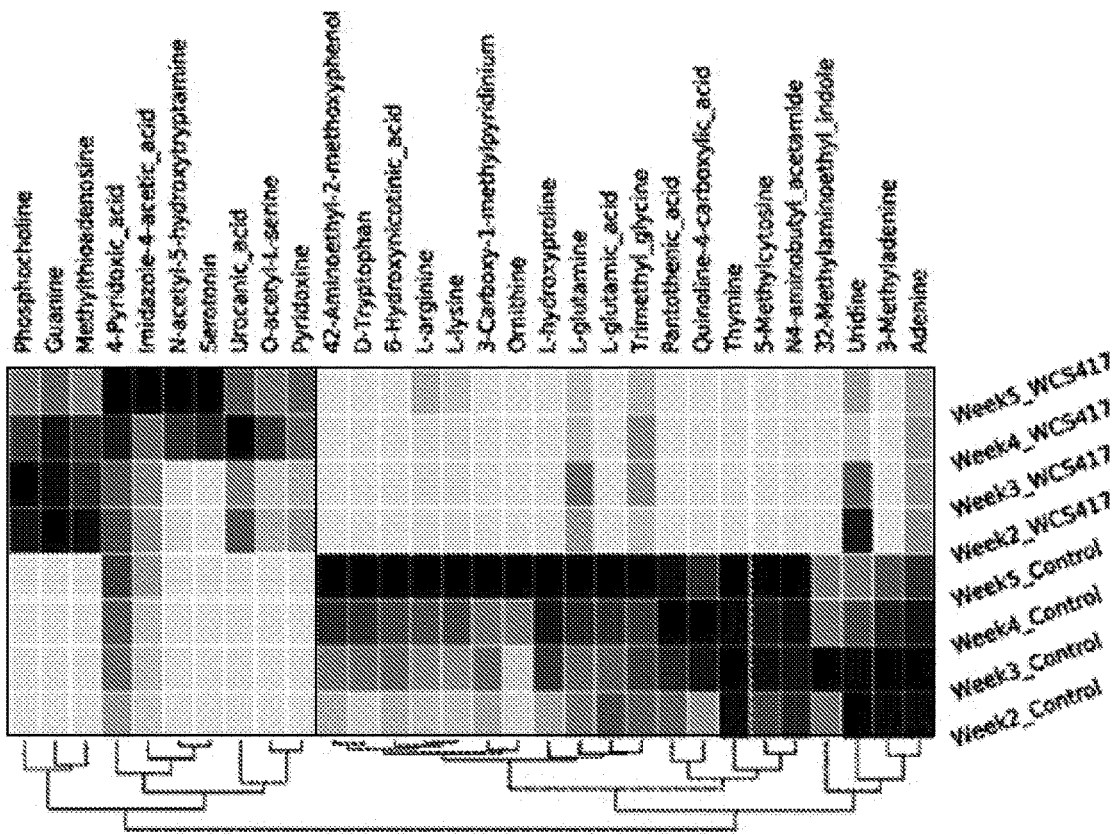
FIGS. 26A-26D show uptake and release of metabolites by plant roots and rhizobacteria strains.
Figure 26A:
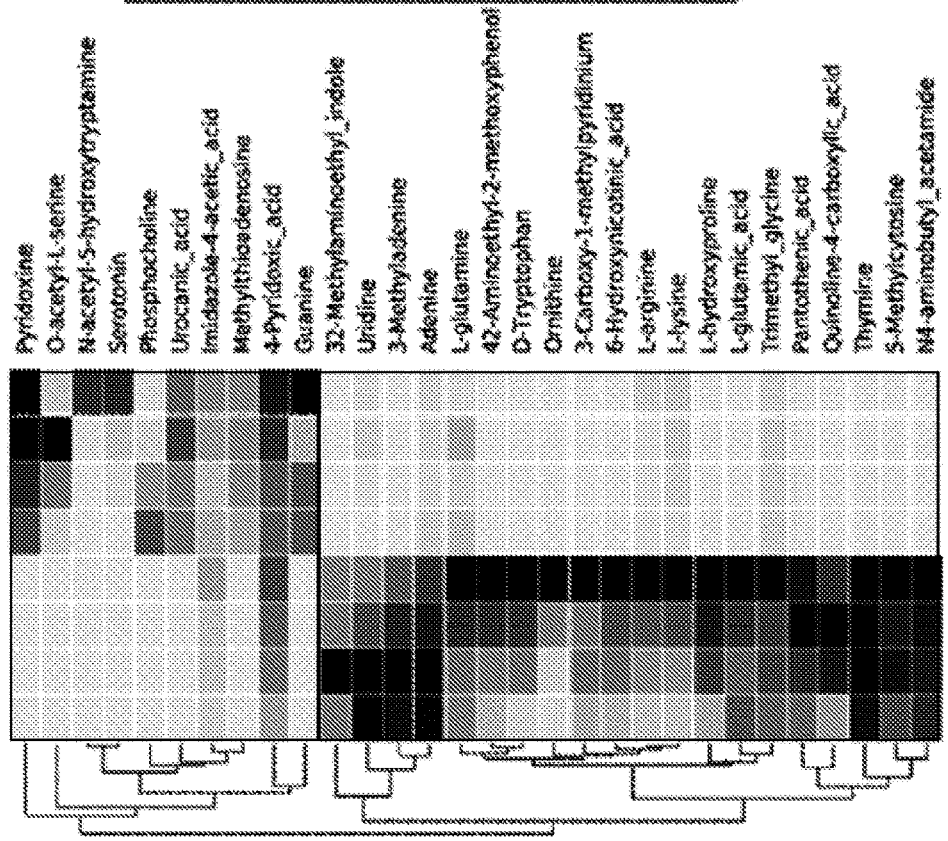
Figure 26D:
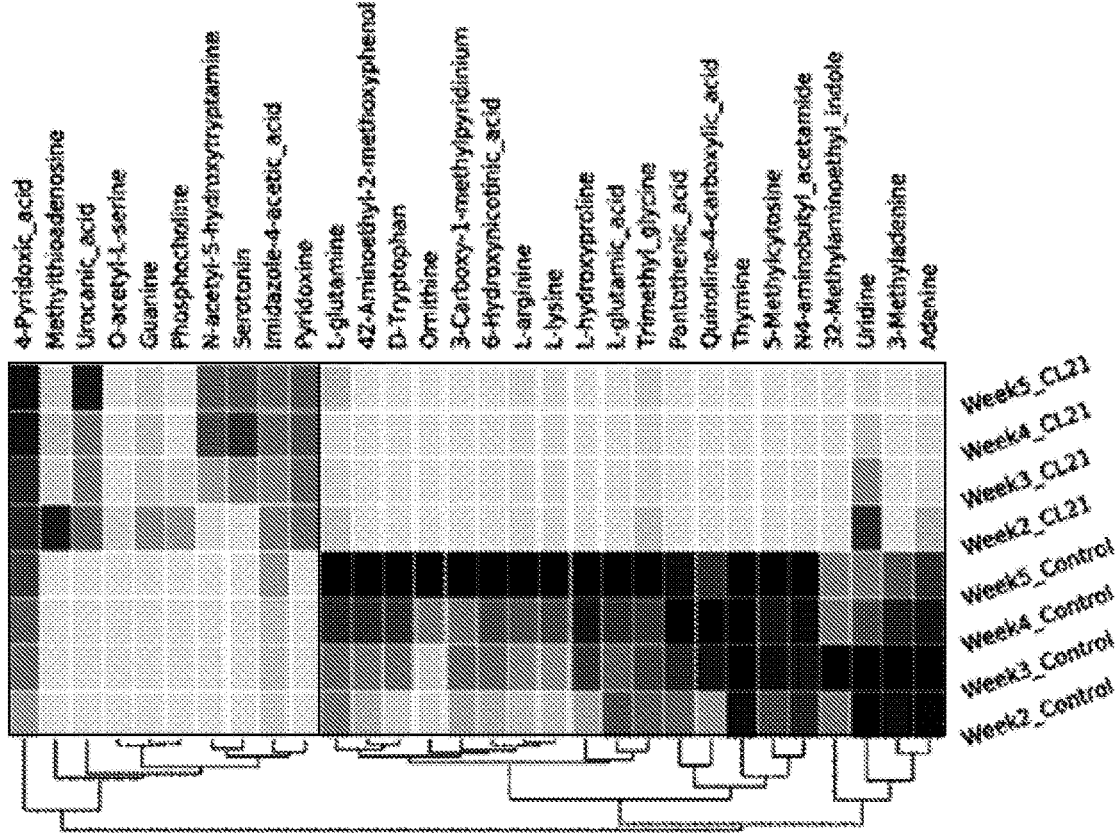
Figure 26C:
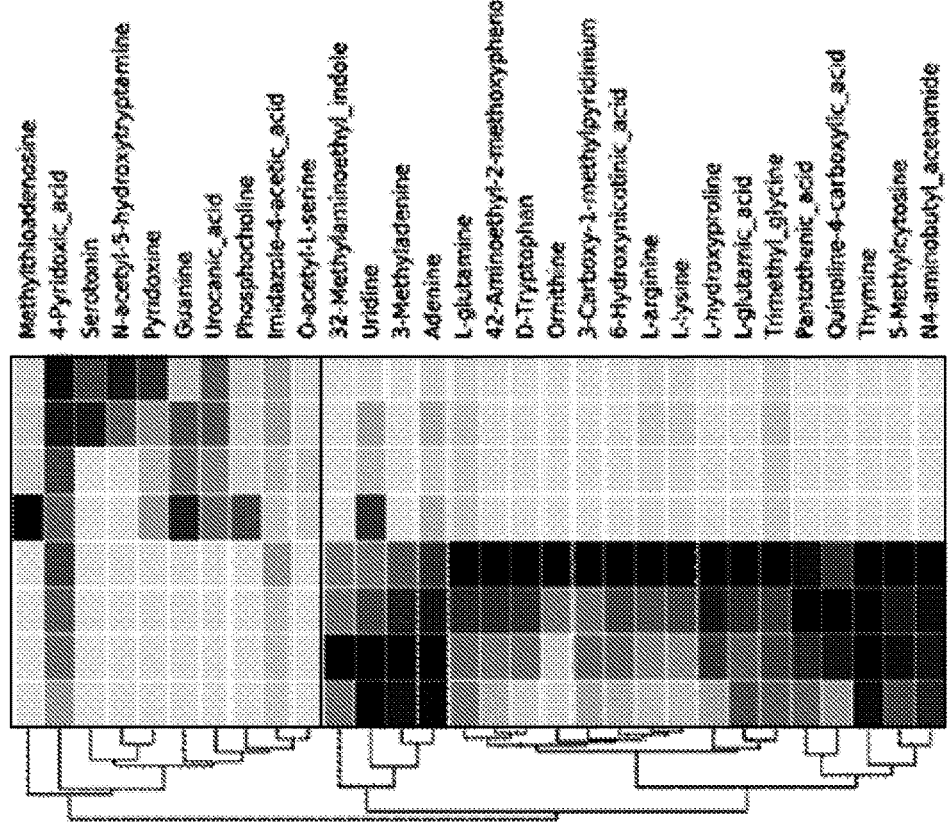

FIGS. 26A-26D show uptake and release of metabolites by plant roots and rhizobacteria strains. *Brachypodium* were incubated with four individual strains: *Pseudomonas fluorescens* 2-79 (FIG. 26A), *Ralstonia* sp. UNC404CL21 (FIG. 26B), *Pseudomonas fluorescens* Q8rl (FIG. 26C), and *Pseudomonas fluorescens* WCS417 (FIG. 26D). The intensity of each metabolite was normalized by the maximum value of this ion's LC-MS signals. The control samples were the root exudates of *Brachypodium* without adding any microbes.

Altogether, these data demonstrates using plant growth systems in determining plant-microbe interactions by analyzing the exudate solutions from the root growth chambers.

Example 14

Determining Plant-Microbe Interactions

This example demonstrates using plant a growth platform for determining plant-microbe interactions.

Each plant growth system included a plant growth device and a plant sized transparent plastic container. One plant growth device had a plant reservoir, a root growth chamber, a 1.6 mm flow inlet and a 1.6 mm outlet for standard plant growth device (FIGS. 5D, 3A2) or a 10 mm outlet for wide-outlet plant growth device (FIGS. 5F, 3A3). The plant reservoir was designed in a trapezoid shape that has a 6 mm top opening and 3 mm bottom opening, and this design reduced the chance of flow leakage during liquid injection and also ensured enough space required for plant growth. The root growth chamber adopted an oval shape with 2 mm depth to fit many model plants' root systems, as shown in FIGS. 5C1, 5C2, 5E1, and 5E2. Both inlet and outlet channels of a standard plant growth device can be connected with PTFE tubing so nutrient solutions can flow into the root growth chamber without opening the plant growth container. The wide-outlet plant growth device greatly reduced flow resistance of the outlet, and was preferably used when growing plants with thick root systems or periodically collecting root exudates after complex root systems are derived from plants.

The casting molds for fabricating PDMS layers of plant growth devices were created in a design software, and then 3D printed in rigid opaque photopolymers, as shown in FIGS. 2A-2J, 5A1-5A2, 5B, 5C1-5C2, 5D, 5E1-5E2, and 5F. Plants inside plant growth devices was directly observed with a microscope using a long work distance, ensuring the sterile grow environment (FIGS. 14D, 15A1-15A18). Plant growth devices with plants could also fit onto a high-resolution microscope stage, which enables higher resolution imaging of plant-microbe interactions (FIGS. 14E, 15B1-15A17). Sterility was not maintained in this environment, and high-resolution imaging is therefore only suitable for endpoint measurements.

The plant growth platform, system, and device of this Example were designed to enable systematic studies of plants, such as their morphology, metabolisms and microbial communities at their different growth stages across their life cycles. Such platform was examined as a general platform to study a variety of plant species. FIGS. 17A-17C show seven-day old *Arabidopsis thaliana, Brachypodium distachyon* and *Panicum virgatum* growing in plant growth systems. All three plants were found to grow well in the plant growth devices for over one month. Both the dicot, *Arabidopsis thaliana* and the monocot, *Brachypodium distachyon* were found to live up to their reproduction stages in the plant growth systems.

The reversible sealing system allowed use of solid substrates (e.g. soil) within the plant growth devices (Protocol 2.2 in Example 4). This reversible sealing approach enabled loading of solid substrates into root growth chambers, and also enables sample collection from specific regions of root rhizospheres. FIGS. 17D-17E show a group of 14-day old *Brachypodium distachyon* growing in hydroponic medium, as well as sand and soil supplemented with hydroponic medium (sand) and water (soil). The thin solid substrate layer in root growth chambers allowed light to penetrate through for microscopic imaging of root systems.

Root morphology can be defined as spatial configuration and distribution of a plant root system which is an essential physiology response to diverse growth environments, such as nutrient or water availability. The plant growth platform, system, and device of this Example provided a convenient approach of studying plant morphology over time or under different nutrient conditions. FIGS. 27A-27F show an example of using plant growth devices to track root morphologies of *Brachypodium distachyon* in the first three weeks. A *Brachypodium distachyon* seedling was transferred into the plant growth device, and its root structure was recorded by a camera inside a BIO-RAD gel imager. Image processing program, such as Image J, python and Matlab, can be further applied to quantify the changes of root morphologies over time or at different medium environments. Quantification of total root area over the course of three weeks showed a gradual increase at the early stage (<1 week) followed by a linear growth trend to the end of three weeks, as shown in FIG. 27G.

FIG. 14D shows directly capturing root growth of *Brachypodium distachyon* in a plant growth device with a long work distance microscope setup. FIG. 14E shows directly observing root-microbe interactions with a high resolution microscope setup. FIGS. 17A-17C show seven-day old *Arabidopsis thaliana* (FIG. 17A), *Brachypodium distachyon* (FIG. 17B), and *Panicum virgatum* (FIG. 17AC) in 0.5 MS hydroponic medium. FIGS. 17D-17F show 14-day old *Brachypodium distachyon* grown in 0.5 MS hydroponics (FIG. 17D), in sand (FIG. 17E) and soil (FIG. 17F) substrate supplied with 0.5 MS medium and water, respectively.

A plant growth system can be to investigate plant-microbe interactions. As described in Protocol 5.4 in Example 6, microorganisms are transferred into root growth chambers of plant growth devices through the inlet channel. FIGS. 21A-21F and 22A-22C show a plant growth device containing *Pseudomonas simea* (formerly, *fluorescens*) WCS417 (WCS417), a plant growth promoting rhizobacteria with chemiluminescent labels, was added into the plant root systems with a concentration of $10^6$ cells per plant. The WCS417 signal was detected with a gel imager, which indicated a distinct spatial distribution of WCS417 microbes in root growth chambers. In both MS liquid medium with and without the sand solid substrate, WCS417 microbes colonized the surfaces of the entire root systems with microbes concentrated around the root tip areas, possibly due to the active nutrient production of root tips (FIGS. 21D-21E). On the other hand, the WCS417 microbes in soil substrate accumulated around the plant reservoir region instead of root tips (FIG. 21F). As the microbes were added through the outlet channel, the microbes were also able to move in the soil substrate, but did not accumulate on the root, as observed in liquid medium with or without sand. This could indicate soil was a sufficient nutrient source, and the microbes migrated to the plant reservoir for optimal respiration conditions.

FIGS. 21A-21F and 22A-22C show using plant growth devices to study root-microbe interactions. FIGS. 22A-22C show a group of 15-day old *Brachypodium distachyon* colonizing with *Pseudomonas fluorescens* WCS417 in different forms of media-MS liquid solution, sand and soil substrates. FIGS. 21A-21C show bright field pictures of their root systems, and FIGS. 21D-21F show the corresponding chemiluminescent images of these root systems after 14 days co-cultivation.

To study metabolite profiling of plant root exudates as well as metabolite uptake and release from plant-microbe interactions, the exudate solutions from the root growth chambers was collected across various growth stages of plants in plant growth devices. As described in Protocol 6 in Example 7, exudate samples are then extracted for LC-MS analysis. Using this method, a range of metabolites exuded by the plant and consumed by the microbes was detected, and the related metabolite profiling of root exudates with and without microbes colonization is currently under investigation.

Altogether, these data demonstrates using plant growth systems for growing various plant species using various forms of growth media, including solid media, until reproduction stages of plants, for imaging and quantifying root architectures, and for determining plant-microbe interactions by analyzing the exudate solutions from the root growth chamber.

Example 15

Plant Growth System with an Outer Chamber

This example demonstrates a plant growth system with an upper outer chamber and a lower outer chamber.

Figure 28C:
FIGS. 28A-28C are photographs of a non-limiting exemplary plant growth system including an outer chamber with an upper portion (upper outer chamber) and a lower portion (lower outer chamber).
Figure 28A:
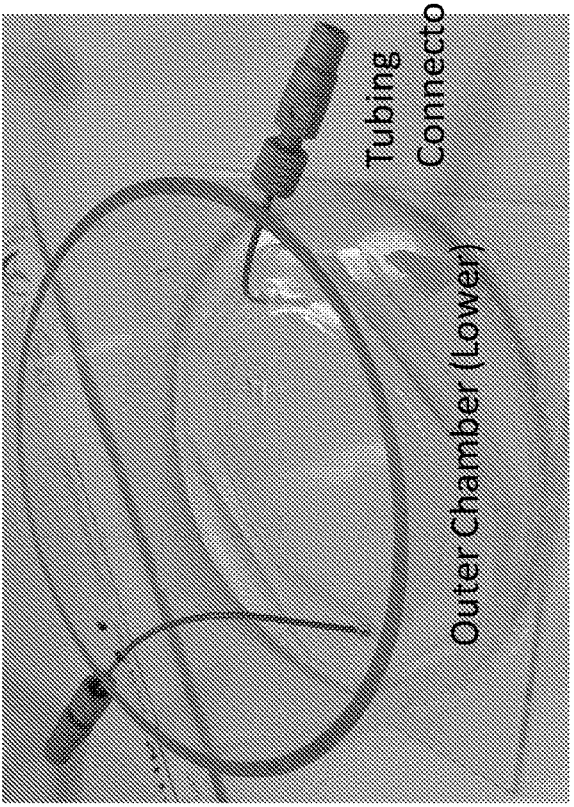
Figure 28B:
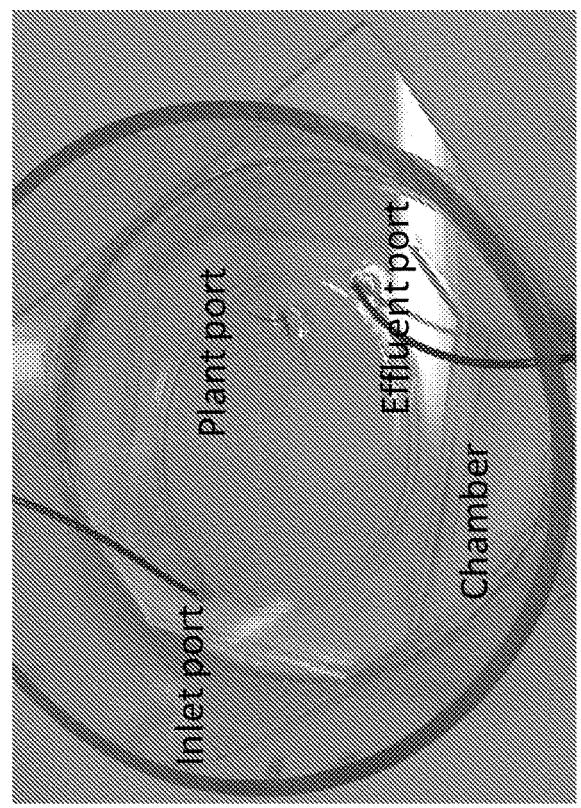

FIGS. 28A-28C are photographs of a plant growth system including an outer chamber with an upper portion (upper outer chamber) and a lower portion (lower outer chamber). The outer chamber for a plant growth system can be made of inert and/or autoclavable materials (e.g., borosilicate, polycarbonate (PC), peek, PTFE and polyester) that allow for easy, aseptic and non-invasive operation of the devices during plant growth.

The lower portion, or base, of an outer chamber can include, or can be, a PC tube (e.g., a 2" tall PC tube (growth cylinder)) bonded to a base (e.g., a borosilicate base). The growth cylinder can be optically clear, suitable to allow in light, and can be easily drilled or otherwise modified for multiple connection types. The low profile of the base can allow for easy addition of plants to the EcoFAB chamber. PTFE or peak tubing can then be used for exchanging and refilling media. The borosilicate base can be sturdy and clear enough for microscopic imaging.

The upper portion of an outer chamber can be, or can include, a growth cylinder of selectable height covered in polyester film (0.5 mil) that can withstand high temperatures.

Each portion can be sterilized via autoclaving (or other suitable means) and then assembled following plant and substrate addition using porous tape or other methods, depending on the application.

For gas-tight operation, the growth cylinder can be made from blown borosilicate gas and the two pieces secured together using a rubber gasket.

The EcoFAB, within the outer chamber can then be maintained within a controlled environment through liquid exchange using the tubing ports. This can be done individually, or through using a docking station.

Figure 29E:
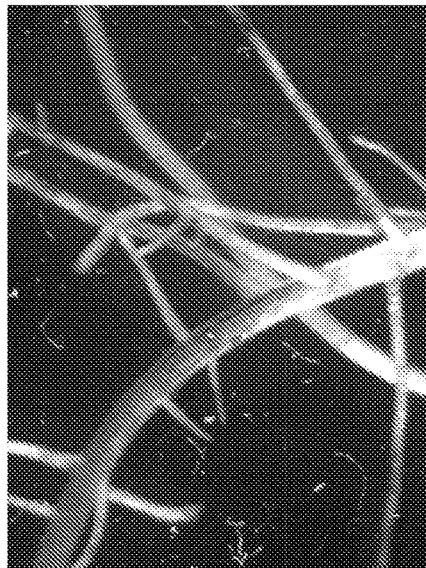
Figure 29F:
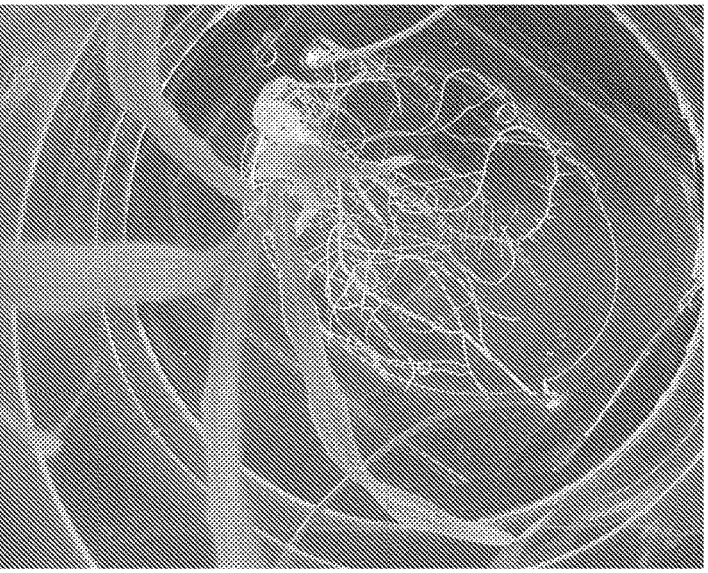
Figure 29D:
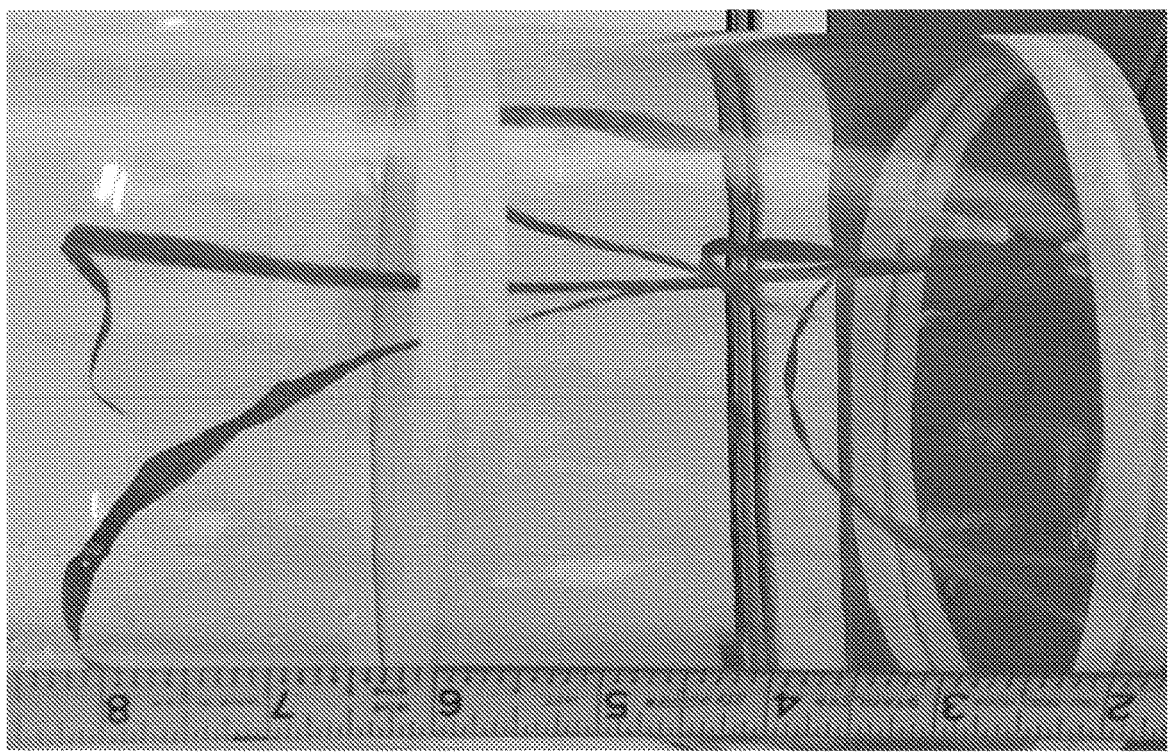

A plant growth system illustrated in FIGS. 28A-28C can be used to grow a wide range of plants (e.g., plants useful for research, education, or commercial purposes) as shown in FIGS. 29A-29F. FIGS. 29A-29B show two-week old maize profiled from the side (FIG. 29A) and above (FIG. 29B). FIG. 29C shows a plant growth container or chamber placed in a controlled growth environment. FIGS. 29D-29F show four-week old Sorghum profiled from the side (FIG. 29D), above (FIG. 29E), and using a stereoscope (FIG. 29F).

Altogether, these data demonstrates a plant growth system with an upper outer chamber and a lower outer chamber can be used to grow a variety of plants using identical, or similar, lower portions and upper portions selected based on the heights, or expected heights, of the plants grown.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device for determining plant growth, comprising:
   (i) a root chamber configured to allow a root of a plant to grow, wherein the root chamber is connected with:
      an inlet channel for introducing a medium into the root chamber,
      an outlet channel for collecting plant exudates and metabolites, and
      a plant reservoir for the plant shoot of the plant to grow; and
   (ii) an outer chamber for the plant to grow comprising an upper chamber and a lower chamber having an air-tight seal in-between.

2. The device of claim 1, wherein the root chamber has a volume of 1-5 ml.

3. The device of claim 1, wherein the root chamber is created by a cavity of a first layer and a second layer.

4. The device of claim 3, wherein the first layer comprises a polydimethylsiloxane (PDMS) layer.

5. The device of claim 3, wherein the second layer comprises a glass layer.

6. The device of claim 3, wherein the first layer is reversibly attached to the second layer.

7. The device of claim 3, wherein the first layer is permanently bond to the second layer.

8. The device of claims 3, wherein the inlet channel, the outlet channel, and the plant reservoir are disposed in the first layer.

9. The device of claim 1, wherein the device is formed using a mold.

10. The device of claim 9, wherein the mold comprises a base piece and a side piece, and wherein the base piece is reversibly attached to the side piece to form the mold.

11. The device of claim 1, wherein the medium comprises one or more microorganisms.

12. The device of claim 1, wherein the medium comprises a solid medium, a liquid medium, a gaseous medium, or a combination thereof.

13. The device of claim 1, wherein the device and/or the root chamber is configured for vertical placement or operation.

14. The device of claim 1, wherein the device and/or the root chamber is configured for horizontal placement or operation.

15. The device of claim 1, wherein the lower chamber comprises a base connected to a tube.

16. The device of claim 1, wherein the upper chamber comprises a tube, wherein the height of the tube is selected based on the plant.

17. The device of claim 1, wherein the air-tight seal between the lower chamber and the upper chamber is formed by a rubber gasket between the lower chamber and the upper chamber.

18. A system for determining plant-microbe interactions, comprising:
a device of claim 1, and
a docking station for temperature control of the device, media introduction into the device, sampling from the device, lighting of the device, imaging the root chamber, performing spectroscopy analysis, or a combination thereof.

19. The system of claim 18, wherein the docking station comprises at least one docking bay for receiving the device.

20. The system of claim 18, wherein the docking station comprises a growth light.

21. The system of claim 18, wherein the system comprises a liquid handling device.

22. The system of claim 18, wherein the system comprises a storage device.

23. A method for determining plant-microbe interactions, comprising:
growing a plant in a medium comprising one or more microorganisms using a system of claim 18, and
performing an analysis of the plant.

24. The method of claim 23, wherein the analysis includes imaging the plant and spectroscopy analysis of the plant.

25. The method of claim 24, wherein imaging the plant comprises light imaging the plant and performing Nanostructure-Initiator Mass Spectrometry (NIMS) analysis of the plant.

* * * * *